(12) United States Patent
Yamahiro et al.

(10) Patent No.: US 7,399,819 B2
(45) Date of Patent: Jul. 15, 2008

(54) SILICON COMPOUND

(75) Inventors: Mikio Yamahiro, Yokohama (JP); Hisao Oikawa, Yokohama (JP); Kazuhiro Yoshida, Yokohama (JP); Kenya Ito, Yokohama (JP); Yasuhiro Yamamoto, Yokohama (JP); Masami Tanaka, Yokohama (JP); Nobumasa Ootake, Yokohama (JP); Kenichi Watanabe, Yokohama (JP); Kohji Ohno, Uji (JP); Yoshinobu Tsujii, Uji (JP); Takeshi Fukuda, Uji (JP)

(73) Assignee: Chisso Corporation, Osaka (JP)

( * ) Notice: Subject to any disclaimer, the term of this patent is extended or adjusted under 35 U.S.C. 154(b) by 305 days.

(21) Appl. No.: 10/528,001

(22) PCT Filed: Sep. 17, 2003

(86) PCT No.: PCT/JP03/11856

§ 371 (c)(1),
(2), (4) Date: Jul. 25, 2005

(87) PCT Pub. No.: WO2004/026883

PCT Pub. Date: Apr. 1, 2004

(65) Prior Publication Data

US 2006/0094849 A1    May 4, 2006

(30) Foreign Application Priority Data

Sep. 17, 2002  (JP) ............................. 2002-270429
May 7, 2003    (JP) ............................. 2003-129350

(51) Int. Cl.
C08G 77/24 (2006.01)
(52) U.S. Cl. ............................. 528/34; 528/31; 528/33
(58) Field of Classification Search ................... 528/33, 528/34, 10, 42, 70
See application file for complete search history.

(56) References Cited

U.S. PATENT DOCUMENTS

| | | | | |
|---|---|---|---|---|
| 5,942,638 | A * | 8/1999 | Lichtenhan et al. | 556/460 |
| 6,162,882 | A * | 12/2000 | Matyjaszewski et al. | 526/111 |
| 6,425,936 | B1 | 7/2002 | Sammons et al. | |
| 6,458,903 | B1 * | 10/2002 | Nakagawa et al. | 526/147 |
| 6,558,455 | B2 | 5/2003 | Sammons et al. | |
| 7,053,167 | B2 * | 5/2006 | Ito et al. | 528/31 |
| 2003/0033931 | A1 | 2/2003 | Sammons et al. | |
| 2003/0055193 | A1 * | 3/2003 | Lichtenhan et al. | 528/10 |

FOREIGN PATENT DOCUMENTS

| | | |
|---|---|---|
| JP | 2-67290 | 3/1990 |
| WO | 00/76634 | 12/2000 |
| WO | 01/10871 | 2/2001 |
| WO | 01/46295 | 6/2001 |
| WO | 02/059208 | 8/2002 |
| WO | 03/052014 | 6/2003 |

OTHER PUBLICATIONS

Supplementary European Search Report mailed Jan. 22, 2008 for European application No. EP 03797641.
"Organic/Inorganic Nanocomposite Star Polymers via Atom Transfer Radical Polymerization of Methyl Methacrylate Using Octafunctional Silsesquioxane Cores", Macromolecules, 2001, 34(16), pp. 5398-5407, XP-002464002.

* cited by examiner

Primary Examiner—Mark Eashoo
Assistant Examiner—Thomas Matochik
(74) Attorney, Agent, or Firm—Wenderoth, Lind & Ponack, L.L.P.

(57) ABSTRACT

A large part of conventional organic-inorganic composite materials is obtained by mechanical blending silsesquioxanes with organic polymers, and therefore it has been very difficult to control the structure thereof as the molecular aggregate of the composite materials. An object of the present invention is to provide a novel silicon compound having a living radical polymerization-initiating ability for an addition-polymerizable monomer and a polymer obtained using the same to thereby solve the problem described above regarding the conventional organic-inorganic composite materials. The present inventors have found that a novel silsesquioxane derivative to which a group having an ability to initiate polymerization of a monomer is useful as means for solving the problem described above. That is, the silsesquioxane derivative of the present invention is represented by Formula (1):

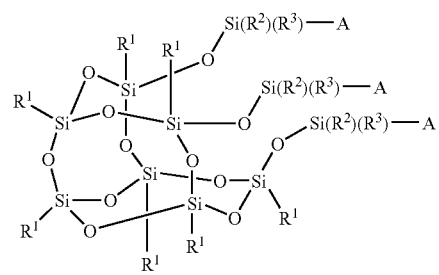

wherein $R^1$ is hydrogen, alkyl, aryl or arylalkyl; $R^2$ and $R^3$ are alkyl, phenyl or cyclohexyl; and A is a group having an ability to initiate polymerization of a monomer.

10 Claims, No Drawings

SILICON COMPOUND

FIELD OF THE INVENTION

The present invention relates to a novel silicon compound characterized by having a polymerization initiating ability for addition-polymerizable monomers, a production process for the same and a polymer obtained using the same.

BACKGROUND OF THE INVENTION

Polymers have come to be used in various fields not only as a general-purpose structure-forming material but also as a value-added type material having functions and performances of a high degree. This is followed by an increase in the importance of producing high molecular materials under precise design. Attentions are paid on silsesquioxane derivatives of a cage type having a dimethylsiloxy group as an organic-inorganic composite material containing silsesquioxane as an inorganic component. This is because they are expected to be applied to precursors of organic/inorganic hybrid materials, low dielectric materials, optical crystals and liquid crystal materials, and the reason therefor resides in that the above silsesquioxane derivatives have a structure close to silica and zeolite. Cage type silsesquioxanes in which a hydroxyl group (document 1), an epoxy group (document 2) or a methacryloyloxy group (document 3) is bonded to a dimethylsiloxy group are reported. So-called organic-inorganic composite materials of organic polymers and silsesquioxanes are prepared by making use of the above functional groups. The organic-inorganic composite materials can be obtained by radically polymerizing cage type silsesquioxanes having a methacryloyloxy group alone or in the presence of other acryl base monomers.

In order to optimize the functions of high molecular materials according to purposes, the molecular properties of a polymer and the properties thereof as a molecular aggregate have to be precisely analyzed, and this makes it necessary to use a polymer having a distinct structure. However, conventional organic-inorganic composite materials do not contain polymers in which a structure is controlled as an organic component including the composite materials described above. A large part of them is obtained by mechanically blending silsesquioxanes with organic polymers, and therefore it used to be very difficult to control a structure thereof as a molecular aggregate of a composite matter. Then, it has come to be tried to control a structure of a polymer by using a polymerization initiator. It is disclosed in a document 4 that an α-haloester group is a good polymerization initiator for styrene base monomers and methacrylic acid base monomers in living radical polymerization, but silsesquioxane derivatives having an α-haloester group have not been known to date.

Document 1: J. Am. Chem. Soc., 122 (2000), 6979-Document 2: Chemistry of Materials, 8 (1996), 1592-Document 3: Macromolecules, 29 (1996), 2327-Document 4: Chem. Rev., 101, 2921-2990 (2001)

DISCLOSURE OF THE INVENTION

The present inventors have found a novel silicon compound having a living radical polymerization initiating ability for addition-polymerizable monomers of a wide range. Then, it has been found that the above silicon compound is effective for solving the problem described above regarding conventional organic-inorganic composite materials. That is, the present invention comprises the following constitutions.

[1] A silicon compound represented by Formula (1):

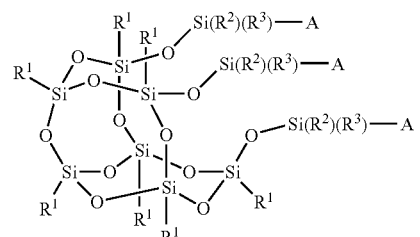

wherein respective $R^1$'s are groups independently selected from hydrogen, alkyl having a carbon atom number of 1 to 40 in which optional hydrogens may be substituted with fluorine and in which optional —$CH_2$— may be substituted with —O—, —CH=CH—, cycloalkylene or cycloalkenylene, substituted or non-substituted aryl and arylalkyl constituted from a substituted or non-substituted aryl group and an alkylene group in which optional hydrogens may be substituted with fluorine and in which optional —$CH_2$— may be substituted with —O— or —CH=CH—; $R^2$ and $R^3$ are groups independently selected from alkyl having a carbon atom number of 1 to 8, phenyl and cyclohexyl; and A is a group having a polymerization initiating ability for a monomer.

[2] The silicon compound as described in the item [1], wherein in Formula (1) as described in the item [1], respective $R^1$'s are groups independently selected from hydrogen, alkyl having a carbon atom number of 1 to 40 in which optional hydrogens may be substituted with fluorine and in which optional —$CH_2$— may be substituted with —O—, —CH=CH—, cycloalkylene or cycloalkenylene, substituted or non-substituted aryl and arylalkyl constituted from a substituted or non-substituted aryl group and an alkylene group in which optional hydrogens may be substituted with fluorine and in which optional —$CH_2$— may be substituted with—O— or —CH=CH—; $R^2$ and $R^3$ are groups independently selected from alkyl having a carbon atom number of 1 to 8, phenyl and cyclohexyl; and A is a group having a living radical polymerization initiating ability for a monomer.

[3] The silicon compound as described in the item [1], wherein in Formula (1) as described in the item [1], respective $R^1$'s are groups independently selected from hydrogen, alkyl having a carbon atom number of 1 to 40 in which optional hydrogens may be substituted with fluorine and in which optional —$CH_2$— may be substituted with —O—, —CH=CH—, cycloalkylene or cycloalkenylene, substituted or non-substituted aryl and arylalkyl constituted from a substituted or non-substituted aryl group and an alkylene group in which optional hydrogens may be substituted with fluorine and in which optional —$CH_2$— may be substituted with —O— or —CH=CH—; $R^2$ and $R^3$ are groups independently selected from alkyl having a carbon atom number of 1 to 8, phenyl and cyclohexyl; and A is a group represented by any of Formula (2-1), Formula (2-2) and Formula (2-3):

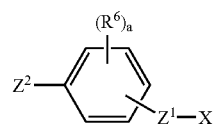

wherein $Z^1$ is alkylene having a carbon atom number of 1 to 3 in which optional —$CH_2$— may be substituted with —O—; $Z^2$ is alkylene having a carbon atom number of 2 to 10 in which optional —$CH_2$— may be substituted with —O—, —COO— or —OCO—; $R^6$ is alkyl having a carbon atom number of 1 to 3; a is an integer of 0 to 2; X is halogen; and a bonding position of $Z^1$ on a benzene ring is a meta position or a para position to a bonding position of $Z^2$, and a bonding position of $R^6$ is an optional position excluding the respective bonding positions of $Z^1$ and $Z^2$;

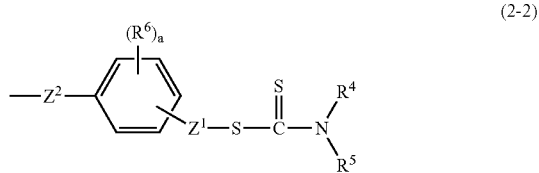

(2-2)

wherein $R^4$ and $R^5$ are independently hydrogen, alkyl having a carbon atom number of 1 to 12, cycloalkyl having a carbon atom number of 5 to 10 or aryl having a carbon atom number of 6 to 10, and $R^4$ and $R^5$ may be combined with each other to form a ring together with N; $Z^1$ is alkylene having a carbon atom number of 1 to 3 in which optional —$CH_2$— may be substituted with —O—; $Z^2$ is alkylene having a carbon atom number of 2 to 10 in which optional —$CH_2$— may be substituted with —O—, —COO— or —OCO—; $R^6$ is alkyl having a carbon atom number of 1 to 3; a is an integer of 0 to 2; and a bonding position of $Z^1$ on a benzene ring is a meta position or a para position to a bonding position of $Z^2$, and a bonding position of $R^6$ is an optional position excluding the respective bonding positions of $Z^1$ and $Z^2$;

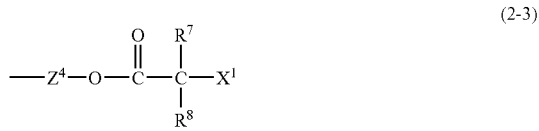

(2-3)

wherein $Z^4$ is alkylene having a carbon atom number of 2 to 20 or alkenylene having a carbon atom number of 3 to 8, and optional —$CH_2$— in these alkylene and alkenylene may be substituted with —O—; $R^7$ is hydrogen, alkyl having a carbon atom number of 1 to 20, aryl having a carbon atom number of 6 to 20 or arylalkyl having a carbon atom number of 7 to 20; $R^8$ is alkyl having a carbon atom number of 1 to 20, aryl having a carbon atom number of 6 to 20 or arylalkyl having a carbon atom number of 7 to 20; and $X^1$ is halogen.

[4] The silicon compound as described in the item [3], wherein respective $R^1$'s are groups independently selected from hydrogen and alkyl having a carbon atom number of 1 to 30 in which optional hydrogens may be substituted with fluorine and in which optional —$CH_2$— may be substituted with —O— or cycloalkylene.

[5] The silicon compound as described in the item [3], wherein respective $R^1$'s are groups independently selected from alkenyl having a carbon atom number of 2 to 20 in which optional hydrogens may be substituted with fluorine and in which optional —$CH_2$— may be substituted with —O— or cycloalkylene and alkyl having a carbon atom number of 1 to 20 in which optional hydrogens may be substituted with fluorine and in which at least one —$CH_2$— is substituted with cycloalkenylene.

[6] The silicon compound as described in the item [3], wherein respective $R^1$'s are groups independently selected from phenyl in which optional hydrogens may be substituted with halogen or alkyl having a carbon atom number of 1 to 10 and non-substituted naphthyl; in alkyl which is a substituent of the phenyl, optional hydrogens may be substituted with fluorine, and optional —$CH_2$— may be substituted with —O—, —CH=CH—, cycloalkylene or phenylene; and when the phenyl has plural substituents, the substituents may be the same group or different groups.

[7] The silicon compound as described in the item [3], wherein respective $R^1$'s are groups independently selected from phenylalkyl constituted from a phenyl group in which optional hydrogens may be substituted with halogen or alkyl having a carbon atom number of 1 to 12 and an alkylene group having a carbon atom number of 1 to 12 in which optional hydrogens may be substituted with fluorine and in which optional —$CH_2$— may be substituted with —O— or —CH=CH—; in alkyl which is a substituent of the phenyl group, optional hydrogens may be substituted with fluorine, and optional —$CH_2$— may be substituted with —O—, —CH=CH—, cycloalkylene or phenylene; and when the phenyl group has plural substituents, the substituents may be the same group or different groups.

[8] The silicon compound as described in the item [3], wherein respective $R^1$'s are groups independently selected from alkyl having a carbon atom number of 1 to 8 in which optional hydrogens may be substituted with fluorine and in which optional —$CH_2$— may be substituted with —O—, —CH=CH—, cycloalkylene or cycloalkenylene, phenyl in which optional hydrogens may be substituted with halogen, methyl or methoxy, non-substituted naphthyl and-phenylalkyl constituted from a phenyl group in which optional hydrogens may be substituted with fluorine, alkyl having a carbon atom number of 1 to 4, vinyl or methoxy and an alkylene group having a carbon atom number of 1 to 8 in which optional —$CH_2$— may be substituted with —O— or —CH=CH—; and when the phenyl or the phenyl group in the phenylalkyl has plural substituents, the substituents may be the same group or different groups.

[9] The silicon compound as described in the item [3], wherein all $R^1$'s are the same group selected from alkyl having a carbon atom number of 1 to 8 in which optional hydrogens may be substituted with fluorine and in which optional —$CH_2$— may be substituted with —O—, —CH=CH—, cycloalkylene or cycloalkenylene, phenyl in which optional hydrogens may be substituted with halogen, methyl or methoxy, non-substituted naphthyl and phenylalkyl constituted from a phenyl group in which optional hydrogens may be substituted with fluorine, alkyl having a carbon atom number of 1 to 4, vinyl or methoxy and an alkylene group having a carbon atom number of 1 to 8 in which optional —$CH_2$— may be substituted with —O— or —CH=CH—; and when the phenyl or the phenyl group in the phenylalkyl has plural substituents, the substituents may be the same group or different groups.

[10] The silicon compound as described in the item [3], wherein all $R^1$'s are the same group selected from ethyl, 3,3,3-trifluoropropyl, 2-methylpropyl, 2,4,4-trimethylpentyl, tridecafluoro-1,1,2,2-tetrahydrooctyl, cyclopentyl, cyclohexyl and phenyl.

[11] The silicon compound as described in the item [3], wherein all $R^1$'s are the same group selected from phenyl and 3,3,3-trifluoropropyl; and $R^2$ and $R^3$ are methyl.

[12] The silicon compound as described in the item [3], wherein all $R^1$'s are the same group selected from alkyl having a carbon atom number of 1 to 8 in which optional hydrogens may be substituted with fluorine and in which optional —$CH_2$— may be substituted with —O—, —CH=CH—, cycloalkylene or cycloalkenylene, phenyl in which optional hydrogens may be substituted with halogen, methyl or methoxy, non-substituted naphthyl and phenylalkyl constituted from a phenyl group in which optional hydrogens may be substituted with fluorine, alkyl having a carbon atom number of 1 to 4, vinyl or methoxy and an alkylene group having a carbon atom number of 1 to 8 in which optional —$CH_2$— may be substituted with —O— or —CH=CH—; when the phenyl or the phenyl group in the phenylalkyl has plural substituents, the substituents may be the same group or different groups; and A is the group represented by Formula (2-1).

[13] The silicon compound as described in the item [3], wherein all $R^1$'s are the same group selected from ethyl, 3,3,3-trifluoropropyl, 2-methylpropyl, 2,4,4-trimethylpentyl, tridecafluoro-1,1,2,2-tetrahydrooctyl, cyclopentyl, cyclohexyl and phenyl; A is the group represented by Formula (2-1); $Z^2$ in Formula (2-1) is $Z^3$-$C_2H_4$—; and $Z^3$ is a single bond or alkylene having a carbon atom number of 1 to 8 in which optional —$CH_2$— may be substituted with —O—, —COO— or —OCO—.

[14] The silicon compound as described in the item [3], wherein all $R^1$'s are the same group selected from phenyl and 3,3,3-trifluoropropyl; $R^2$ and $R^3$ are methyl; A is the group represented by Formula (2-1); and in Formula (2-1), $Z^1$ is —$CH_2$—; $Z^2$ is —$C_2H_4$—; X is chlorine or bromine; and a is 0.

[15] The silicon compound as described in the item [3], wherein all $R^1$'s are the same group selected from alkyl having a carbon atom number of 1 to 8 in which optional hydrogens may be substituted with fluorine and in which optional —$CH_2$— may be substituted with —O—, —CH=CH—, cycloalkylene or cycloalkenylene, phenyl in which optional hydrogens may be substituted with halogen, methyl or methoxy, non-substituted naphthyl and phenylalkyl constituted from a phenyl group in which optional hydrogens may be substituted with fluorine, alkyl having a carbon atom number of 1 to 4, vinyl or methoxy and an alkylene group having a carbon atom number of 1 to 8 in which optional —$CH_2$— may be substituted with —O— or —CH=CH—; when the phenyl or the phenyl group in the phenylalkyl has plural substituents, the substituents may be the same group or different groups; and A is the group represented by Formula (2-2).

[16] The silicon compound as described in the item [3], wherein all $R^1$'s are the same group selected from ethyl, 3,3,3-trifluoropropyl, 2-methylpropyl, 2,4,4-trimethylpentyl, tridecafluoro-1,1,2,2-tetrahydrooctyl, cyclopentyl, cyclohexyl and phenyl; A is the group represented by Formula (2-2); and in Formula (2-2), $Z^2$ is $Z^3$-$C_2H_4$—, and $Z^3$ is a single bond or alkylene having a carbon atom number of 1 to 8 in which optional —$CH_2$— may be substituted with —O—, —COO— or —OCO—.

[17] The silicon compound as described in the item [3], wherein all $R^1$'s are the same group selected from phenyl and 3,3,3-trifluoropropyl; $R^2$ and $R^3$ are methyl; A is the group represented by Formula (2-2); and in Formula (2-2), $R^4$ and $R^5$ are ethyl; $Z^1$ is —$CH_2$—; $Z^2$ is —$C_2H_4$—; and a is 0.

[18] The silicon compound as described in the item [3], wherein all $R^1$'s are the same group selected from alkyl having a carbon atom number of 1 to 8 in which optional hydrogens may be substituted with fluorine and in which optional —$CH_2$— may be substituted with —O—, —CH=CH—, cycloalkylene or cycloalkenylene, phenyl in which optional hydrogens may be substituted with halogen, methyl or methoxy, non-substituted naphthyl and phenylalkyl constituted from a phenyl group in which optional hydrogens may be substituted with fluorine, alkyl having a carbon atom number of 1 to 4, vinyl or methoxy and an alkylene group having a carbon atom number of 1 to 8 in which optional —$CH_2$— may be substituted with —O— or —CH=CH—; $R^2$ and $R^3$ are groups independently selected from alkyl having a carbon atom number of 1 to 8, phenyl and cyclohexyl; and A is the group represented by Formula (2-3).

[19] The silicon compound as described in the item [3], wherein all $R^1$'s are the same group selected from ethyl, 3,3,3-trifluoropropyl, 2-methylpropyl, 2,4,4-trimethylpentyl, tridecafluoro-1,1,2,2-tetrahydrooctyl, cyclopentyl, cyclohexyl and phenyl; A is the group represented by Formula (2-3); and $Z^4$ in Formula (2-3) is alkylene having a carbon atom number of 2 to 10 in which optional —$CH_2$— may be substituted with —O—.

[20] The silicon compound as described in the item [3], wherein all $R^1$'s are the same group selected from phenyl and 3,3,3-trifluoropropyl; $R^2$ and $R^3$ are methyl; A is the group represented by Formula (2-3); and in Formula (2-3), $Z^4$ is —$C_2H_4$—, —$C_3H_6$— or —$C_2H_4$—O—$C_3H_6$—; $R^7$ and $R^8$ are methyl; and X is bromine.

[21] A production process for a silicon compound represented by Formula (1-1) characterized by carrying out a step (a) and then a step (b):

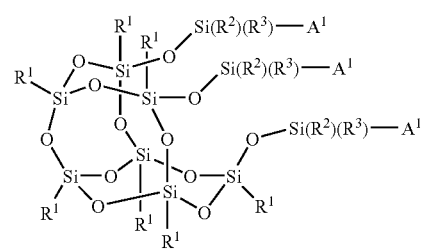

(1-1)

wherein respective $R^1$'s are groups independently selected from hydrogen, alkyl having a carbon atom number of 1 to 40 in which optional hydrogens may be substituted with fluorine and in which optional —$CH_2$— may be substituted with —O—, —CH=CH—, cycloalkylene or cycloalkenylene, substituted or non-substituted aryl and arylalkyl constituted from a substituted or non-substituted aryl group and an alkylene group in which optional hydrogens may be substituted with fluorine and in which optional —$CH_2$— may be substituted with —O— or —CH=CH—; $R^2$ and $R^3$ are groups independently selected from alkyl having a carbon atom number of 1 to 8, phenyl and cyclohexyl; and $A^1$ is a group represented by Formula (2-1-1):

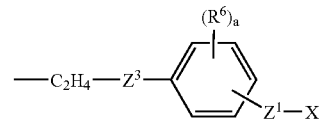

(2-1-1)

wherein $Z^1$ is alkylene having a carbon atom number of 1 to 3 in which optional —$CH_2$— may be substituted with —O—; $Z^3$ is a single bond or alkylene having a carbon atom number of 1 to 8 in which optional —$CH_2$— may be substituted with —O—, —COO— or —OCO—; $R^6$ is alkyl having a carbon atom number of 1 to 3; a is an integer of 0 to 2; X is halogen; and a bonding position of $Z^1$ on a benzene ring is a meta position or a para position to a bonding position of $Z^3$, and a bonding position of $R^6$ is an optional position excluding the respective bonding positions of $Z^1$ and $Z^3$;

<step (a)> a step in which a compound represented by Formula (3-1) is reacted with a compound represented by Formula (4) to thereby obtain a compound represented by Formula (5):

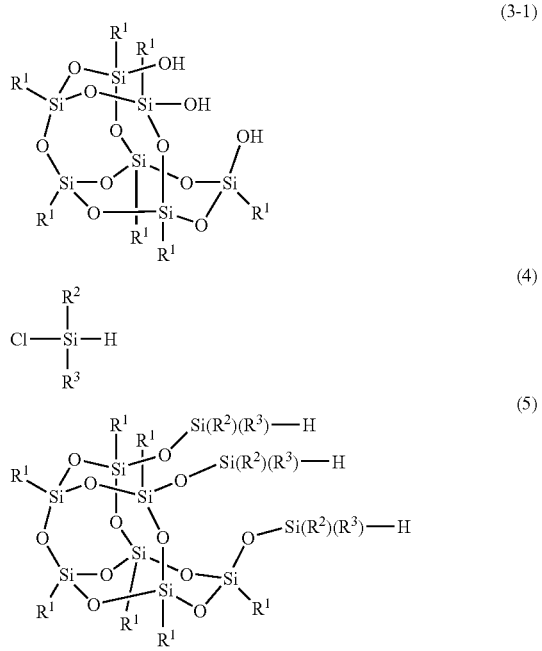

(3-1)

(4)

(5)

wherein $R^1$, $R^2$ and $R^3$ in the above formulas have the same meanings as those of these codes in Formula (1-1);

<step (b)> a step in which the compound represented by Formula (5) is reacted with a compound represented by Formula (6-1) in the presence of a transition metal catalyst to obtain the silicon compound represented by Formula (1-1):

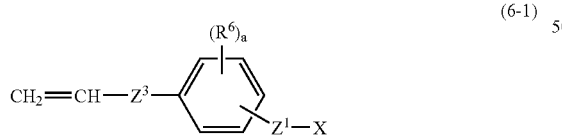

(6-1)

wherein codes in the above formula have the same meanings as those of the respective codes in Formula (2-1-1), and the bonding positions of the substituents are the same as the bonding positions of the substituents in Formula (2-1-1).

[22] The production process as described in the item [21], wherein all $R^1$'s are the same group selected from alkyl having a carbon atom number of 1 to 8 in which optional hydrogens may be substituted with fluorine and in which optional —$CH_2$— may be substituted with —O—, —CH=CH—, cycloalkylene or cycloalkenylene, phenyl in which optional hydrogens may be substituted with halogen, methyl or methoxy, non-substituted naphthyl and phenylalkyl constituted from a phenyl group in which optional hydrogens may be substituted with fluorine, alkyl having a carbon atom number of 1 to 4, vinyl or methoxy and an alkylene group in which optional —$CH_2$— may be substituted with —O—; and $R^2$ and $R^3$ are groups independently selected from alkyl having a carbon atom number of 1 to 8, phenyl and cyclohexyl.

[23] The production process as described in the item [21], wherein all $R^1$'s are the same group selected from ethyl, 3,3,3-trifluoropropyl, 2-methylpropyl, 2,4,4-trimethylpentyl, tridecafluoro-1,1,2,2-tetrahydrooctyl, cyclopentyl, cyclohexyl and phenyl; and $R^2$ and $R^3$ are methyl.

[24] A production process for a silicon compound represented by Formula (1-1) characterized by carrying out a step (c) and then a step (b):

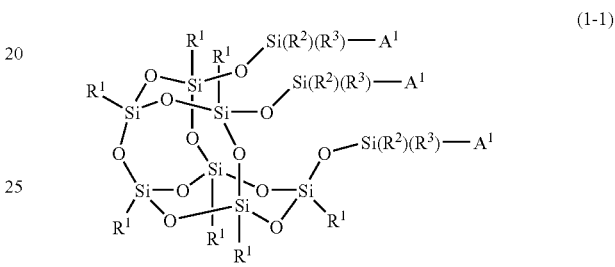

(1-1)

wherein respective $R^1$'s are groups independently selected from hydrogen, alkyl having a carbon atom number of 1 to 40 in which optional hydrogens may be substituted with fluorine and in which optional —$CH_2$— may be substituted with —O—, —CH=CH—, cycloalkylene or cycloalkenylene, substituted or non-substituted aryl and arylalkyl constituted from a substituted or non-substituted aryl group and an alkylene group in which optional hydrogens may be substituted with fluorine and in which optional —$CH_2$— may be substituted with —O— or —CH=CH—; $R^2$ and $R^3$ are groups independently selected from alkyl having a carbon atom number of 1 to 8, phenyl and cyclohexyl; and $A^1$ is a group represented by Formula (2-1-1):

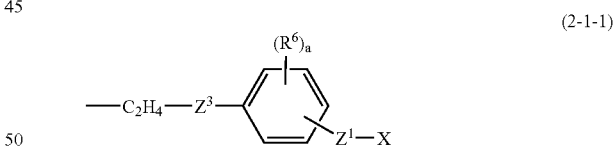

(2-1-1)

wherein $Z^1$ is alkylene having a carbon atom number of 1 to 3 in which optional —$CH_2$— may be substituted with —O—; $Z^3$ is a single bond or alkylene having a carbon atom number of 1 to 8 in which optional —$CH_2$— may be substituted with —O—, —COO— or —OCO—; $R^6$ is alkyl having a carbon atom number of 1 to 3; a is an integer of 0 to 2; X is halogen; and a bonding position of $Z^1$ on a benzene ring is a meta position or a para position to a bonding position of $Z^3$, and a bonding position of $R^6$ is an optional position excluding the respective bonding positions of $Z^1$ and $Z^2$;

<step (c)> a step in which a compound represented by Formula (3-2) is reacted with a compound represented by Formula (4) to thereby obtain a compound represented by Formula (5):

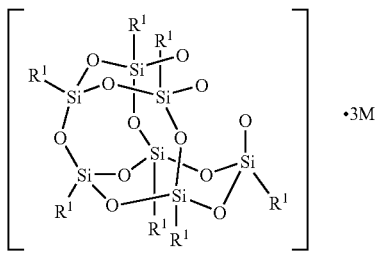

(3-2)

·3M

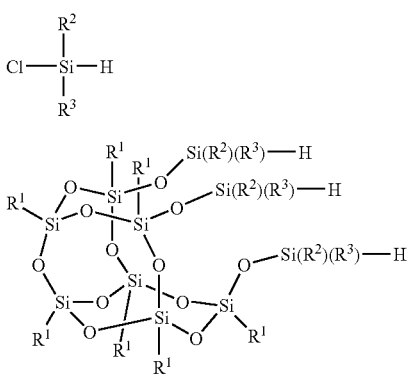

(4)

(5)

wherein $R^1$, $R^2$ and $R^3$ in the above formulas have the same meanings as those of these codes in Formula (1-1), and M is a monovalent alkali metal atom;

<step (b)> a step in which the compound represented by Formula (5) is reacted with a compound represented by Formula (6-1) in the presence of a transition metal catalyst to obtain the silicon compound represented by Formula (1-1):

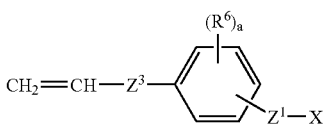

(6)

wherein codes in the above formula have the same meanings as those of the respective codes in Formula (2-1-1), and the bonding positions of the substituents are the same as the bonding positions of the substituents in Formula (2-1-1).

[25] The production process as described in the item [24], wherein all $R^1$'s are the same group selected from alkyl having a carbon atom number of 1 to 8 in which optional hydrogens may be substituted with fluorine and in which optional —$CH_2$— may be substituted with —O—, —CH=CH—, cycloalkylene or cycloalkenylene, phenyl in which optional hydrogens may be substituted with halogen, methyl or methoxy, non-substituted naphthyl and phenylalkyl constituted from a phenyl group in which optional hydrogens may be substituted with fluorine, alkyl having a carbon atom number of 1 to 4, vinyl or methoxy and an alkylene group in which optional —$CH_2$— may be substituted with —O—; and $R^2$ and $R^3$ are groups independently selected from alkyl having a carbon atom number of 1 to 8, phenyl and cyclohexyl.

[26] The production process as described in the item [24], wherein all $R^1$'s are the same group selected from ethyl, 3,3,3-trifluoropropyl, 2-methylpropyl, 2,4,4-trimethylpentyl, tridecafluoro-1,1,2,2-tetrahydrooctyl, cyclopentyl, cyclohexyl and phenyl; and $R^2$ and $R^3$ are methyl.

[27] A production process for a silicon compound represented by Formula (1-2) characterized by reacting a silicon compound represented by Formula (1-1) with a compound represented by Formula (7):

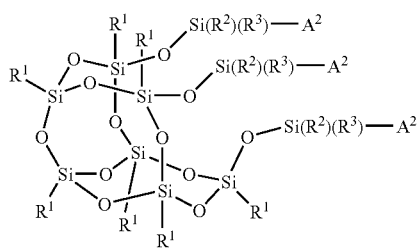

(1-2)

wherein respective $R^1$'s are groups independently selected from hydrogen, alkyl having a carbon atom number of 1 to 40 in which optional-hydrogens may be substituted with fluorine and in which optional —$CH_2$— may be substituted with —O—, —CH=CH—, cycloalkylene or cycloalkenylene, substituted or non-substituted aryl and arylalkyl constituted from a substituted or non-substituted aryl group and an alkylene group in which optional hydrogens may be substituted with fluorine and in which optional —$CH_2$— may be substituted with —O— or —CH=CH—; $R^2$ and $R^3$ are groups independently selected from alkyl having a carbon atom number of 1 to 8, phenyl and cyclohexyl; and $A^2$ is a group represented by Formula (2-2-1):

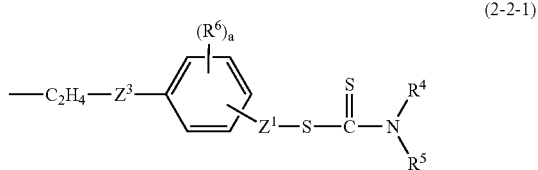

(2-2-1)

wherein $R^4$ and $R^5$ are independently hydrogen, alkyl having a carbon atom number of 1 to 12, cycloalkyl having a carbon atom number of 5 to 10 or aryl having a carbon atom number of 6 to 10, and $R^4$ and $R^5$ may be combined with each other to form a ring together with N; $Z^1$ is alkylene having a carbon atom number of 1 to 3 in which optional —$CH_2$— may be substituted with —O—; $Z^3$ is a single bond or alkylene having a carbon atom number of 1 to 8 in which optional —$CH_2$— may be substituted with —O—, —COO— or —OCO—; $R^6$ is alkyl having a carbon atom number of 1 to 3; a is an integer of 0 to 2; X is halogen; a bonding position of $Z^1$ on a benzene ring is a meta position or a para position to a bonding position of $Z^3$; and a bonding position of $R^6$ is an optional position excluding the respective bonding positions of $Z^1$ and $Z^3$;

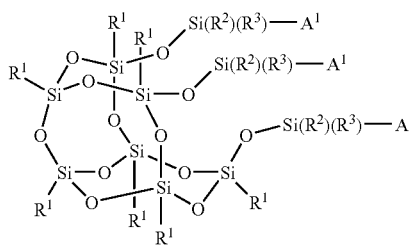

(1-1)

wherein $R^1$, $R^2$ and $R^3$ have the same meanings as those of these codes in Formula (1-2); and $A^1$ is a group represented by Formula (2-1-1);

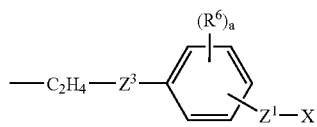

(2-1-1)

wherein $Z^1$, $Z^3$, $R^6$ and a have the same meanings as those of these codes in Formula (2-2-1); X is halogen; and the bonding positions of $Z^1$ and $R^6$ on a benzene ring are the same as these bonding positions in Formula (2-2-1);

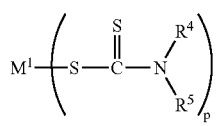

(7)

wherein $R^4$ and $R^5$ have the same meanings as those of these codes in Formula (2-2-1); $M^1$ is a metal element of the first group or the second group in the periodic table; and p is the same value as an atomic value of $M^1$.

[28] The production process as described in the item [27], wherein all $R^1$'s are the same group selected from alkyl having a carbon atom number of 1 to 8 in which optional hydrogens may be substituted with fluorine and in which optional —$CH_2$— may be substituted with —O—, —CH=CH—, cycloalkylene or cycloalkenylene, phenyl in which optional hydrogens may be substituted with halogen, methyl or methoxy, non-substituted naphthyl and phenylalkyl constituted from a phenyl group in which optional hydrogens may be substituted with fluorine, alkyl having a carbon atom number of 1 to 4, vinyl or methoxy and an alkylene group in which optional —$CH_2$— may be substituted with —O—; and $R^2$ and $R^3$ are groups independently selected from alkyl having a carbon atom number of 1 to –8, phenyl and cyclohexyl.

[29] The production process as described in the item [27], wherein all $R^1$'s are the same group selected from ethyl, 3,3,3-trifluoropropyl, 2-methylpropyl, 2,4,4-trimethylpentyl, tridecafluoro-1,1,2,2-tetrahydrooctyl, cyclopentyl, cyclohexyl and phenyl; and $R^2$ and $R^3$ are methyl.

[30] A production process for a silicon compound represented by Formula (1-2) characterized by obtaining a compound represented by Formula (5) by a step (a) or a step (c) and carrying out a step (d) and then a step (e):

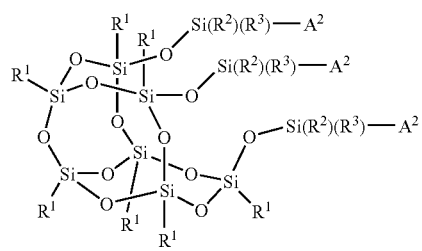

(1-2)

wherein respective $R^1$'s are groups independently selected from hydrogen, alkyl having a carbon atom number of 1 to 40 in which optional hydrogens may be substituted with fluorine and in which optional —$CH_2$— may be substituted with —O—, —CH=CH—, cycloalkylene or cycloalkenylene, substituted or non-substituted aryl and arylalkyl constituted from a substituted or non-substituted aryl group and an alkylene group in which optional hydrogens may be substituted with fluorine and in which optional —$CH_2$— may be substituted with —O— or —CH=CH—; $R^2$ and $R^3$ are groups independently selected from alkyl having a carbon atom number of 1 to 8, phenyl and cyclohexyl; and $A^2$ is a group represented by Formula (2-2-1):

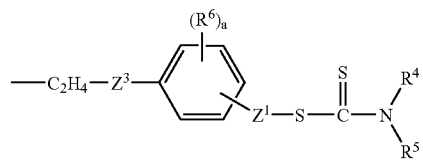

(2-2-1)

wherein $Z^1$ is alkylene having a carbon atom number of 1 to 3 in which optional —$CH_2$— may be substituted with —O—; $Z^3$ is a single bond or alkylene having a carbon atom number of 1 to 8 in which optional —$CH_2$— may be substituted with —O—, —COO— or —OCO—; $R^4$ and $R^5$ are independently hydrogen, alkyl having a carbon atom number of 1 to 12, cycloalkyl having a carbon atom number of 5 to 10 or aryl having a carbon atom number of 6 to 10, and $R^4$ and $R^5$ may be combined with each other to form a ring together with N; $R^6$ is alkyl having a carbon atom number of 1 to 3; a is an integer of 0 to 2; and a bonding position of $Z^1$ on a benzene ring is a meta position or a para position to a bonding position of $Z^3$, and a bonding position of $R^6$ is an optional position excluding the respective bonding positions of $Z^1$ and $Z^3$;

<step (a)> a step in which a compound represented by Formula (3-1) is reacted with a compound represented by Formula (4) to thereby obtain a compound represented by Formula (5):

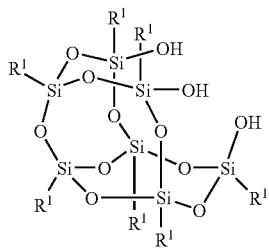
(3-1)

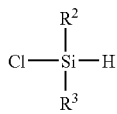
(4)

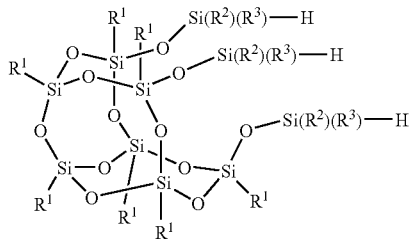
(5)

wherein $R^1$, $R^2$ and $R^3$ in the above formulas have the same meanings as those of these codes in Formula (1-2);

<step (c)> a step in which a compound represented by Formula (3-2) is reacted with the compound represented by Formula (4) to thereby obtain the compound represented by Formula (5):

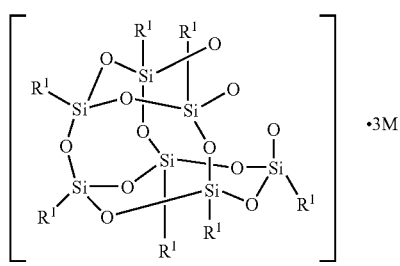
(3-2)

wherein $R^1$ has the same meaning as that of $R^1$ in Formula (1-2); and M is a monovalent alkali metal atom;

<step (d)> a step in which a compound represented by Formula (6-1) is reacted with a compound represented by Formula (7) to obtain a compound represented by Formula (6-2):

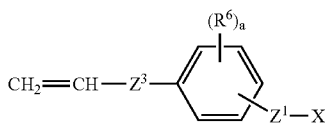
(6-1)

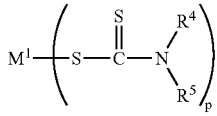
(7)

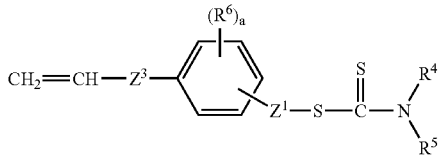
(6-2)

have the same meanings as those of these codes in Formula (2-2-1); the bonding positions of $Z^1$ and $R^6$ on a benzene ring are the same as these bonding positions in Formula (2-2-1); X is halogen; $M^1$ is a metal element of the first group or the second group in the periodic table; and p is the same value as an atomic value of $M^1$;

<step (e)> a step in which the compound represented by Formula (5) is reacted with the compound represented by Formula (6-2) in the presence of a transition metal catalyst to obtain the silicon compound represented by Formula (1-2).

[31] The production process as described in the item [30], wherein all $R^1$'s are the same group selected from alkyl having a carbon atom number of 1 to 8 in which optional hydrogens may be substituted with fluorine and in which optional —$CH_2$— may be substituted with —O—, —CH=CH—, cycloalkylene or cycloalkenylene, phenyl in which optional hydrogens may be substituted with halogen, methyl or methoxy, non-substituted naphthyl and phenylalkyl constituted from a phenyl group in which optional hydrogens may be substituted with fluorine, alkyl having a carbon atom number of 1 to 4, vinyl or methoxy and an alkylene group in which optional —$CH_2$— may be substituted with —O—; and $R^2$ and $R^3$ are groups independently selected from alkyl having a carbon atom number of 1 to 8, phenyl and cyclohexyl.

[32] The production process as described in the item [30], wherein all $R^1$'s are the same group selected from ethyl, 3,3,3-trifluoropropyl, 2-methylpropyl, 2,4,4-trimethylpentyl, tridecafluoro-1,1,2,2-tetrahydrooctyl, cyclopentyl, cyclohexyl and phenyl; and $R^2$ and $R^3$ are methyl.

[33] A production process for a silicon compound represented by Formula (1-1) characterized by carrying out a step (f) and then a step (g):

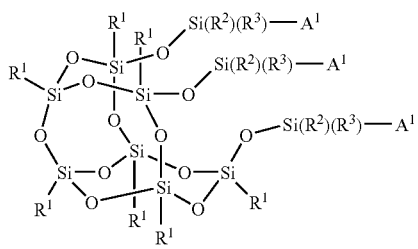
(1-1)

wherein respective $R^1$'s are groups independently selected from hydrogen, alkyl having a carbon atom number of 1 to 40 in which optional hydrogens may be substituted with fluorine and in which optional —$CH_2$— may be substituted with —O—, —CH=CH—, cycloalkylene or cycloalkenylene, substituted or non-substituted aryl and arylalkyl constituted from a substituted or non-substituted aryl group and an alkylene group in which optional hydrogens may be substituted with fluorine and in which optional —$CH_2$— may be substituted with —O— or —CH=CH—; $R^2$ and $R^3$ are groups independently selected from alkyl having a carbon atom number of 1 to 8, phenyl and cyclohexyl; and $A^1$ is a group represented by Formula (2-1-1):

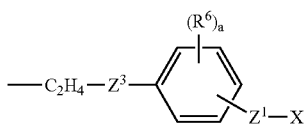
(2-1-1)

wherein $Z^1$ is alkylene having a carbon atom number of 1 to 3 in which optional —$CH_2$— may be substituted with —O—; $Z^3$ is a single bond or alkylene having a carbon atom number of 1 to 8 in which optional —$CH_2$— may be substituted with —O—, —COO— or —OCO—; $R^6$ is alkyl having a carbon atom number of 1 to 3; a is an integer of 0 to 2; X is halogen; and a bonding position of $Z^1$ on a benzene ring is a meta position or a para position to a bonding position of $Z^3$, and a bonding position of $R^6$ is an optional position excluding the respective bonding positions of $Z^1$ and $Z^3$;

<step (f)> a step in which a compound represented by Formula (4) is reacted with a compound represented by Formula (6-1) in the presence of a transition metal catalyst to obtain a compound represented by Formula (8-1):

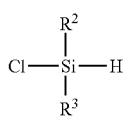
(4)

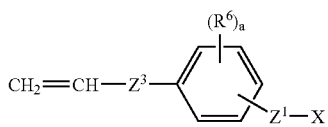
(6-1)

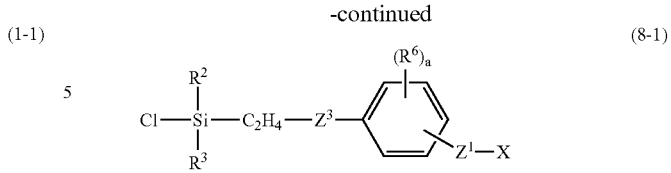
(8-1)

wherein in the above formulas, $R^1$, $R^2$ and $R^3$ have the same meanings as those of these codes in Formula (1-1); $Z^1$, $Z^3$, $R^6$ and a have the same meanings as those of these codes in Formula (2-1-1); the bonding positions of $Z^1$ and $R^6$ on a benzene ring are the same as these bonding positions in Formula (2-1-1); and X is halogen;

<step (g)> a step in which the compound represented by Formula (8-1) is reacted with a compound represented by Formula (3-1) or a compound represented by Formula (3-2) to obtain the compound represented by Formula (1-1):

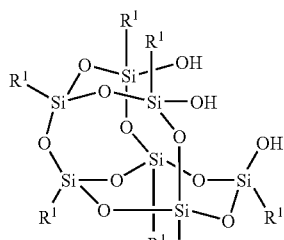
(3-1)

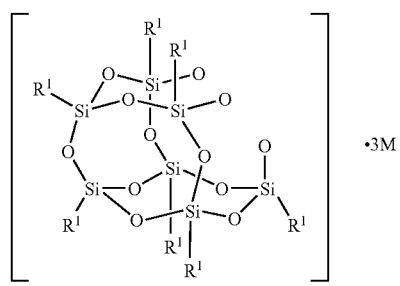
(3-2)

wherein in the above formulas, $R^1$ has the same meaning as that of $R^1$ in Formula (1-1); and M is a monovalent alkali metal atom.

[34] The production process as described in the item [33], wherein all $R^1$'s are the same group selected from alkyl having a carbon atom number of 1 to 8 in which optional hydrogens may be substituted with fluorine and in which optional —$CH_2$— may be substituted with —O—, —CH=CH—, cycloalkylene or cycloalkenylene, phenyl in which optional hydrogens may be substituted with halogen, methyl or methoxy, non-substituted naphthyl and phenylalkyl constituted from a phenyl group in which optional hydrogens may be substituted with fluorine, alkyl having a carbon atom number of 1 to 4, vinyl or methoxy and an alkylene group in which optional —$CH_2$— may be substituted with —O—; and $R^2$ and $R^3$ are groups independently selected from alkyl having a carbon atom number of 1 to 8, phenyl and cyclohexyl.

[35] The production process as described in the item [33], wherein all $R^1$'s are the same group selected from ethyl, 3,3,3-trifluoropropyl, 2-methylpropyl, 2,4,4-trimethylpentyl, tridecafluoro-1,1,2,2-tetrahydrooctyl, cyclopentyl, cyclohexyl and phenyl; and $R^2$ and $R^3$ are methyl.

[36] A production process for a silicon compound represented by Formula (1-2) characterized by obtaining a compound represented by Formula (6-2) by a step (d) and carrying out a step (h) and then a step (i):

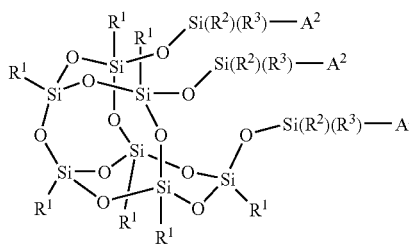
(1-2)

wherein respective $R^1$'s are groups independently selected from hydrogen, alkyl having a carbon atom number of 1 to 40 in which optional hydrogens may be substituted with fluorine and in which optional —$CH_2$— may be substituted with —O—, —CH=CH—, cycloalkylene or cycloalkenylene, substituted or non-substituted aryl and arylalkyl constituted from a substituted or non-substituted aryl group and an alkylene group in which optional hydrogens may be substituted with fluorine and in which optional —$CH_2$— may be substituted with —O— or —CH=CH—; $R^2$ and $R^3$ are groups independently selected from alkyl having a carbon atom number of 1 to 8, phenyl and cyclohexyl; and $A^2$ is a group represented by Formula (2-2-1):

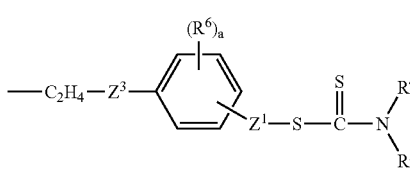
(2-2-1)

wherein $Z^1$ is alkylene having a carbon atom number of 1 to 3 in which optional —$CH_2$— may be substituted with —O—; $Z^3$ is a single bond or alkylene having a carbon atom number of 1 to 8 in which optional —$CH_2$— may be substituted with —O—, —COO— or —OCO—; $R^4$ and $R^5$ are independently hydrogen, alkyl having a carbon atom number of 1 to 12, cycloalkyl having a carbon atom number of 5 to 10 or aryl having a carbon atom number of 6 to 10, and $R^4$ and $R^5$ may be combined with each other to form a ring together with N; $R^6$ is alkyl having a carbon atom number of 1 to 3; a is an integer of 0 to 2; and a bonding position of $Z^1$ on a benzene ring is a meta position or a para position to a bonding position of $Z^3$, and a bonding position of $R^6$ is an optional position excluding the respective bonding positions of $Z^1$ and $Z^3$;

<step (d)> a step in which a compound represented by Formula (6-1) is reacted with a compound represented by Formula (7) to obtain a compound represented by Formula (6-2):

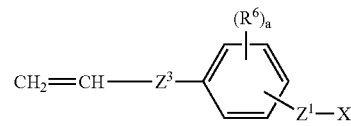
(6-1)

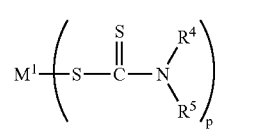
(7)

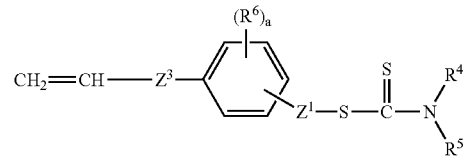
(6-2)

wherein $Z^1$, $Z^3$, $R^6$, a, $R^4$ and $R^5$ in the above formulas have the same meanings as those of these codes in Formula (2-2-1); the bonding positions of $Z^1$ and $R^6$ on a benzene ring are the same as these bonding positions in Formula (2-2-1); X is halogen; $M^1$ is a metal element of the first group or the second group in the periodic table; and p is the same value as an atomic value of $M^1$;

<step (h)> a step in which the compound represented by Formula (6-2) is reacted with a compound represented by Formula (4) in the presence of a transition metal catalyst to obtain a silicon compound represented by Formula (8-2);

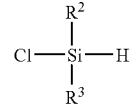
(4)

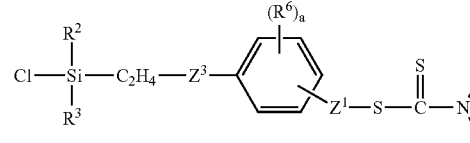
(8-2)

wherein $R^2$ and $R^3$ in the above formulas have the same meanings as those of these codes in Formula (1-2); the other codes have the same meanings as those of these codes in Formula (2-2-1); and the bonding positions of $Z^1$ and $R^6$ on a benzene ring are the same as these bonding positions in Formula (2-2-1);

<step (i)> a step in which the compound represented by Formula (8-2) is reacted with a compound represented by Formula (3-1) or a compound represented by Formula (3-2) to obtain the compound represented by Formula (1-2):

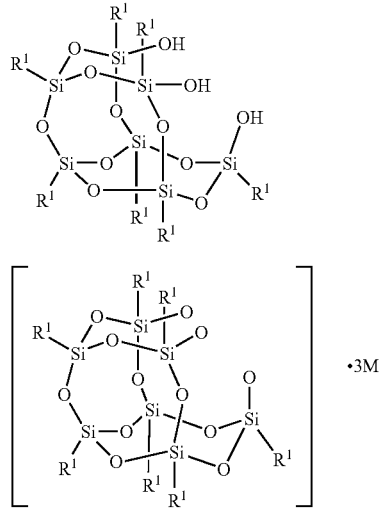

(3-1)

(3-2)

wherein in the above formulas, $R^1$ has the same meaning as that of $R^1$ in Formula (1-2); and M is a monovalent alkali metal atom.

[37] The production process as described in the item [36], wherein all $R^1$'s are the same group selected from alkyl having a carbon atom number of 1 to 8 in which optional hydrogens may be substituted with fluorine and in which optional —$CH_2$— may be substituted with —O—, —CH=CH—, cycloalkylene or cycloalkenylene, phenyl in which optional hydrogens may be substituted with halogen, methyl or methoxy, non-substituted naphthyl and phenylalkyl constituted from a phenyl group in which optional hydrogens may be substituted with fluorine, alkyl having a carbon atom number of 1 to 4, vinyl or methoxy and an alkylene group in which optional —$CH_2$— may be substituted with —O—; and $R^2$ and $R^3$ are groups independently selected from alkyl having a carbon atom number of 1 to 8, phenyl and cyclohexyl.

[38] The production process as described in the item [36], wherein all $R^1$'s are the same group selected from ethyl, 3,3,3-trifluoropropyl, 2-methylpropyl, 2,4,4-trimethylpentyl, tridecafluoro-1,1,2,2-tetrahydrooctyl, cyclopentyl, cyclohexyl and phenyl; and $R^2$ and $R^3$ are methyl.

[39] A production process for a silicon compound represented by Formula (1-3) characterized by reacting a compound represented by Formula (9) with a compound represented by Formula (10):

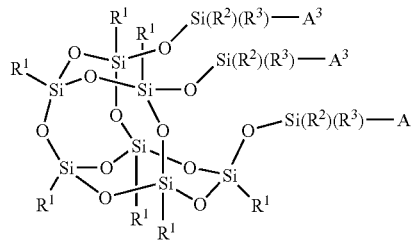

(1-3)

wherein respective $R^1$'s are groups independently selected from hydrogen, alkyl having a carbon atom number of 1 to 40 in which optional hydrogens may be substituted with fluorine and in which optional —$CH_2$— may be substituted with —O—, —CH=CH—, cycloalkylene or cycloalkenylene, substituted or non-substituted aryl and arylalkyl constituted from a substituted or non-substituted aryl group and an alkylene group in which optional hydrogens may be substituted with fluorine and in which optional —$CH_2$— may be substituted with —O— or —CH=CH—; $R^2$ and $R^3$ are groups independently selected from alkyl having a carbon atom number of 1 to 8, phenyl and cyclohexyl; and $A^3$ is a group represented by Formula (2-3):

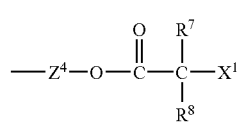

(2-3)

wherein $Z^4$ is alkylene having a carbon atom number of 2 to 20 or alkenylene having a carbon atom number of 3 to 8, and optional —$CH_2$— in these alkylene and alkenylene may be substituted with —O—; $R^7$ is hydrogen, alkyl having a carbon atom number of 1 to 20, aryl having a carbon atom number of 6 to 20 or arylalkyl having a carbon atom number of 7 to 20; $R^8$ is alkyl having a carbon atom number of 1 to 20, aryl having a carbon atom number of 6 to 20 or arylalkyl having a carbon atom number of 7 to 20; and $X^1$ is halogen;

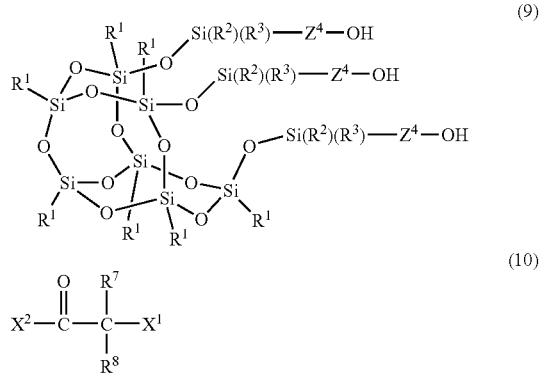

(9)

(10)

wherein $R^1$, $R^2$, $R^3$ and $Z^4$ in Formula (9) have the same meanings as those of these codes in Formula (1-3); in Formula (10), $R^7$, $R^8$ and $X^1$ have the same meanings as those of these codes in Formula (2-3); and $X^2$ is halogen.

[40] The production process as described in the item [39], wherein all $R^1$'s are the same group selected from alkyl having a carbon atom number of 1 to 8 in which optional hydrogens may be substituted with fluorine and in which optional —$CH_2$— may be substituted with —O—, —CH=CH—, cycloalkylene or cycloalkenylene, phenyl in which optional hydrogens may be substituted with halogen, methyl or methoxy, non-substituted naphthyl and phenylalkyl constituted from a phenyl group in which optional hydrogens may be substituted with fluorine, alkyl having a carbon atom number of 1 to 4, vinyl or methoxy and an alkylene group in which optional —$CH_2$— may be substituted with —O—; and $R^2$ and $R^3$ are groups independently selected from alkyl having a carbon atom number of 1 to 8, phenyl and cyclohexyl.

[41] The production process as described in the item [39], wherein all $R^1$'s are the same group selected from ethyl, 3,3,3-trifluoropropyl, 2-methylpropyl, 2,4,4-trimethylpentyl, tridecafluoro-1,1,2,2-tetrahydrooctyl, cyclopentyl, cyclohexyl and phenyl; and $R^2$ and $R^3$ are methyl.

[42] A polymer obtained by polymerizing an addition-polymerizable monomer using the silicon compound as described in the item [1] as an initiator and using a transition metal complex as a catalyst.

[43] A polymer obtained by polymerizing an addition-polymerizable monomer using the silicon compound as described in the item [3] as an initiator and using a transition metal complex as a catalyst.

[44] A polymer represented by Formula (P-1):

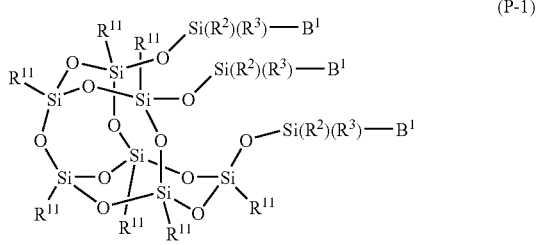

(P-1)

wherein all $R^{11}$'s are the same group selected from alkyl having a carbon atom number of 1 to 8 in which optional hydrogens may be substituted with fluorine and in which optional —$CH_2$— may be substituted with —O—, —CH=CH—, cycloalkylene or cycloalkenylene, phenyl in which optional hydrogens may be substituted with halogen, methyl or methoxy, non-substituted naphthyl and phenylalkyl constituted from a phenyl group in which optional hydrogens may be substituted with fluorine, alkyl having a carbon atom number of 1 to 4, vinyl or methoxy and an alkylene group in which optional —$CH_2$— may be substituted with —O—; $R^2$ and $R^3$ are groups independently selected from alkyl having a carbon atom number of 1 to 8, phenyl and cyclohexyl; and $B^1$ is a group represented by Formula (2-1-P):

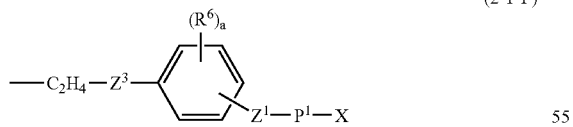

(2-1-P)

wherein $Z^1$ is alkylene having a carbon atom number of 1 to 3 in which optional —$CH_2$— may be substituted with —O—; $Z^3$ is a single bond or alkylene having a carbon atom number of 1 to 8 in which optional —$CH_2$— may be substituted with —O—, —COO— or —OCO—; $R^6$ is alkyl having a carbon atom number of 1 to 3; a is an integer of 0 to 2; X is halogen; a bonding position of $Z^1$ on a benzene ring is a meta position or a para position to a bonding position of $Z^3$, and a bonding position of $R^6$ is an optional position excluding the respective bonding positions of $Z^1$ and $Z^3$; and $P^1$ is a chain of a structural unit obtained by polymerizing an addition-polymerizable monomer.

[45] A polymer represented by Formula (P-2):

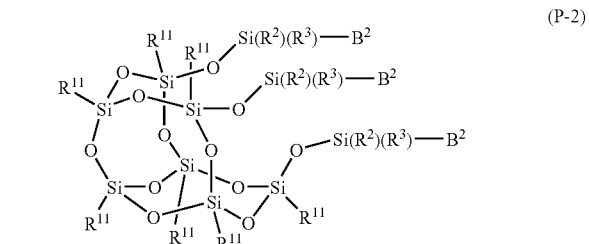

(P-2)

wherein all $R^{11}$'s are the same group selected from alkyl having a carbon atom number of 1 to 8 in which optional hydrogens may be substituted with fluorine and in which optional —$CH_2$— may be substituted with —O—, —CH=CH—, cycloalkylene or cycloalkenylene, phenyl in which optional hydrogens may be substituted with halogen, methyl or methoxy, non-substituted naphthyl and phenylalkyl constituted from a phenyl group in which optional hydrogens may be substituted with fluorine, alkyl having a carbon atom number of 1 to 4, vinyl or methoxy and an alkylene group in which optional —$CH_2$— may be substituted with —O—; $R^2$ and $R^3$ are groups independently selected from alkyl having a carbon atom number of 1 to 8, phenyl and cyclohexyl; and B2 is a group represented by Formula (2-2-P):

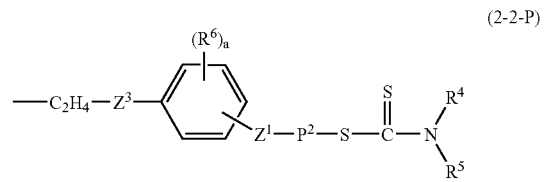

(2-2-P)

wherein $Z^1$ is alkylene having a carbon atom number of 1 to 3 in which optional —$CH_2$— may be substituted with —O—; $Z^3$ is a single bond or alkylene having a carbon atom number of 1 to 8 in which optional —$CH_2$— may be substituted with —O—, —COO— or —OCO—; $R^4$ and $R^5$ are independently hydrogen, alkyl having a carbon atom number of 1 to 12, cycloalkyl having a carbon atom number of 5 to 10 or aryl having a carbon atom number of 6 to 10, and $R^4$ and $R^5$ may be combined with each other to form a ring together with N; $R^6$ is alkyl having a carbon atom number of 1 to 3; a is an integer of 0 to 2; a bonding position of $Z^1$ on a benzene ring is a meta position or a para position to a bonding position of $Z^3$, and a bonding position of $R^6$ is an optional position excluding the respective bonding positions of $Z^1$ and $Z^3$; and $P^2$ is a chain of a structural unit obtained by polymerizing an addition-polymerizable monomer.

[46] A polymer represented by Formula (P-3):

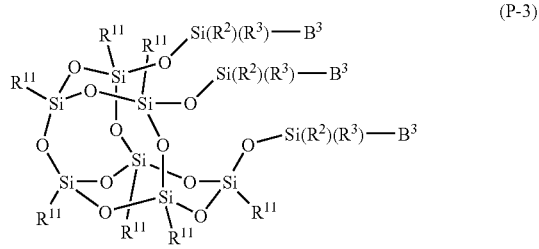

(P-3)

wherein all $R^{11}$'s are the same group selected from alkyl having a carbon atom number of 1 to 8 in which optional hydrogens may be substituted with fluorine and in which optional —$CH_2$— may be substituted with —O—, —CH=CH—, cycloalkylene or cycloalkenylene, phenyl in which optional hydrogens may be substituted with halogen, methyl or methoxy, non-substituted naphthyl and phenylalkyl constituted from a phenyl group in which optional hydrogens may be substituted with fluorine, alkyl having a carbon atom number of 1 to 4, vinyl or methoxy and an alkylene group in which optional —$CH_2$— may be substituted with —O—; $R^2$ and $R^3$ are groups independently selected from alkyl having a carbon atom number of 1 to 8, phenyl and cyclohexyl; and $B^3$ is a group represented by Formula (2-3-P):

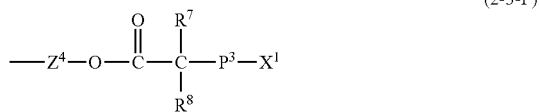

(2-3-P)

wherein $Z^4$ is alkylene having a carbon atom number of 2 to 20 or alkenylene having a carbon atom number of 3 to 8, and optional —$CH_2$— in these alkylene and alkenylene may be substituted with —O—; $R^7$ is hydrogen, alkyl having a carbon atom number of 1 to 20, aryl having a carbon atom number of 6 to 20 or arylalkyl having a carbon atom number of 7 to 20; $R^8$ is alkyl having a carbon atom number of 1 to 20, aryl having a carbon atom number of 6 to 20 or arylalkyl having a carbon atom number of 7 to 20; $X^1$ is halogen; and $p^3$ is a chain of a structural unit obtained by polymerizing an addition-polymerizable monomer.

[47] The polymer as described in the item [44], wherein the addition-polymerizable monomer is at least one selected from the group of (meth)acrylic acid derivatives and the group of styrene derivatives.

[48] The polymer as described in the item [45], wherein the addition-polymerizable monomer is at least one selected from the group of (meth)acrylic acid derivatives and the group of styrene derivatives.

[49] The polymer as described in the item [46], wherein the addition-polymerizable monomer is at least one selected from the group of (meth)acrylic acid derivatives and the group of styrene derivatives.

First, terms used in the present invention shall be explained. Optional means that not only the position but also the number can optionally be selected, but it does not include the case where the number is 0. When it is described that "optional —$CH_2$— may be substituted with —O—", a case where plural continuous —$CH_2$— are substituted with —O— is not included therein. For example, alkyl in which optional —$CH_2$— may be substituted with —O— or —CH=CH— includes alkyl, alkoxy, alkoxyalkyl, alkenyl, alkyloxyalkenyl and alkenyloxyalkyl. Both of alkyl and alkylene may be either a linear group or a branched group. This shall be applied to a case where optional —$CH_2$— is substituted with other divalent group. For example, any of alkyl, alkenylene, alkenyl and alkylene in alkyloxyalkenyl and alkenyloxyalkyl each described above may be either a linear group or a branched group. Both of cycloalkyl and cycloalkenyl may be or may not be a cross-linked ring structure. A (meth)acrylic acid derivative is used as a general term for acrylic acid derivatives and methacrylic acid derivatives. (Meth)acrylate is used as a general term for acrylate and methacrylate. (Meth)acryloyloxy is used as a general term for acryloyloxy and methacryloyloxy.

The silicon compound of the present invention is represented by Formula (1). In the following explanations, the silicon compound represented by Formula (1) shall be described as the compound (1). Compounds represented by the other formulas shall be shown by the same abbreviation.

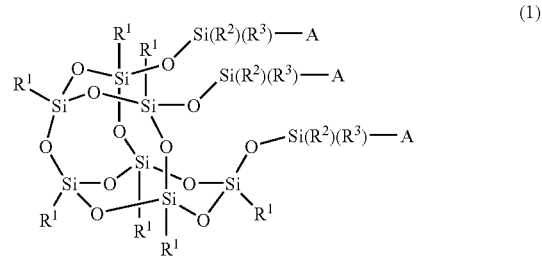

(1)

Respective $R^1$'s in Formula (1) are groups independently selected from hydrogen, alkyl, substituted or non-substituted aryl and substituted or non-substituted arylalkyl. All $R^1$'s are preferably the same one group but may be constituted from two or more different groups. The examples of a case where seven $R^1$'s are constituted from different groups are a case where they are constituted from two or more alkyls, a case where they are constituted from two or more aryls, a case where they are constituted from two or more arylalkyls, a case where they are constituted from hydrogen and at least one aryl, a case where they are constituted from at least one alkyl and at least one aryl, a case where they are constituted from at least one alkyl and at least one arylalkyl and a case where they are constituted from at least one aryl and at least one arylalkyl. They ma be combinations other than the above examples. The compound (1) having two or more different $R^1$'s can be obtained by using two or more raw materials in producing it. The raw materials shall be described later.

When $R^1$ is alkyl, it has a carbon atom number of 1 to 40. The preferred carbon atom number is 1 to 30. The more preferred carbon atom number is 1 to 8. Optional hydrogens thereof may be substituted with fluorine, and optional —$CH_2$— may be substituted with —O—, —CH=CH—, cycloalkylene or cycloalkenylene. The preferred examples of such alkyl are non-substituted alkyl having a carbon atom number of 1 to 30, alkoxyalkyl having a carbon atom number of 2 to 30, alkyl which has a carbon atom number of 1 to 8 and in which one —$CH_2$— is substituted with cycloalkylene, alkenyl having a carbon atom number of 2 to 20, alkenyloxyalkyl having a carbon atom number of 3 to 20, alkyloxyalkenyl having a carbon atom number of 3 to 20, alkyl which has a carbon atom number of 1 to 8 and in which one —$CH_2$— is substituted with cycloalkenylene and groups in which optional hydrogens in the above groups are substituted with fluorine. The preferred carbon atom number of cycloalkylene and cycloalkenylene is 3 to 8.

The examples of non-substituted alkyl having a carbon atom number of 1 to 30 are methyl, ethyl, propyl, 1-methylethyl, butyl, 2-methylpropyl, 1,1-dimethylethyl, pentyl, hexyl, 1,1,2-trimethylpropyl, heptyl, octyl, 2,4,4-trimethylpentyl, nonyl, decyl, undecyl, dodecyl, tetradecyl, hexadecyl, octadecyl, eicosyl, docosyl and triacontyl.

The examples of fluorinated alkyl having a carbon atom number of 1 to 30 are 2-fluoroethyl, 2,2-difluoroethyl, 3,3,3-trifluoropropyl, hexafluoropropyl, nonafluoro-1,1,2,2-tetrahydrohexyl, tridecafluoro-1,1,2,2-tetrahydrooctyl, heptadecafluoro-1,1,2,2-tetrahydrodecyl, perfluoro-1H,1H,2H,2H-dodecyl and perfluoro-1H,1H,2H,2H-tetradecyl.

The examples of alkoxyalkyl and fluorinated alkoxyalkyl each having a carbon atom number of 2 to 29 are 3-methoxypropyl, methoxyethoxyundecyl, 2-fluoroethyloxypropyl, 2,2,2-trifluoroethyloxypropyl, 2-fluoro-1-fluoromethylethyloxypropyl, 2,2,3,3-tetrafluoropropyloxypropyl, 2,2,3,3,3-pentafluoropropyloxypropyl, hexafluoroisopropyloxypropyl, heptafluoroisopropyloxypropyl, hexafluorobutyloxypropyl, heptafluorobutyloxypropyl, octafluoroisobutyloxypropyl, octafluoropentyloxypropyl, 2-fluoroethyloxybutyl, 2,2,2-trifluoroethyloxybutyl, 2-fluoro-1-fluoromethylethyloxybutyl, 2,2,3,3-tetrafluoropropyloxybutyl, 2,2,3,3,3-pentafluoropropyloxybutyl, hexafluoroisopropyloxybutyl, hexafluorobutyloxybutyl, heptafluorobutyloxybutyl, octafluoroisobutyloxybutyl, octafluoropentyloxybutyl, 2-fluoroethyloxyisobutyl, 2,2,2-trifluoroethyloxyisobutyl, 2-fluoro-1-fluoromethylethyloxyisobutyl, 2,2,3,3-tetrafluoropropyloxyisobutyl, 2,2,3,3,3-pentafluoropropyloxyisobutyl, hexafluoroisopropyloxyisobutyl, hexafluorobutyloxyisobutyl, heptafluorobutyloxyisobutyl, octafluoroisobutyloxyisobutyl and octafluoropentyloxyisobutyl.

The examples of alkyl, which has a carbon atom number of 1 to 8 and in which one —CH$_2$— is substituted with cycloalkylene are cyclohexylmethyl, adamantaneethyl, cyclopentyl, cyclohexyl, 2-bicycloheptyl and cyclooctyl. Cyclohexyl is an example in which —CH$_2$— in methyl is substituted with cyclohexylene. Cyclohexylmethyl is an example in which —CH$_2$— of αβ position in ethyl is substituted with cyclohexylene.

The examples of alkenyl having a carbon atom number of 2 to 20 are vinyl, 2-propenyl, 3-butenyl, 5-hexenyl, 7-octenyl, 10-undecenyl and 21-docosenyl. The example of alkenyloxyalkyl having a carbon atom number of 3 to 20 is allyloxyundecyl. The examples of alkyl which has a carbon atom number of 1 to 8 and in which one —CH$_2$— is substituted with cycloalkenylene are 2-(3-cyclohexenyl)ethyl, 5-(bicycloheptenyl)ethyl, 2-cyclopentenyl, 3-cyclohexenyl, 5-norbornene-2-yl and 4-cyclooctenyl.

The preferred examples of a case where $R^1$ in Formula (1) is substituted or non-substituted aryl are phenyl in which optional hydrogens may be substituted with halogen or alkyl having a carbon atom number of 1 to 10 and non-substituted naphthyl. The preferred examples of halogen are fluorine, chlorine and bromine. In alkyl which is a substituent of phenyl, optional hydrogens may be substituted with fluorine, and optional —CH$_2$— may be substituted with —O—, —CH═CH— or phenylene. That is, the more specific examples of the preferred aryl are phenyl, non-substituted naphthyl, alkylphenyl, alkyloxyphenyl, alkenylphenyl, phenyl having as a substituent, alkyl in which at least one —CH$_2$— is substituted with phenylene and groups in which optional hydrogens are substituted with halogen in the above groups. In the present invention, phenyl means non-substituted phenyl unless otherwise described.

The examples of halogenated phenyl are pentafluorophenyl, 4-chlorophenyl and 4-bromophenyl.

The examples of the alkylphenyl are 4-methylphenyl, 4-ethylphenyl, 4-propylphenyl, 4-butylphenyl, 4-pentylphenyl, 4-heptylphenyl, 4-octylphenyl, 4-nonylphenyl, 4-decylphenyl, 2,4-dimethylphenyl, 2,4,6-trimethylphenyl, 2,4,6-triethylphenyl, 4-(1-methylethyl)phenyl, 4-(1,1-dimethylethyl)phenyl, 4-(2-ethylhexyl)phenyl and 2,4,6-tris(1-methylethyl)phenyl.

The examples of alkyloxyphenyl are (4-methoxy)phenyl, (4-ethoxy)phenyl, (4-propoxy)phenyl, (4-butoxy)phenyl, (4-pentyloxy)phenyl, (4-heptyloxy)phenyl, (4-decyloxy)phenyl, (4-octadecyloxy)phenyl, 4-(1-methylethoxy)phenyl, 4-(2-methylpropoxy)phenyl and 4-(1,1-dimethylethoxy)phenyl. The examples of alkenylphenyl are 4-vinylphenyl, 4-(1-methylvinyl)phenyl and 4-(3-butenyl)phenyl.

The examples of phenyl having as a substituent, alkyl in which at least one —CH$_2$— is substituted with phenylene are 4-(2-phenylvinyl)phenyl, 4-phenoxyphenyl, 3-(phenylmethyl)phenyl, biphenyl and terphenyl. 4-(2-Phenylvinyl)phenyl is an example in which one —CH$_2$— in ethyl of ethylphenyl is substituted with phenylene and in which the other —CH$_2$— is substituted with —CH═CH—.

The examples of phenyl in which a part of hydrogens is substituted with halogen and in which the other hydrogens are substituted with alkyl, alkyloxy or alkenyl are 3-chloro-4-methylphenyl, 2,5-dichloro-4-methylphenyl, 3,5-dichloro-4-methylphenyl, 2,3,5-trichloro-4-methylphenyl, 2,3,6-trichloro-4-methylphenyl, 3-bromo-4-methylphenyl, 2,5-dibromo-4-methylphenyl, 3,5-dibromo-4-methylphenyl, 2,3-difluoro-4-methylphenyl, 3-chloro-4-methoxyphenyl, 3-bromo-4-methoxyphenyl, 3,5-dibromo-4-methoxyphenyl, 2,3-difluoro-4-methoxyphenyl, 2,3-difluoro-4-ethoxyphenyl, 2,3-difluoro-4-propoxyphenyl and 4-vinyl-2,3,5,6-tetrafluorophenyl.

Next, the examples of a case where $R^1$ in Formula (1) is substituted or non-substituted arylalkyl shall be given. In alkylene of the arylalkyl, optional hydrogens may be substituted with fluorine, and optional —CH$_2$— may be substituted with —O— or —CH═CH—. The preferred example of the arylalkyl is phenylalkyl. In this case, optional hydrogens of the phenyl may be-substituted with halogen or alkyl having a carbon atom number of 1 to 12. In the above alkyl, optional hydrogens may be substituted with fluorine, and optional —CH$_2$— may be substituted with —O—, —CH═CH—, cycloalkylene or phenylene. The preferred carbon number of the alkylene is 1 to 12, and the more preferred carbon number is 1 to 8.

The examples of non-substituted phenylalkyl are phenylmethyl, 2-phenylethyl, 3-phenylpropyl, 4-phenylbutyl, 5-phenylpentyl, 6-phenylhexyl, 11-phenylundecyl, 1-phenylethyl, 2-phenylpropyl, 1-methyl-2-phenylethyl, 1-phenylpropyl, 3-phenylbutyl, 1-methyl-3-phenylpropyl, 2-phenylbutyl, 2-methyl-2-phenylpropyl and 1-phenylhexyl.

The examples of phenylalkyl in which at least one hydrogen on phenyl is substituted with fluorine are 4-fluorophenylmethyl, 2,3,4,5,6-pentafluorophenylmethyl, 2-(2,3,4',5,6-pentafluorophenyl)ethyl, 3-(2,3,4,5,6-pentafluorophenyl)propyl, 2-(2-fluorophenyl)propyl and 2-(4-fluorophenyl)propyl.

The examples of phenylalkyl in which at least one hydrogen on phenyl is substituted with chlorine are 4-chlorophenylmethyl, 2-chlorophenylmethyl, 2,6-dichlorophenylmethyl, 2,4-dichlorophenylmethyl, 2,3,6- trichlorophenylmethyl, 2,4,6-trichlorophenylmethyl, 2,4,5-trichlorophenylmethyl, 2,3,4,6-tetrachlorophenylmethyl, 2,3,4,5,6-pentachlorophenylmethyl, 2-(2-chlorophenyl)ethyl, 2-(4-chlorophenyl)ethyl, 2-(2,4,5-chlorophenyl)ethyl, 2-(2,3,6-chlorophenyl)ethyl, 3-(3-chlorophenyl)propyl, 3-(4-chlorophenyl)propyl, 3-(2,4,5-trichlorophenyl)propyl, 3-(2,3,6-trichlorophenyl)propyl, 4-(2-chlorophenyl)butyl, 4-(3-chlorophenyl)butyl, 4-(4-chlorophenyl)butyl, 4-(2,3,6-trichlorophenyl)butyl, 4-(2,4,5-trichlorophenyl)butyl, 1-(3-chlorophenyl)ethyl, 1-(4-chlorophenyl)ethyl, 2-(4-chlorophenyl)propyl, 2-(2-chlorophenyl)propyl and 1-(4-chlorophenyl)butyl.

The examples of phenylalkyl in which at least one hydrogen on phenyl is substituted with bromine are 2-bromophenylmethyl, 4-bromophenylmethyl, 2,4-dibromophenylmethyl, 2,4,6-tribromophenylmethyl, 2,3,4,5-tetrabromophenylmethyl, 2,3,4,5,6-pentabromophenylmethyl, 2-(4-bromophenyl)ethyl, 3-(4-bromophenyl)propyl, 3-(3-bromophenyl)propyl, 4-(4-bromophenyl)butyl, 1-(4-bromophenyl)ethyl, 2-(2-bromophenyl)propyl and 2-(4-bromophenyl)propyl.

The examples of phenylalkyl in which at least one hydrogen on phenyl is substituted with alkyl having a carbon atom number of 1 to 12 are 2-methylphenylmethyl, 3-methylphenylmethyl, 4-methylphenylmethyl, 4-dodecylphenylmethyl, 3,5-dimethylphenylmethyl, 2-(4-methylphenyl)ethyl, 2-(3-methylphenyl)ethyl, 2-(2,5-dimethylphenyl)ethyl, 2-(4-ethylphenyl)ethyl, 2-(3-ethylphenyl)ethyl, 1-(4-methylphenyl)ethyl, 1-(3-methylphenyl)ethyl, 1-(2-methylphenyl)ethyl, 2-(4-methylphenyl)propyl, 2-(2-methylphenyl)propyl, 2-(4-ethylphenyl)propyl, 2-(2-ethylphenyl)propyl, 2-(2,3-dimethylphenyl)propyl, 2-(2,5-dimethylphenyl) propyl, 2-(3,5-dimethylphenyl)-propyl, 2-(2,4-dimethylphenyl)propyl, 2-(3,4-dimethylphenyl) propyl, 2-(2,5-dimethylphenyl) butyl, (4-(1-methylethyl)phenyl)methyl, 2-(4-(1,1-dimethylethyl)phenyl)ethyl, 2-(4-(1-methylethyl)phenyl)propyl and 2-(3-(1-methylethyl)phenyl)propyl.

The examples of phenylalkyl having as a substituent for phenyl, alkyl which has a carbon atom number of 1 to 12 and in which at least one hydrogen is substituted with fluorine are 3-(trifluoromethyl)phenylmethyl, 2-(4-trifluoromethylphenyl)ethyl, 2-(4-nonafluorobutylphenyl)ethyl, 2-(4-tridecafluorohexylphenyl)ethyl, 2-(4-heptadecafluorooctylphenyl)ethyl, 1-(3-trifluoromethylphenyl)ethyl, 1-(4-trifluoromethylphenyl)ethyl, 1-(4-nonafluorobutylphenyl)ethyl, 1-(4-tridecafluorohexylphenyl)ethyl, 1-(4-heptadecafluorooctylphenyl)ethyl, 2-(4-nonafluorobutylphenyl)propyl, 1-methyl-1-(4-nonafluorobutylphenyl)ethyl, 2-(4-tridecafluorohexylphenyl)propyl, 1-methyl-1-(4-tridecafluorohexylphenyl)ethyl, 2-(4-heptadecafluorooctylphenyl)propyl and 1-methyl-1-(4-heptadecafluorooctylphenyl)ethyl.

The examples of phenylalkyl having as a substituent for phenyl, alkyl which has a carbon atom number of 1 to 12 and in which one —$CH_2$— is substituted with —CH═CH— are 2-(4-vinylphenyl)ethyl, 1-(4-vinylphenyl)ethyl and 1-(2-(2-propenyl)phenyl)ethyl.

The examples of phenylalkyl having as a substituent for phenyl, alkyl which has a carbon atom number of 1 to 12 and in which one —$CH_2$— is substituted with —O— are 4-methoxyphenylmethyl, 3-methoxyphenylmethyl, 4-ethoxyphenylmethyl, 2-(4-methoxyphenyl)ethyl, 3-(4-methoxyphenyl)propyl, 3-(2-methoxyphenyl)propyl, 3-(3,4-dimethoxyphenyl)propyl, 11-(4-methoxyphenyl)undecyl, 1-(4-methoxyphenyl)ethyl, 2-(3-methoxymethyl)phenyl)ethyl and 3-(2-nonadecafluorodecenyloxyphenyl)propyl.

The examples of phenylalkyl having as a substituent for phenyl, alkyl having a carbon atom number of 1 to 12 in which one —$CH_2$— is substituted with cycloalkylene and in which another —$CH_2$— may be substituted with —O— are cyclopentylphenylmethyl, cyclopentyloxyphenylmethyl, cyclohexylphenylmethyl, cyclohexylphenylethyl, cyclohexylphenylpropyl and cyclohexyloxyphenylmethyl.

The examples of phenylalkyl having as a substituent for phenyl, alkyl having a carbon atom number of 1 to 12 in which one —$CH_2$— is substituted with phenylene and in which another —$CH_2$— may be substituted with —O— are 2-(4-phenoxyphenyl)ethyl, 2-(4-phenoxyphenyl)propyl, 2-(2-phenoxyphenyl)propyl, 4-biphenylylmethyl, 3-biphenylylethyl, 4-biphenylylethyl, 4-biphenylylpropyl, 2-(2-biphenylyl)propyl and 2-(4-biphenylyl)propyl.

The examples of phenylalkyl in which at least two hydrogens on phenyl are substituted with different groups are 3-(2,5-dimethoxy-(3,4,6-trimethylphenyl)propyl, 3-chloro-2-methylphenylmethyl, 4-chloro-2-methylphenylmethyl, 5-chloro-2-methylphenylmethyl, 6-chloro-2-methylphenylmethyl, 2-chloro-4-methylphenylmethyl, 3-chloro-4-methylphenylmethyl, 2,3-dichloro-4-methylphenylmethyl, 2,5-dichloro-4-methylphenylmethyl, 3,5-dichloro-4-methylphenylmethyl, 2,3,5-trichloro-4-methylphenylmethyl, 2,3,5,6-tetrachloro-4-methylphenylmethyl, (2,3,4,6-tetrachloro-5-methylphenyl)methyl, 2,3,4,5-tetrachloro-6-methylphenylmethyl, 4-chloro-3,5-dimethylphenylmethyl, 2-chloro-3,5-dimethylphenylmethyl, 2,4-dichloro-3,5-dimethylphenylmethyl, 2,6-dichloro-3,5-dimethylphenylmethyl, 2,4,6-trichloro-3,5-dimethylphenylmethyl, 3-bromo-2-methylphenylmethyl, 4-bromo-2-methylphenylmethyl, 5-bromo-2-methylphenylmethyl, 6-bromo-2-methylphenylmethyl, 3-bromo-4-methylphenylmethyl, 2,3-dibromo-4-methylphenylmethyl, 2,3,5-tribromo-4-methylphenylmethyl, 2,3,5,6-tetrabromo-4-methylphenylmethyl and 11-(3-chloro-4-methoxyphenyl)undecyl.

The most preferred examples of phenyl in the phenylalkyl are non-substituted phenyl and phenyl having at least one of fluorine, alkyl having a carbon atom number of 1 to 4, vinyl and methoxy as a substituent.

The examples of phenylalkyl in which at least one —$CH_2$— in alkylene constituting the phenylalkyl is substituted with —O— or —CH═CH— are 3-phenoxypropyl, 1-phenylvinyl, 2-phenylvinyl, 3-phenyl-2-propenyl, 4-phenyl-4-pentenyl and 13-phenyl-12-tridecenyl.

The examples of phenylalkenyl in which hydrogen on phenyl is substituted with fluorine or methyl are 4-fluorophenylvinyl, 2,3-difluorophenylvinyl, 2,3,4,5,6-pentafluorophenylvinyl and 4-methylphenylvinyl.

The more preferred examples of $R^1$ are ethyl, 2-fluoroethyl, 2,2-difluoroethyl, propyl, 3,3,3-trifluoropropyl, hexafluoropropyl, 2-methylpropyl, 2,4,4-trimethylpentyl, tridecafluoro-1,1,2,2-tetrahydrooctyl, cyclopentyl, cyclohexyl, phenyl, phenyl halide, methylphenyl, dimethylphenyl, methoxyphenyl, non-substituted naphthyl, phenylmethyl, phenylethyl, phenylbutyl, 2-phenylpropyl, 1-methyl-2-phenylethyl, pentafluorophenylpropyl, 4-ethylphenylethyl, 3-ethylphenylethyl, 4-(1,1-dimethylethyl)phenylethyl, 4-vinylphenylethyl, 1-(4-vinylphenyl)ethyl, 4-methoxyphenylpropyl and phenoxypropyl.

The particularly preferred examples of $R^1$ are ethyl, 3,3,3-trifluoropropyl, 2-methylpropyl, 2,4,4-trimethylpentyl, tridecafluoro-1,1,2,2-tetrahydrooctyl, cyclopentyl, cyclohexyl and phenyl. The most preferred examples of $R^1$ are phenyl and 3,3,3-trifluoropropyl.

$R^2$ and $R^3$ in Formula (1) are independently alkyl having a carbon atom number of 1 to 8, phenyl or cyclohexyl. The examples of the alkyl are methyl, ethyl, propyl, isopropyl, butyl, isobutyl, pentyl, 2-methylbutyl, hexyl, 2-methylpentyl, heptyl, 2-methylhexyl, octyl, 2-methylheptyl and 2-ethylhexyl. The most preferred alkyl is methyl.

A in Formula (1) is a group having a polymerization initiating ability, preferably a living radical polymerization initiating ability for a monomer. The examples of such A are a group having a haloalkylphenyl group, a group having MgBr, a group having a dithiocarbamate group and a group having an α-haloester group. The group having a haloalkylphenyl group generates a radical in the presence of a copper chloride/amine complex, and it is an initiator for cationic polymerization in the coexistence of silver perchlorate. The examples of the haloalkylphenyl group are chloromethylphenyl, bromomethylphenyl and iodomethylphenyl.

The MgBr group can be introduced in the following manner. First, a silsesquioxane derivative having a double bond such as a styryl group or a vinyl group is synthesized. Next, a borane-dimethyl sulfide complex is used to carry out hydroboration of a double bond part in the above derivative to prepare a silsesquioxane derivative having boron. Then, this silsesquioxane derivative having boron is reacted with pentane-1,5-diyl-di(magnesium bromide), whereby an MgBr group can be introduced. The silsesquioxane derivative of a Grignard type thus obtained can be used as an anionic polymerization initiator for styrene and methyl (meth)acrylate.

The more preferred examples of A are a group having haloalkylphenyl, a group having a dithiocarbamate group and a group having an α-haloester group.

An atom transfer radical polymerization method is known as a polymerization method using haloalkylpheny as a group for initiating radical polymerization. In this method, a metal complex comprising an 8th group, 9th group, 10th group or 11th group element in the periodic table as a central metal is used as a catalyst. In this atom transfer radical polymerization, it is known that haloalkylphenyl has an excellent polymerization initiating ability. Further, it is also well known that this polymerization is like living polymerization. That is, the silicon compound of the present invention having haloalkylphenyl has an excellent polymerization initiating ability in the presence of a transition metal catalyst and can continue to maintain a living polymerizability. It can initiate polymerization for all radically polymerizable monomers. In particular, it can reveal an excellent living polymerizability to styrene base derivatives. Haloalkylphenyl has a strong electrophilicity, and therefore an amino group, a hydroxyl group and a mercapto group can be introduced into the silicon compound of the present invention having haloalkylphenyl by making use of various nucleophilic reagents. That is, this silicon compound can efficiently be used as a useful intermediate.

The preferred examples of the silicon compound of the present invention having haloalkylphenyl is a compound represented by Formula (1-1):

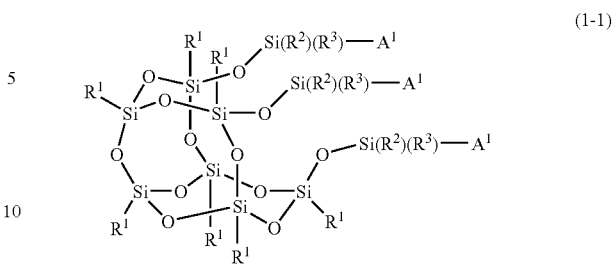

(1-1)

In Formula (1-1), $R^1$, $R^2$ and $R^3$ have the same meanings as those of these codes in Formula (1), and $A^1$ is a group represented by Formula (2-1):

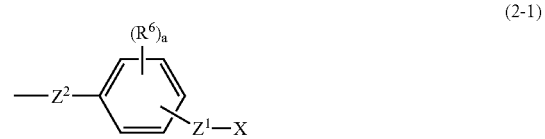

(2-1)

X in Formula (2-1) is halogen such as Cl, Br and I. Cl and Br are more preferred as an initiating group in atom transfer radical polymerization. $Z^1$ is alkylene having a carbon atom number of 1 to 3. The examples of $Z^1$ are methylene, 1,2-ethylene, 1,1-ethylene, 1,3-trimethylene, ethylmethylene, 1-methyl-1,2-ethylene and 2-methyl-1,2-ethylene. The preferred example of $Z^1$ is methylene. $Z^2$ is alkylene having a carbon atom number of 2 to 10. In this alkylene, one —$CH_2$— may be substituted with —O—. A bonding position of $Z^1$ on the benzene ring is a meta position or a para position to a bonding position of $Z^2$. $R^6$ is alkyl having 1 to 3 carbon atoms. The examples of $R^6$ are methyl, ethyl, propyl and isopropyl. Preferred $R^6$ is methyl. The term a showing the number of $R^6$ is 0, 1 or 2, and a is preferably 0. A bonding position of $R^6$ on the benzene ring is any position excluding the bonding positions of $Z^1$ and $Z^2$.

In bonding an organic group to an Si atom, representative methods for obtaining the derivative which is not hydrolyzed are a method in which a Grignard reagent is reacted with Si-halogen and a method in which a compound having an aliphatic unsaturated bond is reacted with Si—H. The latter is usually called hydrosilylation reaction. In the present invention, the hydrosilylation reaction is rather liable to be applied in terms of availability of the raw materials. That is, a preferred method for introducing a functional group into a silsesquioxane derivative is a method in which an Si—H functional silsesquioxane derivative is bonded to a compound having an unsaturated bond at a terminal by hydrosilylation reaction. Accordingly, the preferred example of $Z^2$ in Formula (2) is a group represented by $Z^3$—$C_2H_4$—.

That is, the preferred example of Formula (2-1) is Formula (2-1-1):

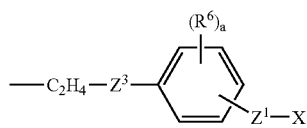
(2-1-1)

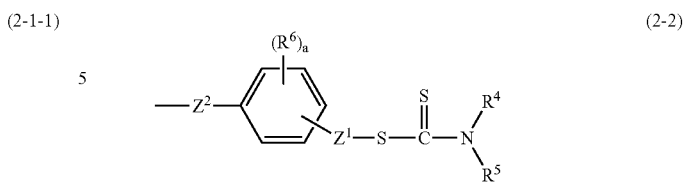
(2-2)

$Z^3$ in Formula (2-1-1) is a single bond or alkylene having a carbon atom number of 1 to 8. In these alkylenes, one —CH$_2$— may be substituted with —O—. That is, the preferred examples of $Z^2$ in Formula (2-1) are —C$_2$H$_4$—, —C$_3$H$_6$—, —OC$_2$H$_4$—, —OC$_3$H$_6$—, —CH$_2$OC$_2$H$_4$—, —CH$_2$OC$_3$H$_6$—, —C$_2$H$_4$OC$_2$H$_4$— and —C$_2$H$_4$OC$_3$H$_6$—. However, the selected range of $Z^2$ shall not be restricted to them. In Formula (2-1-1), codes other than $Z^3$ have the same meanings as those of the codes in Formula (2-1), and the bonding positions of $Z^1$ and $R^6$ on a benzene ring are the same as these bonding positions in Formula (2-1).

A photo initiator-transfer agent-terminator polymerization method is known as a photopolymerization method using a dithiocarbamate group as a polymerization initiating group. In this photo initiator-transfer agent-terminator polymerization, it is well known that a dithiocarbamate group is radically dissociated by virtue of light and that it has an excellent polymerization initiating ability and sensitizing ability. It is well known as well that this photopolymerization is like living polymerization. Accordingly, the silicon compound of the present invention having a dithiocarbamate group can continue to maintain a living polymerizability as long as it is irradiated with light, and it has a photopolymerization initiating ability for all radically polymerizable monomers. In particular, it can reveal an excellent living polymerizability to (met)acrylic acid derivatives. A dithiocarbamate group has a radiation resistance, a pharmacological activity such as a weeding effect, a complex-forming ability and a hydrophilicity in addition to the characteristics as a photopolymerization initiating group, and therefore it is possible to efficiently use these characteristics.

The preferred examples of the silicon compound of the present invention having a dithiocarbamate group is a compound represented by Formula (1-2):

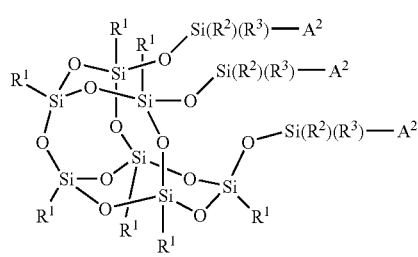
(1-2)

In Formula (1-2), $R^1$, $R^2$ and $R^3$ have the same meanings as those of these codes in Formula (1), and $A^2$ is a group represented by Formula (2-2):

$Z^1$, $Z^2$, $R^6$ and a in Formula (2-2) are defined in the same manner as in these codes in Formula (2-1), and the bonding positions of $Z^1$ and $R^6$ are defined as well in the same manner as in Formula (2-1). $R^4$ and $R^5$ are independently hydrogen, alkyl having a carbon atom number of 1 to 12, cycloalkyl having a carbon atom number of 5 to 10 or aryl having a carbon atom number of 6 to 10. The examples of $R^4$ or $R^5$ other than hydrogen are methyl, ethyl, propyl, isopropyl, butyl, isobutyl, pentyl, 2-methylbutyl, hexyl, 2-methylpentyl, heptyl, 2-methylhexyl, octyl, 2-methylheptyl, 2-ethylhexyl, decyl, phenyl, cyclopentyl and cyclohexyl. Both of $R^4$ and $R^5$ may be one of these groups or one of $R^4$ and $R^5$ may be one of these groups, and the other may be hydrogen.

$R^4$ and $R^5$ may be combined with each other to form a ring together with N. In this case, the examples of a dithiocarbamate group are N-cyclotrimethylenedithiocarbamate, N-cyclotetramethylenedithiocarbamate, N-cyclopentamethylenedithiocarbamate, N-cyclohexamethylenedithiocarbamate, N-cycloheptamethylenedithiocarbamate and N-cyclooctamethylenedithiocarbamate. The preferred dithiocarbamate groups are N,N-dimethyldithiocarbamate, N,N-diethyldithiocarbamate, N-methyldithiocarbamate and N-ethyldithiocarbamate. N,N-diethyldithiocarbamate is most preferred.

$Z^2$ in Formula (2-2) is preferably a group represented by $Z^3$-C$_2$H$_4$ as is the case with Formula (2-1). That is, the preferred example of Formula (2-2) is Formula (2-2-1):

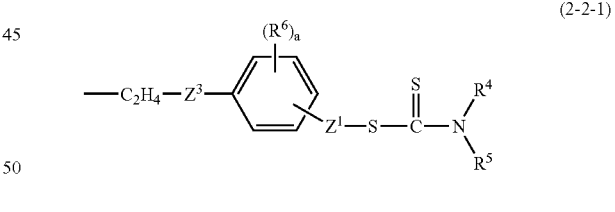
(2-2-1)

In Formula (2-2-1), $Z^3$ is defined in the same manner as in $Z^3$ in Formula (2-1-1), and the codes other than $Z^3$ have the same meanings as those of these codes in Formula (2-2). The bonding positions of $Z^1$ and $R^6$ on a benzene ring are the same as these bond positions in Formula (2-2).

The group having an α-haloester group means a group having α-halocarbonyloxy at an end. An atom transfer radical polymerization method is known as a polymerization method using the above α-halocarbonyloxy as a group for initiating radical polymerization. A polymerization catalyst used in the above method is a metal complex comprising an 8th group, 9th group, 10th group or 11th group element in the periodic table as a central metal atom. In this atom transfer radical polymerization, it is known that a group having α-halocarbonyloxy has an excellent polymerization initiating ability. It is well known as well that this polymerization is like living polymerization. That is, the silicon compound of the present invention having an α-haloester group has an excellent polymerization initiating ability in the presence of a transition metal complex and can continue to maintain a living polymerizability. It can initiate polymerization for all radically polymerizable monomers. In particular, it can reveal an excellent living polymerizability to (meth)acrylic acid derivatives or styrene base derivatives.

The silicon compound of the present invention having an α-haloester group has an α-halocarbonyloxy group at an end, and therefore it can be derived into a lot of derivatives by applying various organic reactions. For example, it can be derived into a silsesquioxane derivative having an organic metal functional group by reacting the above silicon compound with lithium, magnesium or zinc. To be specific, the silicon compound of the present invention having an α-haloester group is reacted with zinc to be derived into a silsesquioxane derivative having an organic zinc functional group, and then aldehyde and ketone are added thereto, whereby it can be converted into alcohols. Accordingly, the silsesquioxane derivative having an organic zinc functional group is useful as an intermediate raw material used for a so-called Reformatsky reaction.

An α-halocarbonyloxy group has a strong electrophilicity, and therefore it can be converted into an amino group and a mercapto group using various nucleophilic reagents. Further, an α-halocarbonyloxy group is treated with enamine to be converted into an imine salt, and this imine salt is hydrolyzed, whereby it can be converted into ketone. That is, the silicon compound of the present invention having an α-halocarbonyloxy group is also useful as an intermediate raw material used for a Stork Enamine Reaction. Silsesquioxane derivatives having various organic functional groups and polymerizable functional groups can be prepared as well by reacting the above silicon compound with aliphatic and aromatic Grignard reagents. Accordingly, the silicon compound of the present invention having an α-halocarbonyloxy group can be used not only as a polymerization initiator but also as an intermediate useful for various organic syntheses.

The preferred example of the silicon compound of the present invention having an α-haloester group is a compound represented by Formula (1-3):

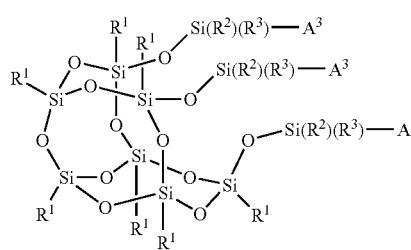

(1-3)

In Formula (1-3), $R^1$, $R^2$ and $R^3$ have the same meanings as those of these codes in Formula (1), and $A^3$ is a group represented by Formula (2-3):

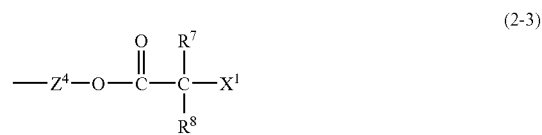

(2-3)

$X^1$ in the above formula is halogen, and the examples thereof are chlorine, bromine and iodine. Chlorine and bromine are most preferred as an initiating group for atom transfer radical polymerization. $R^7$ is hydrogen, alkyl having a carbon atom number of 1 to 20, aryl having a carbon atom number of 6 to 20 or arylalkyl having a carbon atom number of 7 to 20. The preferred examples of $R^7$ are hydrogen, alkyl having a carbon atom number of 1 to 20, phenyl in which optional hydrogens may be substituted with alkyl having a carbon atom number of 1 to 14 and phenylalkyl constituted from a phenyl group in which optional hydrogens may be substituted with alkyl having a carbon atom number of 1 to 14 and an alkylene group having a carbon atom number of 1 to 14, wherein the total number of carbon atoms in the above groups is 7 to 20. The more preferred examples of $R^7$ are hydrogen and alkyl having a carbon atom number of 1 to 20. The further preferred examples of $R^7$ are hydrogen, methyl and ethyl, and the most preferred example is methyl. $R^8$ is alkyl having a carbon atom number of 1 to 20, aryl having a carbon atom number of 6 to 20 or arylalkyl having a carbon atom number of 7 to 20. The preferred examples of $R^8$ are alkyl having a carbon atom number of 1 to 20, phenyl in which optional hydrogens may be substituted with alkyl having a carbon atom number of 1 to 14 and phenylalkyl constituted from a phenyl group in which optional hydrogens may be substituted with alkyl having a carbon atom number of 1 to 14 and an alkylene group having a carbon atom number of 1 to 14, wherein the total number of carbon atoms in the above groups is 7 to 20. The more preferred example of $R^8$ is alkyl having a carbon atom number of 1 to 20. The further preferred examples of $R^8$ are methyl and ethyl, and the most preferred example is methyl. $Z^4$ is alkylene having a carbon atom number of 2 to 20 or alkenylene having a carbon atom number of 3 to 8. Optional —$CH_2$— in these alkylene and alkenylene may be substituted with —O—. The preferred example of $Z^4$ is alkylene which has a carbon atom number of 2 to 10 and in which optional —$CH_2$— may be substituted with —O—. The examples of such alkylene are —$C_2H_4$—, —$C_3H_6$—, —$C_4H_8$—, —$C_5H_6$—, —$C_2H_4$—O—$C_3H_6$— and —$C_3H_6$—O—$C_3H_6$—. The more preferred examples of $Z^4$ are —$C_3H_6$—, —$C_4H_8$—, —$C_5H_{10}$— and —$C_2H_4$—O—$C_3H_6$—.

Next, a part of the specific examples of the compound (1-1) and the compound (1-2) among the silicon compounds of the present invention shall be shown in Tables 2 to 4 using codes shown in Table 1. These examples are the examples of a case where in the following Formula (1-1-1) and Formula (1-2-1), $R^1$ is ethyl, 2-methylpropyl, 2,4,4-trimethylpentyl, cyclopentyl or phenyl and where $Z^3$ is a single bond, —$CH_2$—, —$C_2H_4$— or a group in which one —$CH_2$— in these alkylene is substituted with —COO—.

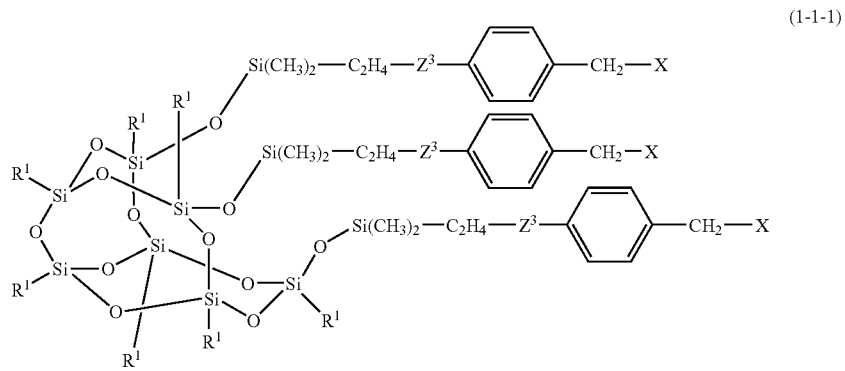
(1-1-1)
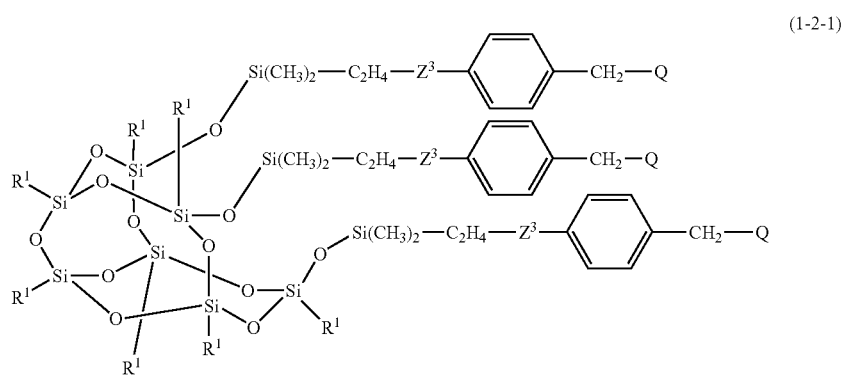
(1-2-1)
TABLE 1
| Code | Chemical Formula |
|---|---|
| Et | —$C_2H_5$ |
| iBu | —$CH_2CH(CH_3)_2$ |
| iOc | —$CH_2CH(CH_3)CH_2C(CH_3)_3$ |
| CP | cyclopentyl |
| B | phenyl |
| Ph | 1,4-phenylene |
| — | Single Bond |
TABLE 1-continued
| Code | Chemical Formula |
|---|---|
| C1 | —$CH_2$— |
| C2 | —$C_2H_4$— |
| C3 | —$C_3H_6$— |
| C4 | —$C_4H_8$— |
| CL | —Cl |
| BR | —Br |
| DM | —Si(CH$_3$)$_2$— |
| Q | $C_2H_5$, $C_3H_5$ N—C(=S)—S— |

TABLE 2

| No. | R¹ | Z³ | X | Formula (1-1-1) |
|---|---|---|---|---|
| 1 | Et | — | CL | (Et—)₇(CL—C1—Ph—C2-DM—)₃Si₇O₁₂ |
| 2 | iBu | — | CL | (iBu—)₇(CL—C1—Ph—C2-DM—)₃Si₇O₁₂ |
| 3 | iOc | — | CL | (iOc—)₇(CL—C1—Ph—C2-DM—)₃Si₇O₁₂ |
| 4 | CP | — | CL | (CP—)₇(CL—C1—Ph—C2-DM—)₃Si₇O₁₂ |
| 5 | B | — | CL | (B—)₇(CL—C1—Ph—C2-DM—)₃Si₇O₁₂ |
| 6 | Et | C1 | CL | (Et—)₇(CL—C1—Ph—C3-DM—)₃Si₇O₁₂ |
| 7 | iBu | C1 | CL | (iBu—)₇(CL—C1—Ph—C3-DM—)₃Si₇O₁₂ |
| 8 | iOc | C1 | CL | (iOc—)₇(CL—C1—Ph—C3-DM—)₃Si₇O₁₂ |
| 9 | CP | C1 | CL | (CP—)₇(CL—C1—Ph—C3-DM—)₃Si₇O₁₂ |
| 10 | B | C1 | CL | (B—)₇(CL—C1—Ph—C3-DM—)₃Si₇O₁₂ |
| 11 | Et | C2 | CL | (Et—)₇(CL—C1—Ph—C4-DM—)₃Si₇O₁₂ |
| 12 | iBu | C2 | CL | (iBu—)₇(CL—C1—Ph—C4-DM—)₃Si₇O₁₂ |
| 13 | iOc | C2 | CL | (iOc—)₇(CL—C1—Ph—C4-DM—)₃Si₇O₁₂ |
| 14 | CP | C2 | CL | (CP—)₇(CL—C1—Ph—C4-DM—)₃Si₇O₁₂ |
| 15 | B | C2 | CL | (B—)₇(CL—C1—Ph—C4-DM—)₃Si₇O₁₂ |
| 16 | Et | COO | CL | (Et—)₇(CL—C1—Ph—COO—C2-DM—)₃Si₇O₁₂ |
| 17 | iBu | COO | CL | (iBu—)₇(CL—C1—Ph—COO—C2-DM—)₃Si₇O₁₂ |
| 18 | iOc | COO | CL | (iOc—)₇(CL—C1—Ph—COO—C2-DM—)₃Si₇O₁₂ |
| 19 | CP | COO | CL | (CP—)₇(CL—C1—Ph—COO—C2-DM—)₃Si₇O₁₂ |
| 20 | B | COO | CL | (B—)₇(CL—C1—Ph—COO—C2-DM—)₃Si₇O₁₂ |
| 21 | Et | COO—C1 | CL | (Et—)₇(CL—C1—Ph—COO—C3-DM—)₃Si₇O₁₂ |
| 22 | iBu | COO—C1 | CL | (iBu—)₇(CL—C1—Ph—COO—C3-DM—)₃Si₇O₁₂ |
| 23 | iOc | COO—C1 | CL | (iOc—)₇(CL—C1—Ph—COO—C3-DM—)₃Si₇O₁₂ |
| 24 | CP | COO—C1 | CL | (CP—)₇(CL—C1—Ph—COO—C3-DM—)₃Si₇O₁₂ |
| 25 | B | COO—C1 | CL | (B—)₇(CL—C1—Ph—COO—C3-DM—)₃Si₇O₁₂ |

TABLE 3

| No. | R¹ | Z³ | X | Formula (1-1-1) |
|---|---|---|---|---|
| 1 | Et | — | BR | (Et—)₇(BR-C1—Ph—C2-DM—)₃Si₇O₁₂ |
| 2 | iBu | — | BR | (iBu—)₇(BR-C1—Ph—C2-DM—)₃Si₇O₁₂ |
| 3 | iOc | — | BR | (iOc—)₇(BR-C1—Ph—C2-DM—)₃Si₇O₁₂ |
| 4 | CP | — | BR | (CP—)₇(BR-C1—Ph—C2-DM—)₃Si₇O₁₂ |
| 5 | B | — | BR | (B—)₇(BR-C1—Ph—C2-DM—)₃Si₇O₁₂ |
| 6 | Et | C1 | BR | (Et—)₇(BR-C1—Ph—C3-DM—)₃Si₇O₁₂ |
| 7 | iBu | C1 | BR | (iBu—)₇(BR-C1—Ph—C3-DM—)₃Si₇O₁₂ |
| 8 | iOc | C1 | BR | (iOc—)₇(BR-C1—Ph—C3-DM—)₃Si₇O₁₂ |
| 9 | CP | C1 | BR | (CP—)₇(BR-C1—Ph—C3-DM—)₃Si₇O₁₂ |
| 10 | B | C1 | BR | (B—)₇(BR-C1—Ph—C3-DM—)₃Si₇O₁₂ |
| 11 | Et | C2 | BR | (Et—)₇(BR-C1—Ph—C4-DM—)₃Si₇O₁₂ |
| 12 | iBu | C2 | BR | (iBu—)₇(BR-C1—Ph—C4-DM—)₃Si₇O₁₂ |
| 13 | iOc | C2 | BR | (iOc—)₇(BR-C1—Ph—C4-DM—)₃Si₇O₁₂ |
| 14 | CP | C2 | BR | (CP—)₇(BR-C1—Ph—C4-DM—)₃Si₇O₁₂ |
| 15 | B | C2 | BR | (B—)₇(BR-C1—Ph—C4-DM—)₃Si₇O₁₂ |
| 16 | Et | COO | BR | (Et—)₇(BR-C1—Ph—COO—C2-DM—)₃Si₇O₁₂ |
| 17 | iBu | COO | BR | (iBu—)₇(BR-C1—Ph—COO—C2-DM—)₃Si₇O₁₂ |
| 18 | iOc | COO | BR | (iOc—)₇(BR-C1—Ph—COO—C2-DM—)₃Si₇O₁₂ |
| 19 | CP | COO | BR | (CP—)₇(BR-C1—Ph—COO—C2-DM—)₃Si₇O₁₂ |
| 20 | B | COO | BR | (B—)₇(BR-C1—Ph—COO—C2-DM—)₃Si₇O₁₂ |
| 21 | Et | COO—C1 | BR | (Et—)₇(BR-C1—Ph—COO—C3-DM—)₃Si₇O₁₂ |
| 22 | iBu | COO—C1 | BR | (iBu—)₇(BR-C1—Ph—COO—C3-DM—)₃Si₇O₁₂ |
| 23 | iOc | COO—C1 | BR | (iOc—)₇(BR-C1—Ph—COO—C3-DM—)₃Si₇O₁₂ |
| 24 | CP | COO—C1 | BR | (CP—)₇(BR-C1—Ph—COO—C3-DM—)₃Si₇O₁₂ |
| 25 | B | COO—C1 | BR | (B—)₇(BR-C1—Ph—COO—C3-DM—)₃Si₇O₁₂ |

TABLE 4

| No. | R¹ | Z³ | Formula (1-2-1) |
|---|---|---|---|
| 1 | Et | — | (Et—)₇(Q-C1—Ph—C2-DM—)₃Si₇O₁₂ |
| 2 | iBu | — | (iBu—)₇(Q-C1—Ph—C2-DM—)₃Si₇O₁₂ |
| 3 | iOc | — | (iOc—)₇(Q-C1—Ph—C2-DM—)₃Si₇O₁₂ |
| 4 | CP | — | (CP—)₇(Q-C1—Ph—C2-DM—)₃Si₇O₁₂ |
| 5 | B | — | (B—)₇(Q-C1—Ph—C2-DM—)₃Si₇O₁₂ |
| 6 | Et | C1 | (Et—)₇(Q-C1—Ph—C3-DM—)₃Si₇O₁₂ |
| 7 | iBu | C1 | (iBu—)₇(Q-C1—Ph—C3-DM—)₃Si₇O₁₂ |
| 8 | iOc | C1 | (iOc—)₇(Q-C1—Ph—C3-DM—)₃Si₇O₁₂ |
| 9 | CP | C1 | (CP—)₇(Q-C1—Ph—C3-DM—)₃Si₇O₁₂ |
| 10 | B | C1 | (B—)₇(Q-C1—Ph—C3-DM—)₃Si₇O₁₂ |
| 11 | Et | C2 | (Et—)₇(Q-C1—Ph—C4-DM—)₃Si₇O₁₂ |
| 12 | iBu | C2 | (iBu—)₇(Q-C1—Ph—C4-DM—)₃Si₇O₁₂ |

TABLE 4-continued

| No. | $R^1$ | $Z^3$ | Formula (1-2-1) |
|---|---|---|---|
| 13 | iOc | C2 | (iOc—)$_7$(Q-C1—Ph—C4-DM—)$_3$Si$_7$O$_{12}$ |
| 14 | CP | C2 | (CP—)$_7$(Q-C1—Ph—C4-DM—)$_3$Si$_7$O$_{12}$ |
| 15 | B | C2 | (B—)$_7$(Q-C1—Ph—C4-DM—)$_3$Si$_7$O$_{12}$ |
| 16 | Et | COO | (Et—)$_7$(Q-C1—Ph—COO—C2-DM—)$_3$Si$_7$O$_{12}$ |
| 17 | iBu | COO | (iBu—)$_7$(Q-C1—Ph—COO—C2-DM—)$_3$Si$_7$O$_{12}$ |
| 18 | iOc | COO | (iOc—)$_7$(Q-C1—Ph—COO—C2-DM—)$_3$Si$_7$O$_{12}$ |
| 19 | CP | COO | (CP—)$_7$(Q-C1—Ph—COO—C2-DM—)$_3$Si$_7$O$_{12}$ |
| 20 | B | COO | (B—)$_7$(Q-C1—Ph—COO—C2-DM—)$_3$Si$_7$O$_{12}$ |
| 21 | Et | COO—C1 | (Et—)$_7$(Q-C1—Ph—COO—C3-DM—)$_3$Si$_7$O$_{12}$ |
| 22 | iBu | COO—C1 | (iBu—)$_7$(Q-C1—Ph—COO—C3-DM—)$_3$Si$_7$O$_{12}$ |
| 23 | iOc | COO—C1 | (iOc—)$_7$(Q-C1—Ph—COO—C3-DM—)$_3$Si$_7$O$_{12}$ |
| 24 | CP | COO—C1 | (CP—)$_7$(Q-C1—Ph—COO—C3-DM—)$_3$Si$_7$O$_{12}$ |
| 25 | B | COO—C1 | (B—)$_7$(Q-C1—Ph—COO—C3-DM—)$_3$Si$_7$O$_{12}$ |

The examples shown in Table 2 to Table 4 are the preferred examples of the silicon compounds of the present invention. However, these examples shall not restrict the scope of the silicon compound of the present invention. Preferred as well are, for example, the compounds in which $R^1$ described above is a fluorine-containing group such as 3,3,3-trifluoropropyl and tridecafluoro-1,1,2,2-tetrahydrooctyl. Among the examples described above, the compound in which $R^1$ is phenyl is most preferred.

Next, a part of the specific examples of the compound (1-3) among the silicon compounds of the present invention shall be shown in Tables 6 to 13 using codes shown in Table 5. These examples are the examples of a case where in the following Formula (1-3-1), $R^{11}$ is ethyl, 2-methylpropyl, 2,4,4-trimethylpentyl, cyclopentyl, cyclohexyl, 3,3,3-trifluoropropyl or phenyl and where $Z^4$ is —(CH$_2$)$_3$—, —(CH$_2$)$_4$—, —(CH$_2$)$_5$— or —C$_2$H$_4$—O—C$_3$H$_6$—. These examples are the preferred examples of the silicon compound of the present invention. The compound in which $R^{11}$ is 3,3,3-trifluoropropyl or phenyl is the most preferred.

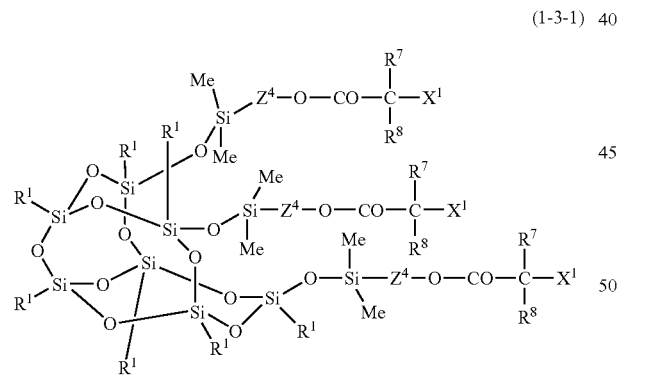

(1-3-1)

TABLE 5

| Code | Chemical Formula |
|---|---|
| Me | —CH$_3$ |
| Et | —C$_2$H$_5$ |
| IBu | —CH$_2$CH(CH$_3$)$_2$ |
| IOc | —CH$_2$CH(CH$_3$)CH$_2$C(CH$_3$)$_3$ |
| CPe | (cyclopentyl) |
| CHe | (cyclohexyl) |
| Ph | (1,4-phenylene) |
| TFPr | —CH$_2$CH$_2$CF$_3$ |
| DM | —Si(CH$_3$)$_2$— |
| C3 | —C$_3$H$_6$— |
| C4 | —C$_4$H$_8$— |
| C5 | —C$_5$H$_{10}$— |
| C2OC3 | —C$_2$H$_4$—O—C$_3$H$_6$— |
| CL | —Cl |
| BR | —Br |

TABLE 6

| No. | $R^{11}$ | $Z^4$ | $R^7$ | $R^8$ | $X^1$ | Formula (1-3-1) |
|---|---|---|---|---|---|---|
| 1 | Et | C3 | H | Me | CL | (Et—)$_7$(CL—CHMe—OCO—C3-DM—)$_3$Si$_7$O$_{12}$ |
| 2 | IBu | C3 | H | Me | CL | (IBu—)$_7$(CL—CHMe—OCO—C3-DM—)$_3$Si$_7$O$_{12}$ |
| 3 | IOc | C3 | H | Me | CL | (IOc—)$_7$(CL—CHMe—OCO—C3-DM—)$_3$Si$_7$O$_{12}$ |
| 4 | CPe | C3 | H | Me | CL | (CPe—)$_7$(CL—CHMe—OCO—C3-DM—)$_3$Si$_7$O$_{12}$ |
| 5 | CHe | C3 | H | Me | CL | (CHe—)$_7$(CL—CHMe—OCO—C3-DM—)$_3$Si$_7$O$_{12}$ |
| 6 | Ph | C3 | H | Me | CL | (Ph—)$_7$(CL—CHMe—OCO—C3-DM—)$_3$Si$_7$O$_{12}$ |
| 7 | TFPr | C3 | H | Me | CL | (TFPr—)$_7$(CL—CHMe—OCO—C3-DM—)$_3$Si$_7$O$_{12}$ |

TABLE 6-continued

| No. | $R^{11}$ | $Z^4$ | $R^7$ | $R^8$ | $X^1$ | Formula (1-3-1) |
|---|---|---|---|---|---|---|
| 8 | Et | C4 | H | Me | CL | (Et—)$_7$(CL—CHMe—OCO—C4-DM—)$_3$Si$_7$O$_{12}$ |
| 9 | IBu | C4 | H | Me | CL | (IBu—)$_7$(CL—CHMe—OCO—C4-DM—)$_3$Si$_7$O$_{12}$ |
| 10 | IOc | C4 | H | Me | CL | (IOc—)$_7$(CL—CHMe—OCO—C4-DM—)$_3$Si$_7$O$_{12}$ |
| 11 | CPe | C4 | H | Me | CL | (CPe—)$_7$(CL—CHMe—OCO—C4-DM—)$_3$Si$_7$O$_{12}$ |
| 12 | CHe | C4 | H | Me | CL | (CHe—)$_7$(CL—CHMe—OCO—C4-DM—)$_3$Si$_7$O$_{12}$ |
| 13 | Ph | C4 | H | Me | CL | (Ph—)$_7$(CL—CHMe—OCO—C4-DM—)$_3$Si$_7$O$_{12}$ |
| 14 | TFPr | C4 | H | Me | CL | (TFPr—)$_7$(CL—CHMe—OCO—C4-DM—)$_3$Si$_7$O$_{12}$ |
| 15 | Et | C5 | H | Me | CL | (Et—)$_7$(CL—CHMe—OCO—C5-DM—)$_3$Si$_7$O$_{12}$ |
| 16 | IBu | C5 | H | Me | CL | (IBu—)$_7$(CL—CHMe—OCO—C5-DM—)$_3$Si$_7$O$_{12}$ |
| 17 | IOc | C5 | H | Me | CL | (IOc—)$_7$(CL—CHMe—OCO—C5-DM—)$_3$Si$_7$O$_{12}$ |
| 18 | CPe | C5 | H | Me | CL | (CPe—)$_7$(CL—CHMe—OCO—C5-DM—)$_3$Si$_7$O$_{12}$ |
| 19 | CHe | C5 | H | Me | CL | (CHe—)$_7$(CL—CHMe—OCO—C5-DM—)$_3$Si$_7$O$_{12}$ |
| 20 | Ph | C5 | H | Me | CL | (Ph—)$_7$(CL—CHMe—OCO—C5-DM—)$_3$Si$_7$O$_{12}$ |
| 21 | TFPr | C5 | H | Me | CL | (TFPr—)$_7$(CL—CHMe—OCO—C5-DM—)$_3$Si$_7$O$_{12}$ |

TABLE 7

| No. | $R^{11}$ | $Z^4$ | $R^7$ | $R^8$ | $X^1$ | Formula (1-3-1) |
|---|---|---|---|---|---|---|
| 22 | Et | C2OC3 | H | Me | CL | (Et—)$_7$(CL—CHMe—OCO—C2OC3-DM—)$_3$Si$_7$O$_{12}$ |
| 23 | IBu | C2OC3 | H | Me | CL | (IBu—)$_7$(CL—CHMe—OCO—C2OC3-DM—)$_3$Si$_7$O$_{12}$ |
| 24 | IOc | C2OC3 | H | Me | CL | (IOc—)$_7$(CL—CHMe—OCO—C2OC3-DM—)$_3$Si$_7$O$_{12}$ |
| 25 | CPe | C2OC3 | H | Me | CL | (CPe—)$_7$(CL—CHMe—OCO—C2OC3-DM—)$_3$Si$_7$O$_{12}$ |
| 26 | CHe | C2OC3 | H | Me | CL | (CHe—)$_7$(CL—CHMe—OCO—C2OC3-DM—)$_3$Si$_7$O$_{12}$ |
| 27 | Ph | C2OC3 | H | Me | CL | (Ph—)$_7$(CL—CHMe—OCO—C2OC3-DM—)$_3$Si$_7$O$_{12}$ |
| 28 | TFPr | C2OC3 | H | Me | CL | (TFPr—)$_7$(CL—CHMe—OCO—C2OC3-DM—)$_3$Si$_7$O$_{12}$ |
| 29 | Et | C3 | Me | Me | CL | (Et—)$_7$(CL—CMe$_2$—OCO—C3-DM—)$_3$Si$_7$O$_{12}$ |
| 30 | IBu | C3 | Me | Me | CL | (IBu—)$_7$(CL—CMe$_2$—OCO—C3-DM—)$_3$Si$_7$O$_{12}$ |
| 31 | IOc | C3 | Me | Me | CL | (IOc—)$_7$(CL—CMe$_2$—OCO—C3-DM—)$_3$Si$_7$O$_{12}$ |
| 32 | CPe | C3 | Me | Me | CL | (CPe—)$_7$(CL—CMe$_2$—OCO—C3-DM—)$_3$Si$_7$O$_{12}$ |
| 33 | CHe | C3 | Me | Me | CL | (CHe—)$_7$(CL—CMe$_2$—OCO—C3-DM—)$_3$Si$_7$O$_{12}$ |
| 34 | Ph | C3 | Me | Me | CL | (Ph—)$_7$(CL—CMe$_2$—OCO—C3-DM—)$_3$Si$_7$O$_{12}$ |
| 35 | TFPr | C3 | Me | Me | CL | (TFPr—)$_7$(CL—CMe$_2$—OCO—C3-DM—)$_3$Si$_7$O$_{12}$ |
| 36 | Et | C4 | Me | Me | CL | (Et—)$_7$(CL—CMe$_2$—OCO—C4-DM—)$_3$Si$_7$O$_{12}$ |
| 37 | IBu | C4 | Me | Me | CL | (IBu—)$_7$(CL—CMe$_2$—OCO—C4-DM—)$_3$Si$_7$O$_{12}$ |
| 38 | IOc | C4 | Me | Me | CL | (IOc—)$_7$(CL—CMe$_2$—OCO—C4-DM—)$_3$Si$_7$O$_{12}$ |
| 39 | CPe | C4 | Me | Me | CL | (CPe—)$_7$(CL—CMe$_2$—OCO—C4-DM—)$_3$Si$_7$O$_{12}$ |
| 40 | CHe | C4 | Me | Me | CL | (CHe—)$_7$(CL—CMe$_2$—OCO—C4-DM—)$_3$Si$_7$O$_{12}$ |
| 41 | Ph | C4 | Me | Me | CL | (Ph—)$_7$(CL—CMe$_2$—OCO—C4-DM—)$_3$Si$_7$O$_{12}$ |
| 42 | TFPr | C4 | Me | Me | CL | (TFPr—)$_7$(CL—CMe$_2$—OCO—C4-DM—)$_3$Si$_7$O$_{12}$ |

TABLE 8

| No. | $R^{11}$ | $Z^4$ | $R^7$ | $R^8$ | $X^1$ | Formula (1-3-1) |
|---|---|---|---|---|---|---|
| 43 | Et | C5 | Me | Me | CL | (Et—)$_7$(CL—CMe$_2$—OCO—C5-DM—)$_3$Si$_7$O$_{12}$ |
| 44 | IBu | C5 | Me | Me | CL | (IBu—)$_7$(CL—CMe$_2$—OCO—C5-DM—)$_3$Si$_7$O$_{12}$ |
| 45 | IOc | C5 | Me | Me | CL | (IOc—)$_7$(CL—CMe$_2$—OCO—C5-DM—)$_3$Si$_7$O$_{12}$ |
| 46 | CPe | C5 | Me | Me | CL | (CPe—)$_7$(CL—CMe$_2$—OCO—C5-DM—)$_3$Si$_7$O$_{12}$ |
| 47 | CHe | C5 | Me | Me | CL | (CHe—)$_7$(CL—CMe$_2$—OCO—C5-DM—)$_3$Si$_7$O$_{12}$ |
| 48 | Ph | C5 | Me | Me | CL | (Ph—)$_7$(CL—CMe$_2$—OCO—C5-DM—)$_3$Si$_7$O$_{12}$ |
| 49 | TFPr | C5 | Me | Me | CL | (TFPr—)$_7$(CL—CMe$_2$—OCO—C5-DM—)$_3$Si$_7$O$_{12}$ |
| 50 | Et | C2OC3 | Me | Me | CL | (Et—)$_7$(CL—CMe$_2$—OCO—C2OC3-DM—)$_3$Si$_7$O$_{12}$ |
| 51 | IBu | C2OC3 | Me | Me | CL | (IBu—)$_7$(CL—CMe$_2$—OCO—C2OC3-DM—)$_3$Si$_7$O$_{12}$ |
| 52 | IOc | C2OC3 | Me | Me | CL | (IOc—)$_7$(CL—CMe$_2$—OCO—C2OC3-DM—)$_3$Si$_7$O$_{12}$ |
| 53 | CPe | C2OC3 | Me | Me | CL | (CPe—)$_7$(CL—CMe$_2$—OCO—C2OC3-DM—)$_3$Si$_7$O$_{12}$ |
| 54 | CHe | C2OC3 | Me | Me | CL | (CHe—)$_7$(CL—CMe$_2$—OCO—C2OC3-DM—)$_3$Si$_7$O$_{12}$ |
| 55 | Ph | C2OC3 | Me | Me | CL | (Ph—)$_7$(CL—CMe$_2$—OCO—C2OC3-DM—)$_3$Si$_7$O$_{12}$ |
| 56 | TFPr | C2OC3 | Me | Me | CL | (TFPr—)$_7$(CL—CMe$_2$—OCO—C2OC3-DM—)$_3$Si$_7$O$_{12}$ |
| 57 | Et | C3 | Et | Et | CL | (Et—)$_7$(CL—CEt$_2$—OCO—C3-DM—)$_3$Si$_7$O$_{12}$ |
| 58 | IBu | C3 | Et | Et | CL | (IBu—)$_7$(CL—CEt$_2$—OCO—C3-DM—)$_3$Si$_7$O$_{12}$ |
| 59 | IOc | C3 | Et | Et | CL | (IOc—)$_7$(CL—CEt$_2$—OCO—C3-DM—)$_3$Si$_7$O$_{12}$ |
| 60 | CPe | C3 | Et | Et | CL | (CPe—)$_7$(CL—CEt$_2$—OCO—C3-DM—)$_3$Si$_7$O$_{12}$ |
| 61 | CHe | C3 | Et | Et | CL | (CHe—)$_7$(CL—CEt$_2$—OCO—C3-DM—)$_3$Si$_7$O$_{12}$ |
| 62 | Ph | C3 | Et | Et | CL | (Ph—)$_7$(CL—CEt$_2$—OCO—C3-DM—)$_3$Si$_7$O$_{12}$ |
| 63 | TFPr | C3 | Et | Et | CL | (TFPr—)$_7$(CL—CEt$_2$—OCO—C3-DM—)$_3$Si$_7$O$_{12}$ |

TABLE 9

| No. | $R^{11}$ | $Z^4$ | $R^7$ | $R^8$ | $X^1$ | Formula (1-3-1) |
|---|---|---|---|---|---|---|
| 64 | Et | C4 | Et | Et | CL | (Et—)$_7$(CL—CEt$_2$—OCO—C4-DM—)$_3$Si$_7$O$_{12}$ |
| 65 | IBu | C4 | Et | Et | CL | (IBu—)$_7$(CL—CEt$_2$—OCO—C4-DM—)$_3$Si$_7$O$_{12}$ |
| 66 | IOc | C4 | Et | Et | CL | (IOc—)$_7$(CL—CEt$_2$—OCO—C4-DM—)$_3$Si$_7$O$_{12}$ |
| 67 | CPe | C4 | Et | Et | CL | (CPe—)$_7$(CL—CEt$_2$—OCO—C4-DM—)$_3$Si$_7$O$_{12}$ |
| 68 | CHe | C4 | Et | Et | CL | (CHe—)$_7$(CL—CEt$_2$—OCO—C4-DM—)$_3$Si$_7$O$_{12}$ |
| 69 | Ph | C4 | Et | Et | CL | (Ph—)$_7$(CL—CEt$_2$—OCO—C4-DM—)$_3$Si$_7$O$_{12}$ |
| 70 | TFPr | C4 | Et | Et | CL | (TFPr—)$_7$(CL—CEt$_2$—OCO—C4-DM—)$_3$Si$_7$O$_{12}$ |
| 71 | Et | C5 | Et | Et | CL | (Et—)$_7$(CL—CEt$_2$—OCO—C5-DM—)$_3$Si$_7$O$_{12}$ |
| 72 | IBu | C5 | Et | Et | CL | (IBu—)$_7$(CL—CEt$_2$—OCO—C5-DM—)$_3$Si$_7$O$_{12}$ |
| 73 | IOc | C5 | Et | Et | CL | (IOc—)$_7$(CL—CEt$_2$—OCO—C5-DM—)$_3$Si$_7$O$_{12}$ |
| 74 | CPe | C5 | Et | Et | CL | (CPe—)$_7$(CL—CEt$_2$—OCO—C5-DM—)$_3$Si$_7$O$_{12}$ |
| 75 | CHe | C5 | Et | Et | CL | (CHe—)$_7$(CL—CEt$_2$—OCO—C5-DM—)$_3$Si$_7$O$_{12}$ |
| 76 | Ph | C5 | Et | Et | CL | (Ph—)$_7$(CL—CEt$_2$—OCO—C5-DM—)$_3$Si$_7$O$_{12}$ |
| 77 | TFPr | C5 | Et | Et | CL | (TFPr—)$_7$(CL—CEt$_2$—OCO—C5-DM—)$_3$Si$_7$O$_{12}$ |
| 78 | Et | C2OC3 | Et | Et | CL | (Et—)$_7$(CL—CEt$_2$—OCO—C2OC3-DM—)$_3$Si$_7$O$_{12}$ |
| 79 | IBu | C2OC3 | Et | Et | CL | (IBu—)$_7$(CL—CEt$_2$—OCO—C2OC3-DM—)$_3$Si$_7$O$_{12}$ |
| 80 | IOc | C2OC3 | Et | Et | CL | (IOc—)$_7$(CL—CEt$_2$—OCO—C2OC3-DM—)$_3$Si$_7$O$_{12}$ |
| 81 | CPe | C2OC3 | Et | Et | CL | (CPe—)$_7$(CL—CEt$_2$—OCO—C2OC3-DM—)$_3$Si$_7$O$_{12}$ |
| 82 | CHe | C2OC3 | Et | Et | CL | (CHe—)$_7$(CL—CEt$_2$—OCO—C2OC3-DM—)$_3$Si$_7$O$_{12}$ |
| 83 | Ph | C2OC3 | Et | Et | CL | (Ph—)$_7$(CL—CEt$_2$—OCO—C2OC3-DM—)$_3$Si$_7$O$_{12}$ |
| 84 | TFPr | C2OC3 | Et | Et | CL | (TFPr—)$_7$(CL—CEt$_2$—OCO—C2OC3-DM—)$_3$Si$_7$O$_{12}$ |

TABLE 10

| No. | $R^{11}$ | $Z^4$ | $R^7$ | $R^8$ | $X^1$ | Formula (1-3-1) |
|---|---|---|---|---|---|---|
| 85 | Et | C3 | H | Me | BR | (Et—)$_7$(BR-CHMe—OCO—C3-DM—)$_3$Si$_7$O$_{12}$ |
| 86 | IBu | C3 | H | Me | BR | (IBu—)$_7$(BRCL—CHMe—OCO—C3-DM—)$_3$Si$_7$O$_{12}$ |
| 87 | IOc | C3 | H | Me | BR | (IOc—)$_7$(BR-CHMe—OCO—C3-DM—)$_3$Si$_7$O$_{12}$ |
| 88 | CPe | C3 | H | Me | BR | (CPe—)$_7$(BR-CHMe—OCO—C3-DM—)$_3$Si$_7$O$_{12}$ |
| 89 | CHe | C3 | H | Me | BR | (CHe—)$_7$(BR-CHMe—OCO—C3-DM—)$_3$Si$_7$O$_{12}$ |
| 90 | Ph | C3 | H | Me | BR | (Ph—)$_7$(BR-CHMe—OCO—C3-DM—)$_3$Si$_7$O$_{12}$ |
| 91 | TFPr | C3 | H | Me | BR | (TFPr—)$_7$(BR-CHMe—OCO—C3-DM—)$_3$Si$_7$O$_{12}$ |
| 92 | Et | C4 | H | Me | BR | (Et—)$_7$(BR-CHMe—OCO—C4-DM—)$_3$Si$_7$O$_{12}$ |
| 93 | IBu | C4 | H | Me | BR | (IBu—)$_7$(BR-CHMe—OCO—C4-DM—)$_3$Si$_7$O$_{12}$ |
| 94 | IOc | C4 | H | Me | BR | (IOc—)$_7$(BR-CHMe—OCO—C4-DM—)$_3$Si$_7$O$_{12}$ |
| 95 | CPe | C4 | H | Me | BR | (CPe—)$_7$(BR-CHMe—OCO—C4-DM—)$_3$Si$_7$O$_{12}$ |
| 96 | CHe | C4 | H | Me | BR | (CHe—)$_7$(BR-CHMe—OCO—C4-DM—)$_3$Si$_7$O$_{12}$ |
| 97 | Ph | C4 | H | Me | BR | (Ph—)$_7$(BR-CHMe—OCO—C4-DM—)$_3$Si$_7$O$_{12}$ |
| 98 | TFPr | C4 | H | Me | BR | (TFPr—)$_7$(BR-CHMe—OCO—C4-DM—)$_3$Si$_7$O$_{12}$ |
| 99 | Et | C5 | H | Me | BR | (Et—)$_7$(BR-CHMe—OCO—C5-DM—)$_3$Si$_7$O$_{12}$ |
| 100 | IBu | C5 | H | Me | BR | (IBu—)$_7$(BR-CHMe—OCO—C5-DM—)$_3$Si$_7$O$_{12}$ |
| 101 | IOc | C5 | H | Me | BR | (IOc—)$_7$(BR-CHMe—OCO—C5-DM—)$_3$Si$_7$O$_{12}$ |
| 102 | CPe | C5 | H | Me | BR | (CPe—)$_7$(BR-CHMe—OCO—C5-DM—)$_3$Si$_7$O$_{12}$ |
| 103 | CHe | C5 | H | Me | BR | (CHe—)$_7$(BR-CHMe—OCO—C5-DM—)$_3$Si$_7$O$_{12}$ |
| 104 | Ph | C5 | H | Me | BR | (Ph—)$_7$(BR-CHMe—OCO—C5-DM—)$_3$Si$_7$O$_{12}$ |
| 105 | TFPr | C5 | H | Me | BR | (TFPr—)$_7$(BR-CHMe—OCO—C5-DM—)$_3$Si$_7$O$_{12}$ |

TABLE 11

| No. | $R^{11}$ | $Z^4$ | $R^7$ | $R^8$ | $X^1$ | Formula (1-3-1) |
|---|---|---|---|---|---|---|
| 106 | Et | C2OC3 | H | Me | BR | (Et—)$_7$(BR-CHMe—OCO—C2OC3-DM—)$_3$Si$_7$O$_{12}$ |
| 107 | IBu | C2OC3 | H | Me | BR | (IBu—)$_7$(BR-CHMe—OCO—C2OC3-DM—)$_3$Si$_7$O$_{12}$ |
| 108 | IOc | C2OC3 | H | Me | BR | (IOc—)$_7$(BR-CHMe—OCO—C2OC3-DM—)$_3$Si$_7$O$_{12}$ |
| 109 | CPe | C2OC3 | H | Me | BR | (CPe—)$_7$(BR-CHMe—OCO—C2OC3-DM—)$_3$Si$_7$O$_{12}$ |
| 110 | CHe | C2OC3 | H | Me | BR | (CHe—)$_7$(BR-CHMe—OCO—C2OC3-DM—)$_3$Si$_7$O$_{12}$ |
| 111 | Ph | C2OC3 | H | Me | BR | (Ph—)$_7$(BR-CHMe—OCO—C2OC3-DM—)$_3$Si$_7$O$_{12}$ |
| 112 | TFPr | C2OC3 | H | Me | BR | (TFPr—)$_7$(BR-CHMe—OCO—C2OC3-DM—)$_3$Si$_7$O$_{12}$ |
| 113 | Et | C3 | Me | Me | BR | (Et—)$_7$(BR-CMe$_2$—OCO—C3-DM—)$_3$Si$_7$O$_{12}$ |
| 114 | IBu | C3 | Me | Me | BR | (IBu—)$_7$(BR-CMe$_2$—OCO—C3-DM—)$_3$Si$_7$O$_{12}$ |
| 115 | IOc | C3 | Me | Me | BR | (IOc—)$_7$(BR-CMe$_2$—OCO—C3-DM—)$_3$Si$_7$O$_{12}$ |
| 116 | CPe | C3 | Me | Me | BR | (CPe—)$_7$(BR-CMe$_2$—OCO—C3-DM—)$_3$Si$_7$O$_{12}$ |
| 117 | CHe | C3 | Me | Me | BR | (CHe—)$_7$(BR-CMe$_2$—OCO—C3-DM—)$_3$Si$_7$O$_{12}$ |
| 118 | Ph | C3 | Me | Me | BR | (Ph—)$_7$(BR-CMe$_2$—OCO—C3-DM—)$_3$Si$_7$O$_{12}$ |
| 119 | TFPr | C3 | Me | Me | BR | (TFPr—)$_7$(BR-CMe$_2$—OCO—C3-DM—)$_3$Si$_7$O$_{12}$ |
| 120 | Et | C4 | Me | Me | BR | (Et—)$_7$(BR-CMe$_2$—OCO—C4-DM—)$_3$Si$_7$O$_{12}$ |
| 121 | IBu | C4 | Me | Me | BR | (IBu—)$_7$(BR-CMe$_2$—OCO—C4-DM—)$_3$Si$_7$O$_{12}$ |
| 122 | IOc | C4 | Me | Me | BR | (IOc—)$_7$(BR-CMe$_2$—OCO—C4-DM—)$_3$Si$_7$O$_{12}$ |
| 123 | CPe | C4 | Me | Me | BR | (CPe—)$_7$(BR-CMe$_2$—OCO—C4-DM—)$_3$Si$_7$O$_{12}$ |

TABLE 11-continued

| No. | $R^{11}$ | $Z^4$ | $R^7$ | $R^8$ | $X^1$ | Formula (1-3-1) |
|---|---|---|---|---|---|---|
| 124 | CHe | C4 | Me | Me | BR | (CHe—)$_7$(BR-CMe$_2$—OCO—C4-DM—)$_3$Si$_7$O$_{12}$ |
| 125 | Ph | C4 | Me | Me | BR | (Ph—)$_7$(BR-CMe$_2$—OCO—C4-DM—)$_3$Si$_7$O$_{12}$ |
| 126 | TFPr | C4 | Me | Me | BR | (TFPr—)$_7$(BR-CMe$_2$—OCO—C4-DM—)$_3$Si$_7$O$_{12}$ |

TABLE 12

| No. | $R^{11}$ | $Z^4$ | $R^7$ | $R^8$ | $X^1$ | Formula (1-3-1) |
|---|---|---|---|---|---|---|
| 127 | Et | C5 | Me | Me | BR | (Et—)$_7$(BR-CMe$_2$—OCO—C5-DM—)$_3$Si$_7$O$_{12}$ |
| 128 | IBu | C5 | Me | Me | BR | (IBu—)$_7$(BR-CMe$_2$—OCO—C5-DM—)$_3$Si$_7$O$_{12}$ |
| 129 | IOc | C5 | Me | Me | BR | (IOc—)$_7$(BR-CMe$_2$—OCO—C5-DM—)$_3$Si$_7$O$_{12}$ |
| 130 | CPe | C5 | Me | Me | BR | (CPe—)$_7$(BR-CMe$_2$—OCO—C5-DM—)$_3$Si$_7$O$_{12}$ |
| 131 | CHe | C5 | Me | Me | BR | (CHe—)$_7$(BR-CMe$_2$—OCO—C5-DM—)$_3$Si$_7$O$_{12}$ |
| 132 | Ph | C5 | Me | Me | BR | (Ph—)$_7$(BR-CMe$_2$—OCO—C5-DM—)$_3$Si$_7$O$_{12}$ |
| 133 | TFPr | C5 | Me | Me | BR | (TFPr—)$_7$(BR-CMe$_2$—OCO—C5-DM—)$_3$Si$_7$O$_{12}$ |
| 134 | Et | C2OC3 | Me | Me | BR | (Et—)$_7$(BR-CMe$_2$—OCO—C2OC3-DM—)$_3$Si$_7$O$_{12}$ |
| 135 | IBu | C2OC3 | Me | Me | BR | (IBu—)$_7$(BR-CMe$_2$—OCO—C2OC3-DM—)$_3$Si$_7$O$_{12}$ |
| 136 | IOc | C2OC3 | Me | Me | BR | (IOc—)$_7$(BR-CMe$_2$—OCO—C2OC3-DM—)$_3$Si$_7$O$_{12}$ |
| 137 | CPe | C2OC3 | Me | Me | BR | (CPe—)$_7$(BR-CMe$_2$—OCO—C2OC3-DM—)$_3$Si$_7$O$_{12}$ |
| 138 | CHe | C2OC3 | Me | Me | BR | (CHe—)$_7$(BR-CMe$_2$—OCO—C2OC3-DM—)$_3$Si$_7$O$_{12}$ |
| 139 | Ph | C2OC3 | Me | Me | BR | (Ph—)$_7$(BR-CMe$_2$—OCO—C2OC3-DM—)$_3$Si$_7$O$_{12}$ |
| 140 | TFPr | C2OC3 | Me | Me | BR | (TFPr—)$_7$(BR-CMe$_2$—OCO—C2OC3-DM—)$_3$Si$_7$O$_{12}$ |
| 141 | Et | C3 | Et | Et | BR | (Et—)$_7$(BR-CEt$_2$—OCO—C3-DM—)$_3$Si$_7$O$_{12}$ |
| 142 | IBu | C3 | Et | Et | BR | (IBu—)$_7$(BR-CEt$_2$—OCO—C3-DM—)$_3$Si$_7$O$_{12}$ |
| 143 | IOc | C3 | Et | Et | BR | (IOc—)$_7$(BR-CEt$_2$—OCO—C3-DM—)$_3$Si$_7$O$_{12}$ |
| 144 | CPe | C3 | Et | Et | BR | (CPe—)$_7$(BR-CEt$_2$—OCO—C3-DM—)$_3$Si$_7$O$_{12}$ |
| 145 | CHe | C3 | Et | Et | BR | (CHe—)$_7$(BR-CEt$_2$—OCO—C3-DM—)$_3$Si$_7$O$_{12}$ |
| 146 | Ph | C3 | Et | Et | BR | (Ph—)$_7$(BR-CEt$_2$—OCO—C3-DM—)$_3$Si$_7$O$_{12}$ |
| 147 | TFPr | C3 | Et | Et | BR | (TFPr—)$_7$(BR-CEt$_2$—OCO—C3-DM—)$_3$Si$_7$O$_{12}$ |

TABLE 13

| No. | $R^{11}$ | $Z^4$ | $R^7$ | $R^8$ | $X^1$ | Formula (1-3-1) |
|---|---|---|---|---|---|---|
| 148 | Et | C4 | Et | Et | BR | (Et—)$_7$(BR-CEt$_2$—OCO—C4-DM—)$_3$Si$_7$O$_{12}$ |
| 149 | IBu | C4 | Et | Et | BR | (IBu—)$_7$(BR-CEt$_2$—OCO—C4-DM—)$_3$Si$_7$O$_{12}$ |
| 150 | IOc | C4 | Et | Et | BR | (IOc—)$_7$(CL—CEt$_2$—OCO—C4-DM—)$_3$Si$_7$O$_{12}$ |
| 151 | CPe | C4 | Et | Et | BR | (CPe—)$_7$(BR-CEt$_2$—OCO—C4-DM—)$_3$Si$_7$O$_{12}$ |
| 152 | CHe | C4 | Et | Et | BR | (CHe—)$_7$(BR-CEt$_2$—OCO—C4-DM—)$_3$Si$_7$O$_{12}$ |
| 153 | Ph | C4 | Et | Et | BR | (Ph—)$_7$(CL—CEt$_2$—OCO—C4-DM—)$_3$Si$_7$O$_{12}$ |
| 154 | TFPr | C4 | Et | Et | BR | (TFPr—)$_7$(BR-CEt$_2$—OCO—C4-DM—)$_3$Si$_7$O$_{12}$ |
| 155 | Et | C5 | Et | Et | BR | (Et—)$_7$(BR-CEt$_2$—OCO—C5-DM—)$_3$Si$_7$O$_{12}$ |
| 156 | IBu | C5 | Et | Et | BR | (IBu—)$_7$(BR-CEt$_2$—OCO—C5-DM—)$_3$Si$_7$O$_{12}$ |
| 157 | IOc | C5 | Et | Et | BR | (IOc—)$_7$(BR-CEt$_2$—OCO—C5-DM—)$_3$Si$_7$O$_{12}$ |
| 158 | CPe | C5 | Et | Et | BR | (CPe—)$_7$(BR-CEt$_2$—OCO—C5-DM—)$_3$Si$_7$O$_{12}$ |
| 159 | CHe | C5 | Et | Et | BR | (CHe—)$_7$(BR-CEt$_2$—OCO—C5-DM—)$_3$Si$_7$O$_{12}$ |
| 160 | Ph | C5 | Et | Et | BR | (Ph—)$_7$(BR-CEt$_2$—OCO—C5-DM—)$_3$Si$_7$O$_{12}$ |
| 161 | TFPr | C5 | Et | Et | BR | (TFPr—)$_7$(BR-CEt$_2$—OCO—C5-DM—)$_3$Si$_7$O$_{12}$ |
| 162 | Et | C2OC3 | Et | Et | BR | (Et—)$_7$(BR-CEt$_2$—OCO—C2OC3-DM—)$_3$Si$_7$O$_{12}$ |
| 163 | IBu | C2OC3 | Et | Et | BR | (IBu—)$_7$(BR-CEt$_2$—OCO—C2OC3-DM—)$_3$Si$_7$O$_{12}$ |
| 164 | IOc | C2OC3 | Et | Et | BR | (IOc—)$_7$(BR-CEt$_2$—OCO—C2OC3-DM—)$_3$Si$_7$O$_{12}$ |
| 165 | CPe | C2OC3 | Et | Et | BR | (CPe—)$_7$(BR-CEt$_2$—OCO—C2OC3-DM—)$_3$Si$_7$O$_{12}$ |
| 166 | CHe | C2OC3 | Et | Et | BR | (CHe—)$_7$(BR-CEt$_2$—OCO—C2OC3-DM—)$_3$Si$_7$O$_{12}$ |
| 167 | Ph | C2OC3 | Et | Et | BR | (Ph—)$_7$(BR-CEt$_2$—OCO—C2OC3-DM—)$_3$Si$_7$O$_{12}$ |
| 168 | TFPr | C2OC3 | Et | Et | BR | (TFPr—)$_7$(BR-CEt$_2$—OCO—C2OC3-DM—)$_3$Si$_7$O$_{12}$ |

The compound (1-3) shall not be restricted by the examples described in Table 6 to Table 13. The compounds in which $R^{11}$ is tridecafluoro-1,1,2,2-tetrahydrooctyl are preferred as well.

Next, the production processes of the compound (1-1) and the compound (1-2) among the silicon compounds of the present invention shall be explained.

One of the preferred raw materials is a compound (3-1):

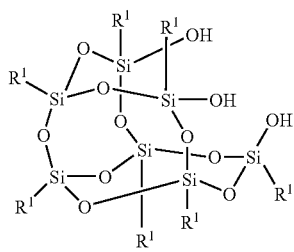
(3-1)

$R^1$ in Formula (3-1) has the same meaning as that of $R^1$ in Formula (1). Such compound can be synthesized by hydrolyzing a trichlorosilane compound and further maturing it. For example, Frank J. Feher et al. obtain a compound in which $R^1$ is cyclopentyl in Formula (3-1) by reacting cyclopentyltrichlorosilane in a water-acetone mixed solvent under a room temperature or refluxing temperature and further maturing it for 2 weeks (refer to Organometallics, 10, 2526-(1991) or Chemical European Journal, 3, No. 6, 900-(1997)). An Si—H functional silsesquioxane derivative can be produced by reacting the compound (3-1) with Si—H functional diorganochlorosilane by making use of the reactivity of silanol (Si—OH).

The Si—H functional diorganochlorosilane is represented by Formula (4). The preferred example of the compound (4) is dimethylochlorosilane. A compound (5) is obtained by reacting the compound (3-1) with the compound (4):

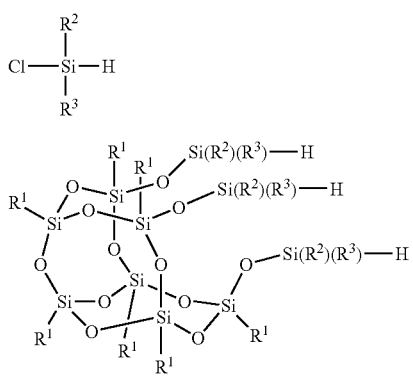

$R^1$, $R^2$ and $R^3$ in Formula (4) and Formula (5) have the same meanings as those of these codes in Formula (1).

A method making use of nucleophilic displacement can be adopted in order to synthesize the compound (5) from the compound (3-1) and the compound (4). This method is described in, for example, J. Am. Chem. Soc., 112, 1931-(1990). Conditions for selecting a solvent used for this nucleophilic displacement reaction are that it is not reacted with the compound (3-1) and the compound (4) and that it is sufficiently dehydrated. The examples of the solvent are tetrahydrofuran, toluene and dimethylformamide. The most preferred solvent is well-dehydrated tetrahydrofuran. A preferred use amount of the compound (4) is 3 to 15 times in terms of an equivalent ratio based on the compound (3-1) when it is reacted with all of the Si—OH (silanol) groups of the compound (3-1). In this reaction, hydrogen chloride is generated by reacting hydrogen of silanol with chlorine of chlorosilane, and therefore this hydrogen chloride has to be removed from the reaction system. A method for removing hydrogen chloride shall not be restricted, and triethylamine is most preferably used. A preferred use amount of triethylamine is 3 to 15 times in terms of an equivalent ratio based on the compound (3-1). A preferred reaction temperature is a temperature at which side reactions do not take place at the same time and at which a quantitative nucleophilic displacement reaction can be allowed to proceed. In charging the raw materials, it is most preferably carried out under a low temperature condition, for example, in an ice bath, and then it may be carried out at a room temperature. The reaction time shall not specifically be restricted as long as it is time enough for allowing a quantitative nucleophilic displacement reaction to proceed. Usually, the intended silicon compound can be obtained in 10 to 15 hours.

Another preferred raw material used in the present invention is a compound (3-2):

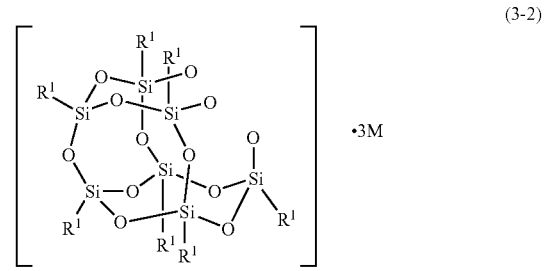
(3-2)

In Formula (3-2), $R^1$ is the same as $R^1$ in Formula (1), and M is a monovalent alkali metal atom. The preferred examples of the alkali metal are sodium and potassium. The most preferred example is sodium.

The compound (3-2) is obtained by preparing a silsesquioxane oligomer by hydrolyzing a silane compound having a trifunctional hydrolyzable group and reacting this with a monovalent alkali metal hydroxide in an organic solvent. It is obtained as well by hydrolyzing and condensing the silane compound having a trifunctional hydrolyzable group in the presence of an organic solvent, water and an alkali metal hydroxide. The compound (3-2) can be produced for short time at a high yield by either method (refer to, for example, WO02/09839 pamphlet). In producing the compound (3-2), the compound (3-2) in which seven $R^1$'s in Formula (3-2) are constituted from at least two different groups can be obtained by using at least two silane compounds having a trifunctional hydrolyzable group. The compound (3-2) shows a higher reactivity than that of a silanol group of the compound (3-1). Accordingly, use of the above compound for a raw material makes it possible to readily synthesize the derivative thereof at a high yield. Further, since it has —ONa as a reactive group, hydrogen chloride is not generated if chlorosilanes are used for synthetic reaction of the derivative. Accordingly, the reaction operation can be facilitated, and it can completely-be reacted. That is, the compound (5) can readily be obtained from the compound (3-2) and the compound (4).

Reaction in which the compound (3-2) is reacted with the compound (4) to prepare the compound (5) can be carried out as well in the same manner as in a case where the compound (3-1) is used. A preferred use amount of the compound (4) is 3 to 15 times in terms of an equivalent ratio based on the compound (3-2). In the above reaction, triethylamine does not have to be used for the purpose of removing hydrogen chloride. However, triethylamine may be used as a catalytic role for allowing the reaction to proceed quickly. When using triethylamine, a use amount thereof is preferably 3 to 15 times in terms of an equivalent ratio based on the compound (3-2). A preferred solvent used in the reaction is the same as in the reaction using the compound (3-1).

The reaction temperature shall not specifically be restricted as long as side reactions do not take place at the same time and a quantitative nucleophilic reaction goes on. In charging the raw materials, however, the reaction may be carried out under a low temperature condition, for example, in an ice bath. The subsequent reaction may be carried out under a room temperature condition or a heating condition. To be specific, the reaction temperature falls in a range of 0 to 150° C., more preferably in a range of 0 to 50° C. The reaction time shall not specifically be restricted as long as it is time enough for allowing a quantitative nucleophilic reaction to go on. Usually, the intended silicon compound can be obtained in 1 to 15 hours.

The preferred synthetic process for the silicon compound of the present invention is a process carried out by a hydrosilylation reaction using the compound (5) described above. A compound having haloalkylphenyl can be synthesized by the hydrosilylation reaction alone. That is, it is a reaction of the compound (5) with a compound (6-1) in the presence of a transition metal catalyst:

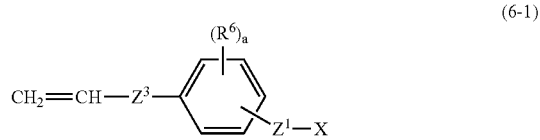

(6-1)

Codes in Formula (6-1) are codes defined in the same manners as in the codes in Formula (2-1-1) described above, and the bonding positions of $Z^1$ and $R^6$ on a benzene ring are the same as the bond positions of these codes in Formula (2-1-1).

The examples of the transition metal catalyst used are platinum, rhodium, iridium, ruthenium, palladium, molybdenum, iron, cobalt, nickel and manganese. Among them, a platinum catalyst is more preferred. The above catalysts can be used in the form of a homogeneous catalyst prepared by dissolving them in a solvent or a solid catalyst prepared by carrying them on carbon or silica. They may be used in a form in which phosphine, amine and potassium acetate are allowed to coexist. A preferred use amount of the transition metal catalyst is $1\times10^{-6}$ to $1\times10^{-2}$ mole per mole of an Si—H group in the compound (5) in terms of a transition metal atom.

A use amount of the compound (6-1) is preferably 1 to 5 times in terms of an equivalent ratio based on an Si—H group in the compound (5). The hydrosilylation reaction is a reaction which proceeds almost quantitatively, and therefore it is not meaningful so much to raise the above equivalent ratio. However, an effect of shortening the reaction time can be expected, and therefore an adverse effect of using a large amount of the compound (6-1) is only the cost efficiency. On the other hand, when a part of the Si—H group is allowed to remain as it is unreacted, it is advisable merely to make the above equivalent ratio described above smaller than 1. Thus, a compound represented by Formula (1-1) is obtained:

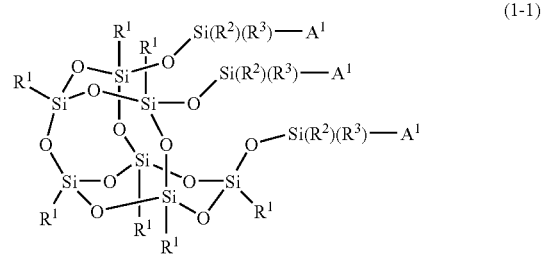

(1-1)

$R^1$, $R^2$ and $R^3$ in Formula (1-1) have the same meanings as those of these codes in Formula (1), and $A^1$ is a group represented by Formula (2-1-1):

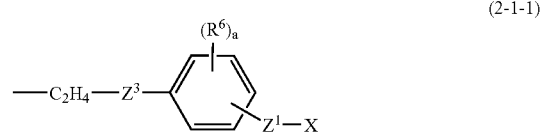

(2-1-1)

A preferred reaction temperature in the hydrosilylation reaction is not higher than a boiling point of the solvent used. The compound (6-1) is a compound having a polymerizable unsaturated bond. The preferred reaction temperature for preventing this compound from being spontaneously polymerized during the hydrosilylation reaction is 20 to 80° C. A polymerization inhibitor such as phenol derivatives, phenothiazine derivatives or N-nitrosophenylamine salt derivatives may be used for the purpose of inhibiting the above polymerization reaction. The most preferred polymerization inhibitor is 4-tert-butylpyrocatechol. A preferred use amount thereof is 1 to 100,000 ppm based the whole weight of the reaction liquid. The more preferred range of the use amount thereof is 100 to 20,000 ppm.

An organic solvent used for the above hydrosilylation reaction shall not specifically be restricted as long as it readily dissolves the raw materials without reacting with them. The preferred examples of the organic solvent are aliphatic hydrocarbons (examples: hexane and heptane), aromatic hydrocarbons (examples: toluene and xylene) and cyclic ethers (examples: tetrahydrofuran and dioxane). Considering the solubility of the compound (5), toluene is most preferred. Alcohols such as 2-propanol may be added for the purpose of controlling the activity of the catalyst.

In the following explanations, the unreacted raw material compounds and the solvent shall be referred to as impurities in all. If a distillation method is applied in order to remove the impurities, the liquid is maintained under a high temperature condition for long time, and therefore spontaneous polymerization of the unreacted compounds having a double bond is likely to be induced. Accordingly, a refining method carried out by reprecipitation operation is preferably used in order to efficiently remove the impurities without damaging a purity of the compound (1-1). This refining method is carried out in the following manner. First, the reaction liquid is dissolved in a solvent dissolving both of the compound (1-1) and the impurities. In this case, a preferred concentration of the compound (1-1) is, roughly speaking, 1 to 15% by weight. Next, such solvent as not dissolving the compound (1-1) but dissolving the impurities, a so-called precipitant is added to the above solution to precipitate only the compound (1-1). A preferred use amount of the precipitant is 20 to 50 times based on the weight of the solvent used for dissolving both of the compound (1-1) and the impurities. This use range is a rough standard, and as is the case with the foregoing concentration rage of the compound (1-1), it does not necessarily have to fall in the above range.

The preferred solvent used for dissolving the compound (1-1) is a solvent having a large dissolving power and a relatively low boiling point. The preferred precipitant is a solvent which is compatible with the solvent for dissolving the compound (1-1) and does not dissolve the compound (1-1) at all and which dissolves only the impurities and has a relatively low boiling point. The example of the preferred precipitant is lower alcohols. The particularly preferred precipitant is methanol. A repeating frequency of the reprecipitation operation is advisably raised in order to further elevate the refining degree.

A column chromatography is preferred for further refining the compound (1-1) after removing the polymerizable unreacted products. A preferred adsorbent used in this case is silica gel and the like. A preferred developing solvent is hexane, cyclohexane, toluene, chloroform, ethyl acetate and acetone. The more preferred developing solvent is a mixed solvent of ethyl acetate and hexane. A mixing ratio of the solvents shall not specifically be restricted, and it may be controlled so that a transfer rate (Rf value) of the specified substance into the developing solvent falls in a range of 0.1 to 0.7.

A silicon compound represented by Formula (1-2) can be obtained by reacting the compound (1-1) obtained at the hydrosilylation reaction step described above with a dithiocarbamic acid metal salt represented by Formula (7):

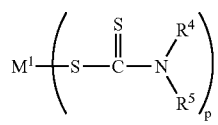

(7)

$R^4$ and $R^5$ in Formula (7) are groups defined in the same manner as in these codes in Formula (2-2-1); $M^1$ is a metal element of the 1st or the 2nd group in the periodic table; and p is the same value as an atomic value of $M^1$. The examples of $M^1$ are Li, Na, K, Cu, Mg, Ca and Zn. The preferred examples of $M^1$ are Na and K.

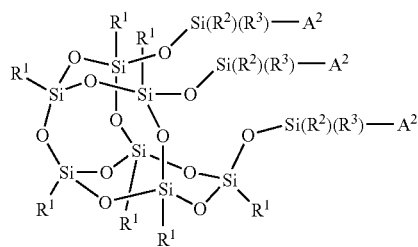

(1-2)

$A^2$ in the above formula is a group represented by Formula (2-2-1), and the other codes have the same meanings as those of these codes in Formula (1-1).

The reaction of the compound (1-1) with the compound (7) is a quantitative nucleophilic displacement reaction, and side reactions do not take place. However, a preferred use amount of dithiocarbamate is 1 to 5 times in terms of an equivalent ratio based on a halogen content in the compound (1-1). Use of this salt in a large amount makes it possible to shorten the reaction time. The reaction is usually carried out in an atmosphere of inert gas such as nitrogen in a dried organic solvent which is inert to the raw materials. The examples of the organic solvent are lower alcohols (example: methanol), cyclic ethers (examples: tetrahydrofuran and dioxane) and aromatic hydrocarbons (examples: toluene and xylene). The preferred examples of the organic solvent are tetrahydrofuran and methanol. The preferred reaction temperature is 120° C. or lower considering the possibility that dithiocarbamate is thermally decomposed. The more preferred reaction temperature is 100° C. or lower. The reaction time shall not specifically be restricted, and the intended silicon compound can be obtained usually in 1 to 10 hours. Capable of being used, if necessary, for the reaction is a phase transfer catalyst such as benzyltrimethylammonium chloride, tetramethylammonium chloride, tetrabutylammonium bromide, trioctylammonium chloride, dioctylmethylammonium chloride, triethylamine and dimethylaniline.

The compound (1-2) contained in the reaction mixture is refined by a refining method carried out by the reprecipitation operation described above and/or a column chromatography. The reaction of the dithiocarbamate with the compound (1-1) and refining of the compound (1-2) have to be carried out under a fluorescent lamp in which a UV ray is cut off and in a draft on which a UV-cut film is applied. The compound (1-2) has dithiocarbamate which is a photosensitive group, and therefore it has to be stored in a light-shielded vessel charged with inert gas such as nitrogen and argon in a cold and dark place under non-aqueous environment.

The compound (1-2) can be obtained as well by a process in which a step of reacting a dithiocarbamic acid metal salt with a halogenated alkyl group is carried out in advance. This production process is a process in which the compound (6-1) described above is first reacted with the compound (7) to prepare a compound represented by Formula (6-2):

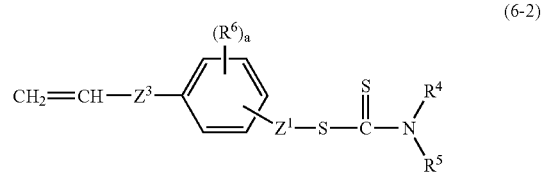

(6-2)

Codes in this formula are defined in the same manner as in the codes in Formula (2-2-1). The bonding positions of $Z^1$ and $R^6$ on a benzene ring are the same as the bond positions of these codes in Formula (2-2-1).

The above reaction itself is fundamentally the same as the reaction of the compound (1-1) described above with the compound (7), and it can be carried out in the same manner as in the case of the above reaction. However, the same caution as in the reaction of the compound (5) with the compound (6-1) in the production process described above is required in terms of handling the compounds having a polymerizable group. That is, the reaction temperature has to be controlled to a considerably low temperature of 20 to 80° C., and a polymerization inhibitor has to be used as well. Further, a UV ray has to be cut off as much as possible not only in the reaction and the refining step but also in storing the product. Thus, the compound (1-2) can be obtained by the hydrosilylation reaction of the compound (5) with the compound (6-2). This hydrosilylation reaction can be carried out in the same manner as in the reaction of the compound (5) with the compound (6-1).

The compound (1-1) can be produced as well by a production process in which reaction using the compound (3-1) or the compound (3-2) is set to a final reaction step. First, the compound (4) and the compound (6-1) are subjected to hydrosilylation reaction in the presence of a transition metal catalyst to produce a compound (8-1):

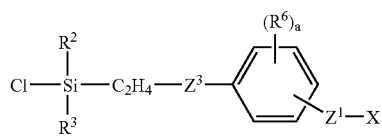
(8-1)

In Formula (8-1), $R^2$ and $R^3$ have the same meanings as those of these codes in Formula (4), and the other codes have the same meanings as those of the respective codes in Formula (6-1). The bonding positions of $Z^1$ and $R^6$ on a benzene ring are the same as the bond positions of these codes in Formula (6-1).

Then, the compound (8-1) is reacted with the compound (3-1) or the compound (3-2), whereby the compound (1-1) can be produced. The hydrosilylation reaction of the compound (4) with the compound (6-1) can be carried out in the same manner as in the hydrosilylation reaction of the compound (5) with the compound (6-1). The reaction of the compound (8-1) with the compound (3-1) or the compound (3-2) can be carried out in the same manner as in the reaction of the compound (4) with the compound (3-1) or the compound (3-2).

The compound (1-2) also can be produced by a production process in which reaction using the compound (3-1) or the compound (3-2) is set to a final reaction step. That is, first the compound (6-2) is obtained from the compound (6-1) and the compound (7), and then a compound represented by Formula (8-2) is produced by the hydrosilylation reaction of the compound (6-2) with the compound (4):

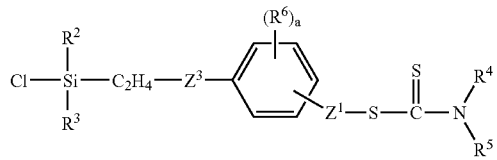
(8-2)

In Formula (8-2), $R^2$ and $R^3$ have the same meanings as those of these codes in Formula (4), and the other codes have the same meanings as those of the codes in Formula (6-2). The bonding positions of $Z^1$ and $R^6$ on a benzene ring are the same as the bond positions of these codes in Formula (6-2).

Finally, the compound (1-2) can be produced by reacting the above compound (8-2) with the compound (3-1) or the compound (3-2). The hydrosilylation reaction of the compound (6-2) with the compound (4) can be carried out in the same manner as in the hydrosilylation reaction of the compound (5) with the compound (6-1). The reaction of the compound (8-2) with the compound (3-1) or the compound (3-2) can be carried out in the same manner as in the reaction of the compound (4) with the compound (3-1) or the compound (3-2). A process in which the compound (8-1) described above is reacted with the compound (7) is considered as well for a production process for the compound (8-2).

Next, a production process for the compound (1-3) among the silicon compounds of the present invention shall be explained.

A preferred raw material used in this process is a silicon compound represented by Formula (9):

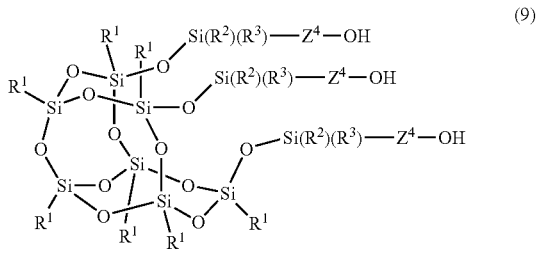
(9)

$R^1$, $R^2$ and $R^3$ in the above formula are groups defined in the same manners as in these codes in Formula (1), and $Z^4$ is defined in the same manner as in $Z^4$ in Formula (2-3). The compound (1-3) is obtained by reacting the above compound (9) with a compound (10) in which halogen is bonded to carbon of an α position:

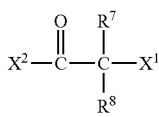
(10)

$R^7$, $R^8$ and $X^1$ in the above formula are defined in the same manners as in these codes in Formula (2-3), and $X^2$ is halogen. The examples of this halogen are chlorine, bromine and iodine, and chlorine and bromine are preferred. $X^1$ and $X^2$ may be same or different.

Synthetic routes shown in the following scheme 1 (or scheme 2) and scheme 3 are one of the specific examples of the process for producing the compound (1-3). In the following schemes, $Pt_2(dvds)_3$ is a platinum-divinyltetramethyldisiloxane complex; Me is methyl; Ph is phenyl; THF is tetrahydrofuran; and TEA is triethylamine.

Scheme 1

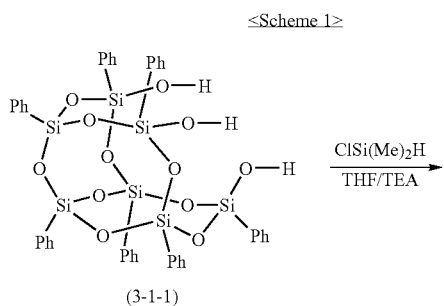

(3-1-1) → ClSi(Me)₂H / THF/TEA

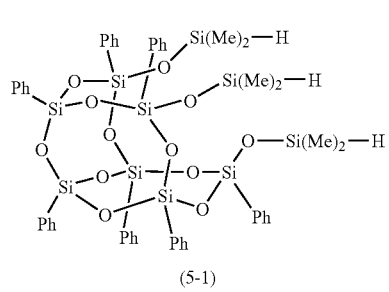

(5-1)

That is, in the scheme 1, a compound (3-1-1) is reacted with dimethylchlorosilane using THF as a solvent at a room temperature in the presence of triethylamine to prepare a compound (5-1). The compound (3-1-1) is described in Organometallics, 10, 2526-(1991).

Scheme 2

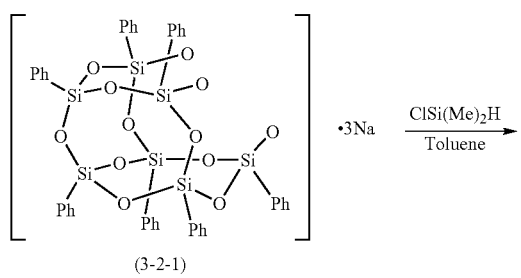

(3-2-1) ·3Na, ClSi(Me)₂H / Toluene →

-continued

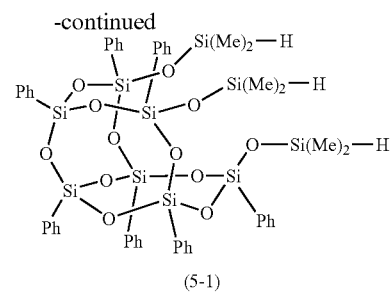

(5-1)

In the scheme 2, a compound (3-2-1) is reacted with dimethylchlorosilane using toluene as a solvent under heating and refluxing in the absence of triethylamine to prepare the compound (5-1). The compound (3-2-1) is described in a WO02/094839 pamphlet. Either process of the scheme 1 and the scheme 2 can be adopted. These schemes are the specific examples which are common to the production of the compound (1-1) and the compound (1-2).

Scheme 3

(5-1) + alkenyl alcohol → Pt₂(dvds)₃/Toluene

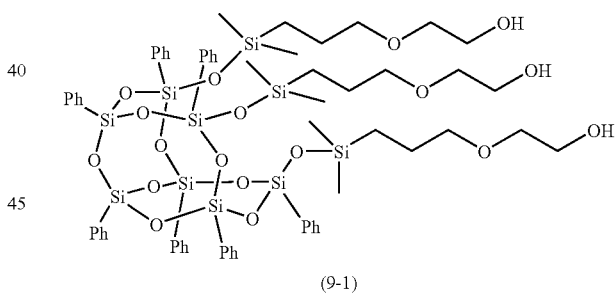

(9-1)

Then, in the scheme 3, the compound (5-1) and alcohol having an alkenyl group are subjected to a hydrosilylation reaction in toluene in the presence of a platinum-divinyltetramethyldisiloxane complex, whereby a compound (9-1) having a hydroxyl group can be prepared. These synthetic routes are one example for producing the compound (9) and shall not restrict the present invention.

Further, the compound (9) can be produced as well by the following process. First, the compound (5-1) and alcohol having an alkenyl group which is protected by a trimethylsilyl group are subjected to a hydrosilylation reaction in toluene in the presence of a platinum-divinyltetramethyldisiloxane complex to thereby produce a compound (9-T). Then, it is derived into the compound (9-1) having a hydroxyl group by alcoholysis using large excess methanol at a room temperature or on a condition of slightly heating (40° C.). In the following scheme, TMS is a trimethylsilyl group.

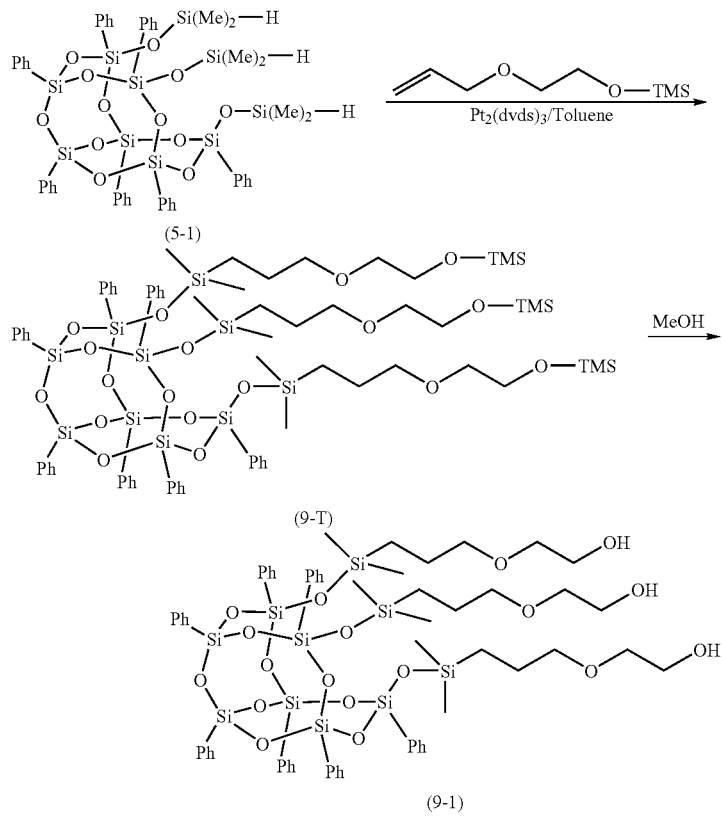

<Scheme 4>

The compound (9) thus obtained is reacted with the compound (10), whereby a compound (1-3) which is the preferred example of the compound of the present invention can be obtained.

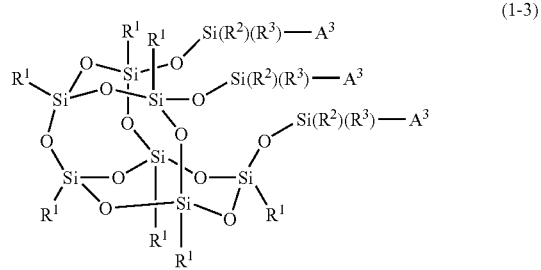

(1-3)

In Formula (1-3), $R^1$, $R^2$ and $R^3$ have the same meanings as those of these codes in Formula (9), and $A^3$ is the group represented by Formula (2-3) described above.

The compound (9) is readily reacted with the compound (10) to be esterified. Hydrogen chloride by-produced in the reaction induces side reactions such as dehydration and addition to a double bond part, and therefore the reaction is carried out in the coexistence of an organic base in order to remove it. The examples of the organic base are pyridine, dimethylaniline, triethylamine and tetramethylurea. Other organic bases may be used as long as they can inhibit the side reactions and allow the reaction to quickly proceed. The most preferred example of the organic base is triethylamine. This reaction is a nucleophilic displacement reaction which proceeds quantitatively, and a use amount of the compound (10) is preferably 1 to 10 times in terms of an equivalent ratio based on the compound (9). An increase in a use amount of the compound (10) makes it possible to react the whole compound (9) and makes it possible to shorten the reaction time.

Usually, the above reaction is carried out in environment of inert gas such as argon gas and nitrogen gas and in a dried organic solvent which is inert to the raw materials. The examples of the organic solvent are cyclic ethers (tetrahydrofuran, dioxane and the like), aromatic hydrocarbons (toluene, xylene and the like), halogenated hydrocarbons (methylene chloride, chloroform and the like) and carbon tetrachloride. The preferred example of the organic solvent is methylene chloride. The reaction temperature shall not specifically be restricted. However, the above reaction quickly goes on while generating heat, and therefore usually it is carried out preferably under a low temperature condition. The preferred reaction temperature is 100° C. or lower, and the most referred reaction temperature is 35° C. or lower. As a matter of fact, the reaction may be carried out while irregularly controlling the reaction temperature. For example, the reaction may be carried out while cooling the reaction system using a dry ice-methanol bath or an ice bath in an initial stage, and then the temperature may be elevated to the vicinity of a room temperature to continue the reaction. The reaction time shall not specifically be restricted, and usually the intended silicon compound can be obtained in 1 to 10 hours.

In the following explanations, a general term "impurities" shall be given to the unreacted raw material compounds and the solvent. If a distillation method is applied in order to remove the impurities, the liquid is maintained under a high temperature condition for long time, and therefore the intended compound is likely to be decomposed. Accordingly, refining is preferably carried out by reprecipitation operation in order to efficiently remove the impurities without damaging a purity of the compound (1-3). This refining method is carried out in the following manner. First, the reaction liquid is dissolved in a solvent dissolving both of the compound (1-3) and the impurities. In this case, a preferred concentration of the compound (1-3) is, roughly speaking, 1 to 15% by weight. Next, such solvent as not dissolving the compound (1-3) but dissolving the impurities, a so-called precipitant is added to the above solution to precipitate only the compound (1-3). A preferred use amount of the precipitant is 20 to 50 times based on the weight of the solvent used for dissolving both of the compound (1-3) and the impurities. This use range is a rough standard, and as is the case with the foregoing concentration rage of the compound (1-3), it does not necessarily have to fall in the above range.

The preferred solvent used for dissolving the compound (1-3) is a solvent having a large dissolving power and a relatively low boiling point. The preferred precipitant is a solvent which is compatible with the solvent for dissolving the compound (1-3) and does not dissolve the compound (1-3) at all and which dissolves only the impurities and has a relatively low boiling point. The example of the preferred precipitant is lower alcohols. The particularly preferred precipitant is methanol. A repeating frequency of the reprecipitation operation is advisably raised in order to further elevate the refining degree.

Next, an addition-polymerizable monomer which can initiate polymerization using the compound (1) shall be explained. This addition-polymerizable monomer is a monomer having at least one addition-polymerizable double bond. One of the examples of a monomer having one addition-polymerizable double bond is a (meth)acrylic acid derivative. The specific examples thereof are (meth)acrylic acid, methyl (meth)acrylate, ethyl (meth)acrylate, n-propyl (meth)acrylate, isopropyl (meth)acrylate, n-butyl (meth)acrylate, isobutyl (meth)acrylate, tert-butyl (meth)acrylate, n-pentyl (meth)acrylate, n-hexyl (meth)acrylate, cyclohexyl (meth)acrylate, n-heptyl (meth)acrylate, n-octyl (meth)acrylate, 2-ethylhexyl (meth)acrylate, nonyl (meth)acrylate, decyl (meth)acrylate, dodecyl (meth)acrylate, phenyl (meth)acrylate, toluyl (meth) acrylate, benzyl (meth)acrylate, 2-methoxyethyl (meth)acrylate, 3-methoxypropyl (meth)acrylate, 3-methoxybutyl (meth)acrylate, 2-hydroxyethyl (meth)acrylate, 2-hydroxypropyl (meth)acrylate, stearyl (meth)acrylate, glycidyl (meth)acrylate, 3-ethyl-3-(meth)acryloyloxymethyloxetane, 2-(meth)acryloyloxyethylisocyanate, 2-aminoethyl (meth)acrylate, 2-(2-bromopropanoylyloxy)ethyl (meth)acrylate, 2-(2-bromoisobutyryloxy)ethyl (meth)acrylate, 1-(meth)acryloxy-2-phenyl-2-(2,2,6,6-tetramethyl-1-piperidinyloxy) ethane, (1-(4-((4-(meth)acryloxy)ethoxyethyl)phenylethoxy)piperidine, γ-(methacryloyloxypropyl) trimethoxysilane, 3-(3,5,7,9,11,13,15-heptaethylpentacyclo[9.5.1.1$^{3,9}$.1$^{5,15}$.1$^{7,13}$]octasiloxane-1-yl)propyl (meth) acrylate, 3-(3,5,7,9,11,13,15-heptaisobutylpentacyclo [9.5.1.1$^{3,9}$. 1$^{5,15}$.1$^{7,13}$]octasiloxane-1-yl)propyl (meth) acrylate, 3-(3,5,7,9,11,13,15-heptaisooctylpentacyclo [9.5.1.1$^{3,9}$.1$^{5,15}$.1$^{7,13}$]octasiloxane-1-yl)propyl (meth) acrylate, 3-(3,5,7,9,11,13,15-heptacyclopentylpentacyclo [9.5.1.1$^{3,9}$.1$^{5,15}$.1$^{7,13}$]octasiloxane-1-yl)propyl (meth) acrylate, 3-(3,5,7,9,11,13,15-heptaphenylpentacyclo [9.5.1.1$^{3,9}$.1$^{5,15}$.1$^{7,13}$]octasiloxane-1-yl)propyl (meth) acrylate, 3-[(3,5,7,9,11,13,15-heptaethylpentacyclo [9.5.1.1$^{3,9}$.1$^{5,15}$.1$^{7,13}$] octasiloxane-1-yloxy)dimethylsilyl] propyl (meth)acrylate, 3-[(3,5,7,9,11,13,15-heptaisobutylpentacyclo[9.5.1.1$^{3,9}$. 1$^{5,15}$.1$^{7,13}$]octasilox ane-1-yloxy)dimethylsilyl]propyl (meth)acrylate, 3-[(3,5,7,9,11, 13,15-heptaisooctylpentacyclo[9.5.1.1$^{3,9}$. 1$^{5,15}$.1$^{7,13}$] octasiloxane-1-yloxy)dimethylsilyl]propyl(meth)acrylate, 3-[(3,5,7,9,11,13,15-heptacyclopentylpentacycl[9.5.1.1$^{3,9}$.1$^{5,15}$.1$^{7,13}$]octasiloxane-1-yloxy)dimethylsilyl]propyl (meth)acrylate, 3-[(3,5,7,9,11,13,15-heptaphenylpentacyclo [9.5.1.1$^{3,9}$.1$^{5,15}$.1$^{7,13}$]octasiloxane-1-yloxy)-dimethylsilyl] propyl (meth)acrylate, ethylene oxide adducts of (meth) acrylic acid, trifluoromethylmethyl (meth)acrylate, 2-trifluoromethylethyl (meth)acrylate, 2-perfluoroethylethyl (meth)acrylate, 2-perfluoroethyl-2-perfluorobutylethyl (meth)acrylate, 2-perfluoroethyl (meth)acrylate, trifluoromethyl (meth)acrylate, diperfluoromethylmethyl (meth)acrylate, 2-perfluoromethyl-2-perfluoroethylethyl (meth)acrylate, 2-perfluorohexylethyl (meth)acrylate, 2-perfluorodecylethyl (meth)acrylate, 2-perfluorohexadecylethyl (meth)acrylate and 2-(meth)acryloyloxyethylphosphorylcholine.

Another example of the monomer having one addition-polymerizable double bond is a styrene base monomer. The specific examples thereof are styrene, vinyltoluene, α-methylstyrene, p-chlorostyrene, p-chloromethylstyrene, m-chloromethylstyrene, o-aminostyrene, p-styrenechlorosulfonic acid, styrenesulfonic acid and salts thereof, vinylphenylmethyl dithiocarbamate, 2-(2-bromopropanonyloxy)styrene, 2-(2-bromo-isobutyryloxy) styrene, 1-(2-((4-vinylphenyl)-methoxy)-1-phenylethoxy)-2,2,6,6-tetramethyl-piperidine, 1-(4-vinylphenyl)-3,5,7,9,11,13,15-heptaethylpentacyclo [9.5.1.1$^{3,9}$.1$^{5,15}$.1$^{7,13}$]octasiloxane, 1-(4-vinylphenyl)-3,5,7,9,11,13,15-heptaisobutylpentacyclo[9.5.1.1$^{3,9}$.1$^{5,15}$.1$^{7,13}$] octasiloxane, 1-(4-vinylphenyl)-3,5,7,9,11,13,15-heptaisooctylpentacyclo[9.5.1.1$^{3,9}$. 1$^{5,15}$.1$^{7,13}$]octasiloxane, 1-(4-vinylphenyl)-3,5,7,9,11,13,15-heptacyclopentylpentacyclo[9.5.1.1$^{3,9}$.1$^{5,15}$.1$^{7,13}$]octasiloxane, 1-(4-vinylphenyl)-3,5,7,9,11,13,15-heptaphenylpentacyclo[9.5.1.1$^{3,9}$.1$^{5,15}$.1$^{7,13}$]octasiloxane, 3-(3,5,7,9,11,13,15-heptaethylpentacyclo [9.5.1.1$^{3,9}$.1$^{5,15}$.1$^{7,13}$]octasiloxane-1-yl)ethylstyrene, 3-(3,5,7,9,11,13,15-heptaisobutylpentacyclo [9.5.1.1$^{3,9}$.1$^{5,15}$.1$^{7,13}$] octasiloxane-1-yl)ethylstyrene, 3-(3,5,7,9,11,13,15-heptaisooctylpentacyclo[9.5.1.1$^{3,9}$.1$^{5,15}$.1$^{7,13}$]octasiloxane-1-yl)ethylstyrene, 3-(3,5,7,9,11,13,15-heptacyclopentylpentacyclo[9.5.1.1$^{3,9}$.1$^{5,15}$.1$^{7,13}$] octasiloxane-1-yl)ethylstyrene, 3-(3,5,7,9,11,13,15-heptaphenylpentacyclo[9.5.1.1$^{3,9}$.1$^{5,15}$.1$^{7,13}$]octasiloxane-1-yl)ethylstyrene, 3-((3,5,7,9,11,13,15-heptaethylpentacyclo [9.5.1.1$^{3,9}$.1$^{5,15}$.1$^{7,13}$]octasiloxane-1-yloxy)dimethylsilyl] ethylstyrene, 3-((3,5,7,9,11,13,15-heptaisobutylpentacyclo [9.5.1.1$^{3,9}$.1$^{5,15}$.1$^{7,13}$]octasiloxane-1-yloxy)dimethylsilyl) ethylstyrene, 3-((3,5,7,9,11,13,15-heptaisooctylpentacyclo [9.5.1.1$^{3,9}$.1$^{5,15}$.1$^{7,13}$]octasiloxane-1-yloxy)-dimethylsilyl) ethylstyrene, 3-((3,5,7,9,11,13,15-heptacyclopentylpentacyclo[9.5.1.1$^{3,9}$.1$^{5,15}$.1$^{7,13}$]octasiloxane-1-yloxy)dimethylsilyl)ethylstyrene and 3-((3,5,7,9,11,13,15-heptaphenylpentacyclo[9.5.1.1$^{3,9}$.1$^{5,15}$.1$^{7,13}$] octasiloxane-1-yloxy)dimethylsilyl]ethylstyrene.

The other examples of the monomer having one addition-polymerizable double bond are fluorine-containing vinyl monomers (perfluoroethylene, perfluoropropylene, vinylidene fluoride and the like), silicon-containing vinyl base monomers (vinyltrimethoxysilane, vinyltriethoxysilane and the like), maleic anhydride, maleic acid, monoalkyl esters and dialkyl esters of maleic acid, fumaric acid, monoalkyl esters and dialkyl esters of fumaric acid, maleimide base monomers (maleimide, methylmaleimide, ethylmaleimide, propylmaleimide, butylmaleimide, hexylmaleimide, octylmaleimide, dodecylmaleimide, stearylmaleimide, phenylmaleimide and cyclohexylmaleimide), monomers having a nitrile group (acrylonitrile, methacrylonitrile and the like), monomers having an amide group (acrylamide, methacrylamide and the like), vinyl ester base monomers (vinyl acetate, vinyl propionate, vinyl pivalate, vinyl benzoate, vinyl cinnamate and the like), olefins (ethylene, propylene and the like), conjugated diene base monomers (butadiene, isoprene and the like), halogenated vinyls (vinyl chloride and the like), halogenated vinylidenes (vinylidene chloride and the like), halogenated allyls (allyl chloride and the like), allyl alcohol, vinylpyrrolidone, vinylpyridine, N-vinylcarbazole, methyl vinyl ketone and vinylisocyanate. Further, given as well are macromonomers which have one polymerizable double bond in a molecule and in which a principal chain is a macromer of styrene, (meth)acrylic acid ester, diorganosiloxane or alkylene glycol.

The examples of a monomer having two addition-polymerizable double bonds are divinylbenzene and di(meth)acrylate base monomers. The examples of the di(meth)acrylate base monomers are 1,3-butanediol di(meth)acrylate, 1,4-butanediol di(meth)acrylate, 1,6-hexanediol di(meth)acrylate, polyethylene glycol di(meth)acrylate, diethylene glycol di(meth)acrylate, neopentyl glycol di(meth)acrylate, triethylene glycol di(meth)acrylate, tripropylene glycol di(meth)acrylate, hydroxypivalic acid ester neopentyl glycol di(meth)acrylate, trimethylolpropane di(meth)acrylate, bis[(meth)acryloyloxyethoxy] bisphenol A, bis[(meth)acryloyloxyethoxy] tetrabromobisphenol A, bis[(meth)acryloxypolyethoxy] bisphenol A, 1,3-bis(hydroxyethyl) 5,5-dimethylhydantoin, 3-methylpentanediol di(meth)acrylate, di(meth)acrylates of hydroxypivalic acid ester neopentyl glycol derivatives and bis[(meth)acryloyloxypropyl]tetramethyldisiloxane. Further, given as well are macromonomers which have two polymerizable double bonds in a molecule and in which a principal chain is a macromer of styrene, (meth)acrylic acid ester, diorganosiloxane or alkylene glycol.

The examples of a monomer having three or more addition-polymerizable double bonds are trimethylolpropane tri(meth)acrylate, pentaerythritol tri(meth)acrylate, pentaerythritol tetra(meth)acrylate, dipentaerythritol monohydroxypenta(meth)acrylate, tris(2-hydroxyethylisocyanate) tri(meth)acrylate, tris(diethylene glycol)trimelate tri(meth)acrylate, 3,7,14-tris[(((meth)acryloyloxypropyl)dimethylsiloxy)]-1,3,5,7,9,11,14-heptaethyltricyclo[7.3.3.1$^{5,11}$] heptasiloxane, 3,7,14-tris[(((meth)acryloyloxypropyl) dimethylsiloxy)]-1,3,5,7,9,11,14-heptaisobutyltricyclo [7.3.3.1$^{5,11}$]heptasiloxane, 3,7,14-tris[(((meth) acryloyloxypropyl)dimethylsiloxy)]-1,3,5,7,9,11,14-heptaisooctyltricyclo[7.3.3.1$^{5,11}$]heptasiloxane, 3,7,14-tris [(((meth)acryloyloxypropyl)dimethylsiloxy)]-1,3,5,7,9,11, 14-heptacyclopentyltricyclo[7.3.3.1$^{5,11}$]heptasiloxane, 3,7, 14-tris[(((meth)acryloyloxypropyl)dimethylsiloxy)]-1,3,5,7, 9,11,14-heptaphenyltricyclo[7.3.3.1$^{5,11}$]heptasiloxane, octakis(3-(meth)acryloyloxypropyldimethylsiloxy)octasilsesquioxane and octakis(3-(meth) acryloyloxypropyl) octasilsesquioxane. Further, given as well are macromonomers which have three or more polymerizable double bonds in a molecule and in which a principal chain is a macromer of styrene, (meth)acrylic acid ester, diorganosiloxane or alkylene glycol.

The monomers described above may be used alone or a plurality thereof may be copolymerized. When copolymerized, they may be random-copolymerized or block-copolymerized. The preferred monomers used in the present invention are the (meth)acrylic acid derivatives and the styrene derivatives. The more preferred monomers are the (meth) acrylic acid derivatives. The plural (meth)acrylic acid derivatives may be copolymerized, and the plural styrene derivatives may be copolymerized. At least one (meth)acrylic acid derivative may be copolymerized with at least one styrene derivative.

Next, a method for subjecting an addition-polymerizable monomer to atom transfer radical polymerization using the compound (1-1) or the compound (1-3) as an initiator and using a transition metal complex as a catalyst shall be explained. An atom transfer radical polymerization method in the present invention is one of living radical polymerization methods. The examples of documents in which the living radical polymerization method is described are J. Am. Chem. Soc., 1995, 117, 5614, and Macromolecules, 1995, 28, 7901 and Science, 1996, 272, 866.

The preferred examples of a transition metal complex used as a polymerizing catalyst are metal complexes in which the 7th, 8th, 9th, 10th or 11th group element in the periodic table is used as center metal. The more preferred catalysts are a complex of zero-valent copper, a complex of monovalent copper, a complex of divalent ruthenium, a complex of divalent iron and a complex of divalent nickel. Among them, the complexes of copper are preferred. The examples of a monovalent copper compound are cuprous chloride, cuprous bromide, cuprous iodide, cuprous cyanide, cuprous oxide and cuprous perchlorate. When using the copper compounds, 2,2'-bipyridyl or derivatives thereof, 1,10-phenanthroline or derivatives thereof, pyridylmethaneimines (N-(n-propyl)-2-pyridylmethaneimine and the like), polyamines (tetramethylethylenediamine, pentamethyldiethylenetriamine, hexamethyltris(2-aminoethyl)amine and the like) or polycyclic alkaloid such as L-(−)-sparteine are added as a ligand in order to enhance the catalyst activity. A tristriphenylphosphine complex ($RuC_2$ $(PPh_3)_3$) of divalent ruthenium chloride is also suitable as the catalyst. When the ruthenium compound is used as the catalyst, aluminum alkoxides are added as an activating agent. The examples of the suitable catalysts other than the above compounds are a bistriphenylphosphine complex ($FeCl_2(PPh_3)_2$) of divalent iron, a bistriphenylphosphine complex ($NiCl_2(PPh_3)_2$) of divalent nickel and a bistributylphosphine complex ($NiBr_2(PBu_3)_2$) of divalent nickel.

A solvent may be used for the polymerization reaction. The examples of the solvent used are hydrocarbons (examples: benzene, toluene and the like), ethers (examples: diethyl ether, THF, diphenyl ether, anisole, dimethoxybenzene and the like), halogenated hydrocarbons (examples: methylene chloride, chloroform, chlorobenzene and the like), ketones (examples: acetone, methyl ethyl ketone, methyl isobutyl ketone and the like), alcohols (examples: methanol, ethanol, propanol, isopropanol, n-butyl alcohol, tert-butyl alcohol and the like), nitrites (examples: acetonitrile, propionitrile, benzonitrile and the like), esters (examples: ethyl acetate, butyl acetate and the like), carbonate base solvents (examples: ethylene carbonate, propylene carbonate and the like), amide base solvents (examples: N,N-dimethylformamide, N,N-dimethylacetamide and the like), hydrochlorofluorocarbon base solvents (examples: HCFC-141b, HCFC-225 and the like), hydrofluorocarbon base solvents (examples: HFCs and the like), perfluorocarbon base solvents (examples: perfluoropentane, perfluorohexane and the like), alicyclic hydrofluorocarbon base solvents (examples: fluorocyclopentane, fluorocyclobutane and the like), oxygen-containing fluorine base solvents (examples: fluoroether, fluoropolyether, fluoroketone, fluoroalcohol and the like) and water. The compounds given above in parentheses are the preferred examples of the respective solvents. They may be used alone or in combination of two or more kinds thereof. The polymerization can be carried out as well in an emulsion system or a system in which a supercritical fluid $CO_2$ is used as a medium. The solvent which can be used shall not be restricted to the above examples.

The atom transfer radical polymerization can be carried out under reduced pressure, atmospheric pressure or applied pressure according to the kind of the addition-polymerizable monomer and the kind of the solvent. The polymerizing catalyst or a radical produced is likely to be deactivated when brought into contact with oxygen. In such case, the polymerizing rate is reduced, and a good living polymer is not obtained. Accordingly, it is important to carry out the polymerization under inert gas environment of nitrogen or argon. In this reaction, oxygen dissolved in the polymerization system has to be removed in advance under reduced pressure. Then, it is possible to shift to a polymerization step as it is under reduced pressure after finishing the step of removing dissolved oxygen. A conventional method can be adopted for the atom transfer radical polymerization, and it shall not specifically be restricted by the polymerization method. Capable of being adopted is, for example, a bulk polymerization method, a solution polymerization method, a suspension polymerization method, an emulsion polymerization method or a bulk-suspension polymerization method. The polymerization temperature falls in a range of 0 to 200° C., and the preferred polymerization temperature falls in a range of a room temperature to 150° C.

When using a compound (1-1-2) as an initiator, a polymer obtained by the method described above is represented by Formula (P-1). In the following explanations, the polymer represented by Formula (P-1) is shown as the polymer (P-1):

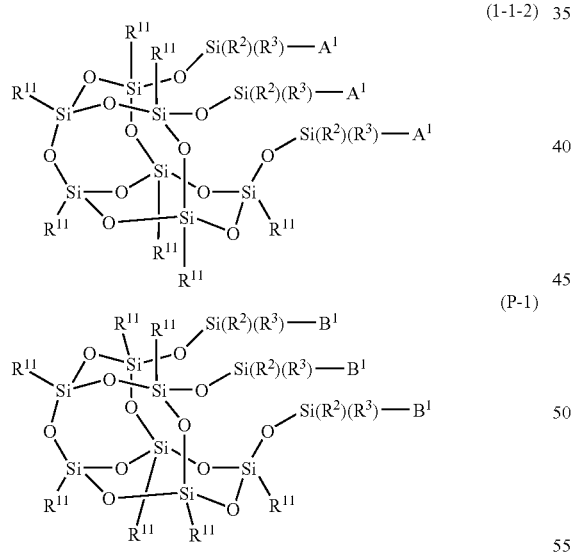

In Formula (1-1-2), all $R^{11}$'s are the same group selected from alkyl having a carbon atom number of 1 to 8 in which optional hydrogens may be substituted with fluorine and in which optional —$CH_2$— may be substituted with —O—, —CH=CH—, cycloalkylene or cycloalkenylene, phenyl in which optional hydrogens may be substituted with halogen, methyl or methoxy, non-substituted naphthyl and phenylalkyl constituted from a phenyl group in which optional hydrogens may be substituted with fluorine, alkyl having a carbon atom number of 1 to 4, vinyl or methoxy and an alkylene group in which optional —$CH_2$— may be substituted with —O—. $R^2$ and $R^3$ are groups independently selected from alkyl having a carbon atom number of 1 to 8, phenyl and cyclohexyl. $A^1$ is a group represented by Formula (2-1).

In Formula (P-1), $R^{11}$, $R^2$ and $R^3$ have the same meanings as those of these codes in Formula (1-1-2), and $B^1$ is a group represented by Formula (2-1-P):

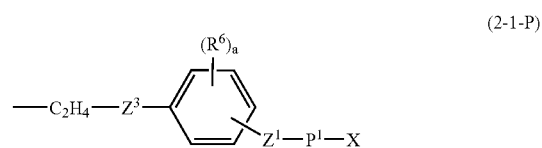

In the above formula, $P^1$ is a chain of a structural unit obtained by polymerizing an addition-polymerizable monomer, and the other codes have the same meanings as those of these codes in Formula (2-1).

When using a compound (1-3-2) as an initiator, a polymer obtained by the method described above is represented by Formula (P-3). In the following explanations, the polymer represented by Formula (P-3) is shown as the polymer (P-3):

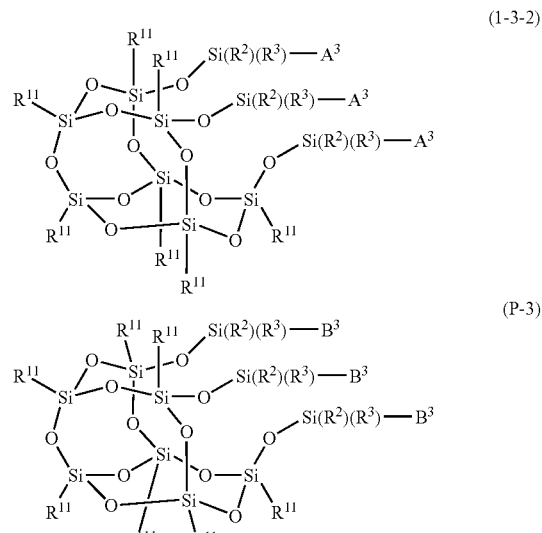

In the above formulas, $R^{11}$, $R^2$ and $R^3$ have the same meanings as those of these codes in Formula (1-1-2). $A^3$ is a group represented by Formula (2-3), and B3 is a group represented by Formula (2-3-P):

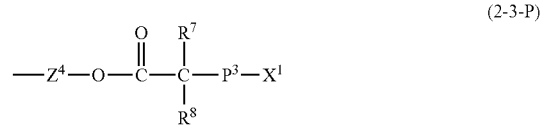

In the above formula, $P^3$ is a chain of a structural unit obtained by polymerizing an addition-polymerizable monomer, and the other codes have the same meanings as those of these codes in Formula (2-3).

Suitable selection of the kind of the monomer used makes it possible to control the structure of the polymer (P-3). For example, if the monomer is homopolymerized, silsesquioxane to which the homopolymer is bonded is obtained. If the plural monomers are added at the same time and polymerized, silsesquioxane to which the random copolymer is bonded is obtained. If adopted is a method in which the monomers are successively added, for example, a method in which the second monomer is added after finishing the polymerization of the first monomer to complete the polymerization, silsesquioxane to which the block copolymer is bonded is obtained. Repeating of the above staged polymerization using plural monomers makes it possible to obtain silsesquioxane to which the multiblock copolymer is bonded. Coexistence of, if necessary, a multifunctional monomer makes it possible as well to prepare a cross-linked polymer having a three-dimensional network structure.

When polymerizing a conventional addition-polymerizable monomer, combined use of a compound having a polymerizable functional group together with a function of an initiator makes it possible to obtain silsesquioxane to which a high branched type polymer is bonded. The example of such compound are 2-(2-bromopropanoyloxy)ethyl (meth)acrylate, 2-(2-bromoisobutyryloxy)ethyl (meth)acrylate, 2-(2-bromopropanoyloxy)styrene and 2-(2-bromoisobutyryloxy) styrene. Combined use of a silicon compound having a (meth) acryl group or a styryl group makes it possible to introduce a structural unit containing a silicon atom into the structure of the polymer. The examples of the above silicon compound are trialkoxysilane, polydimethylsiloxane and silsesquioxane. After copolymerized with an addition-polymerizable monomer having an initiating group which does not take part in atom transfer radical polymerization, the addition-polymerizable monomer is further polymerized in the other polymerization mode (for example, nitroxyl polymerization and photo initiator-transfer agent-terminator polymerization) using the resulting polymer as an initiator, whereby a graft copolymer can be formed. The examples of the addition-polymerizable monomer having an initiating group which does not take part in atom transfer radical polymerization are 1-(2-(4-vinylphenylmethoxy)-1-phenylethoxy-2,2,6,6-tetramethylpyridine, 1-(meth)acryloxy-2-phenyl-2-(2,2,6,6-tetramethyl-1-piperidinyloxy)ethane, (1-(4-(4-(meth)acryloxyethoxyethyl)phenylethoxy)piperidine and vinylphenylmethyldithiocarbamate.

After copolymerized with a monomer having a glycidyl group (example: glycidyl (meth)acrylate), a monomer having an oxetanyl group (example: 3-ethyl-3-(meth)acryloyloxymethyloxetane) or a monomer having dioxolane (example: 4-(meth)acryloyloxymethyl-2-methyl-2-ethyl-1,3-dioxolane), an aliphatic sulfonium salt, an aromatic sulfonium salt or an aromatic iodonium salt is added as a thermally latent or optically latent cation polymerization initiator to the resulting polymer, whereby a cross-linked polymer having a three-dimensional network structure can be prepared by cation polymerization. The examples of the aliphatic sulfonium salt which is the thermally latent cation polymerization initiator are 3-methyl-2-butenyltetramethylenesulfonium hexafluoroantimonate and 2-butenyltetramethylenesulfonium hexafluoroantimonate, and they are marketed from Asahi Denka Co., Ltd. Many products of the aromatic sulfonium salt which is the thermally latent or optically latent cation polymerization initiator are marketed from Sanshin Chemical Industry Co., Ltd. and Asahi Denka Co., Ltd. Diphenyl-4-thiophenoxyphenylsulfonium hexafluoroantimonate also is the example of the aromatic sulfonium salt. The example of the aromatic iodonium salt is (4-pentadecyloxyphenyl)phenyliodonium hexafluoroantimonate. When carrying out optically latent cation polymerization, a photosensitizer, for example, Adeka Optomer SP-100 (manufactured by Asahi Denka Co., Ltd.) may be used in combination. Also, when obtaining a cross-linked polymer having a three-dimensional network structure by cation polymerization, a monofunctional or multifunctional glycidyl base cross-linking agent or a monofunctional or multifunctional oxetane base cross-linking agent may be allowed to coexist.

Next, a refining method for the polymer (P-3) shall be explained. This compound is isolated and refined by efficiently removing the unreacted addition-polymerizable monomer. Various methods are available, and a refining method carried out by reprecipitation operation is preferred. This refining method is carried out in the following manner. First, a solvent which does not dissolve the polymer (P-3) but dissolves the unreacted monomer, a so-called precipitant is added to the polymerization reaction liquid containing the polymer (P-3) and the unreacted monomer to precipitate only the polymer (P-3). A preferred use amount of the precipitant is 20 to 50 times based on the weight of the polymerization reaction liquid described above.

The preferred precipitant is a solvent which is compatible with the polymerization solvent used in polymerization and which does not dissolve the polymer (P-3) at all but dissolves only the unreacted monomer and has a relatively low boiling point. The examples of the preferred precipitant are lower alcohols and aliphatic hydrocarbons. The particularly preferred precipitant is methanol and hexane. A repeating frequency of the reprecipitation operation is advisably increased in order to further raise a removing efficiency of the unreacted monomer. This method makes it possible to deposit only the polymer (P-3) in a poor solvent, and the polymer can readily be separated from the unreacted monomer by filtering operation.

The transition metal complex which is the polymerizing catalyst remains in the compound (P-3) isolated by the method described above, and therefore problems such as coloring of the polymer, influence on the physical properties and environmental safety are brought about in a certain case. Accordingly, this catalyst residue has to be removed in finishing the polymerization reaction. The catalyst residue can be removed by adsorbing treatment using activated carbon. The examples of adsorbents other than activated carbon are ion exchange resins (acid, basic or chelate form) and inorganic adsorbents. The inorganic adsorbents have a character of a solid acid, a solid base or neutrality. They are particles having a porous structure and therefore have a very high adsorbing ability. It is also one of the characteristics of the inorganic adsorbents that they can be used in a wide temperature range extending from a low temperature to a high temperature.

The examples of the inorganic adsorbents are silicon dioxide, magnesium oxide, silica-alumina, aluminum silicate, activated alumina, clay base adsorbents such as acid clay and activated clay, zeolite base adsorbents, dawsonites compounds and hydrotalcites compounds. Zeolite includes natural products and synthetic products, and either can be used. Kinds such as a crystal form, an amorphous form, a noncrystal form, a glass form, a synthetic product and a natural product are available for silicon dioxide, and silicon dioxide of a powder form can be used in the present invention regardless of the kind. The examples of natural aluminum silicate are pumice, fly ash, kaoline, bentonite, activated clay and diatomaceous earth. Synthetic aluminum silicate has a large specific surface area and a high adsorbing ability. The hydrotalcites compound is carbonate hydrate of aluminum-magnesium hydroxide.

The acid adsorbents and the basic adsorbents are preferably used in combination with activated carbon. The examples of the acid adsorbents are acid clay, activated clay and aluminum silicate. The examples of the basic adsorbents are activated alumina, the zeolite base adsorbents and the hydrotalcites compounds each described above. These adsorbents may be used alone or in a mixture of two or more kinds thereof. The polymer (P-3) produced by the atom transfer radical polymerization can be refined by bringing into contact with activated alumina. A commercial product available from Aldrich Co., Ltd. can be used as activated alumina. When adsorbing treatment is carried out by using activated alumina in combination with the other adsorbent, the adsorbents can be mixed and brought into contact with the compound, but they may be brought into contact at the separate steps respectively. When brought into contact with the adsorbent, the reaction liquid may be used as it is or may be diluted with a solvent. The diluent may be selected from usual solvents only on the condition that it is not a poor solvent for the polymer. A temperature for treating with the adsorbent shall not specifically be restricted. The treatment may be carried out usually at 0 to 200° C. The preferred temperature range is a room temperature to 180° C. A use amount of the absorbent falls in a range of 0.1 to 500% by weight based on the weight of the polymer (P-3). Considering the economical efficiency and the operability, the preferred range is 0.5 to 10% by weight.

A method of a batch system in which stirring-mixing and solid-liquid separation are carried out by batch operation can be used for solid-liquid contact of the absorbent and the polymer liquid. In addition thereto, capable of being used is a method of a continuous system such as a fixed layer system in which the polymer liquid is allowed to pass through a vessel charged with the adsorbent, a moving layer system in which the liquid is allowed to pass through a moving layer of the adsorbent and a fluidized layer system in which the adsorbent is fluidized by a liquid to carry out adsorption. Further, a mixing and dispersing operation carried out by stirring can be combined, if necessary, with an operation for elevating the dispersing efficiency, such as shaking of the vessel and use of a supersonic wave. After the polymer liquid is brought into contact with the absorbent, the absorbent is removed by a method such as filtering, centrifugal separation and settling separation, and washing treatment is carried out if necessary to obtain the refined polymer liquid. Treatment by the absorbent may be carried out for the polymer (P-3) which is the final product, and it may be carried out for an intermediate product used for producing this polymer. For example, in the respective polymerizing steps of the block copolymer obtained by the atom transfer radical polymerization, this polymer can be isolated and subjected to adsorbing treatment. The polymer (P-3) subjected to treatment by the adsorbent may be separated by depositing in a poor solvent or distilling off volatile components such as the solvent under reduced pressure.

The analytical methods of a molecular weight and a molecular weight distribution of the polymer (P-3) shall be explained. Usually, a molecular weight of an addition polymer can be measured by gel permeation chromatography (GPC) using a calibration curve in which a linear polymer such as polystyrene and poly(methyl methacrylate) is used as a standard sample. However, the polymer (P-3) belongs to a polymer of a vinyl base monomer originating in silsesquioxane, that is, a branched type-high molecular compound. Accordingly, when determining a molecular weight of the polymer (P-3) as it is, it is considered to involve a problem on an accuracy in molecular weight analysis to use a calibration curve in which a linear polymer such as polystyrene and poly(methyl methacrylate) is used as a standard sample. However, the polymer (P-3) has silsesquioxane at an end part thereof, and therefore it can readily be decomposed under an acid condition or a basic condition. That is, an accuracy in molecular weight analysis of a polymer part can further be enhanced by cutting off an addition polymer from silsesquioxane and then measuring the molecular weight thereof. Hydrofluoric acid is preferably used when decomposing the polymer (P-3) under an acid condition. Potassium hydroxide is preferably used when decomposing the polymer (P-3) under a basic condition. The polymer (P-3) can be decomposed in either of a homogeneous system and a heterogeneous system. For example, the silsesquioxane part of the polymer (P-3) can be decomposed in a homogeneous mixed system of an organic solvent (THF, acetonitrile and the like) which can dissolve the polymer (P-3) and hydrofluoric acid. The silsesquioxane part can be decomposed as well in a heterogeneous mixed system of toluene and hydrofluoric acid. In this case, a phase transfer catalyst is preferably used in combination. The examples of the phase transfer catalyst are benzyltrimethylammonium chloride, tetramethylammonium chloride, tetrabutylammonium bromide, trioctylammonium chloride, dioctylmethylammonium chloride, triethylamine and dimethylaniline. When using potassium hydroxide, decomposition can be carried out as well in a mixed solvent of THF, ethanol and water.

The addition polymer cut off by the above methods is measured by GPC, whereby a molecular weight of an addition polymer part in the polymer (P-3), a molecular weight of a so-called graft chain can be determined. It is possible as well to determine a molecular weight of the polymer (P-3) itself by using a universal calibration curve obtained from the viscosity and the GPC data. An absolute molecular weight of the polymer (P-3) can be determined as well by an end group determination method, a membrane osmotic pressure method, an ultracentrifugal method and a light scattering method.

A preferred molecular weight of the graft chain in the polymer (P-3) falls in a range of 500 to 1,000,000 for a number average molecular weight in terms of poly(methyl methacrylate). The more preferred range is 1,000 to 100,000. However, the upper limit value and the lower limit value in this range do not necessarily have a specific meaning. The molecular weight distribution falls preferably in a range of 1.01 to 2.0 in terms of a dispersion degree (Mw/Mn).

The molecular weight of the graft chain can be controlled by a proportion of the vinyl base monomer to an α-haloester group which is an initiating group. That is, a theoretical molecular weight of the graft chain in the polymer (P-3) can be predicted from a molar ratio of the vinyl base monomer/α-haloester group and a consumption rate of the monomer using the following calculation equation:

$$Mn = (\text{consumption rate(mole \%) of monomer}/100) \times MW_M \times (\text{molar ratio of vinyl base monomer to } \alpha\text{-haloester group}) + MW_I$$

In the above calculation equation, Mn is a theoretical number average molecular weight; $MW_M$ is a molecular weight of the vinyl base monomer; and $MW_I$ is a molecular weight of the α-haloester group. When intending to obtain a polymer having the number average molecular weight range described above, a molar ratio of the vinyl base monomer/α-haloester group can be selected from a range of about 2/1 to about 40000/1, preferably about 10/1 to about 5000/1. The above number average molecular weight can be controlled as well by changing the polymerization time.

Further, a theoretical molecular weight of the polymer (P-3) itself can be predicted as well from a molar ratio of the vinyl base monomer/the compound (1-3-2) and a consumption rate of the monomer using the following calculation equation:

$Mn=$(consumption rate(mole %)of monomer/100)× $MW_M$×(molar ratio of vinyl base monomer to compound(1-3-2))+$MW_I$ In the above calculation equation, Mn is a theoretical number average molecular weight; $MW_M$ is a molecular weight of the vinyl base monomer; and $MW_I$ is a molecular weight of the compound (1-3-2).

Any method of GPC, $^1$H-NMR and gas chromatography can be adopted as a method for determining a consumption rate (hereinafter referred to as "conversion rate") of the monomer.

The explanations described above regarding the polymer (P-3) can be applied to the polymer (P-1).

Next, a method for photopolymerizing the vinyl base monomer using the silicon compound having the dithiocarbamate group represented by Formula (2-2) as the initiator, a so-called photo initiator-transfer agent-terminator polymerizing method shall be explained. It is well known that in this photo initiator-transfer agent-terminator polymerization, the dithiocarbamate group is radically dissociated by light and has an excellent polymerization initiating ability and a sensitizing ability. It is well known as well that photopolymerization in this case is radical polymerization and that it is like living polymerization. These informations are disclosed in, for example, Polymer Bulletin, 11 (1984), 135- and Macromolecules, 19 (1986), 287-. Accordingly, the silicon compound of the present invention having a dithiocarbamate group can continue to maintain a polymerization initiating ability as long as irradiated with light, and it has a photopolymerization initiating ability for all radically polymerizable monomers.

It is known as well that a dithiocarbamate group has the respective functions of a polymerization initiator, a chain transfer agent and a photopolymerization terminator all together in photopolymerization, and the reaction mechanism thereof has already become clear. The compound (1-2) of the present invention having a dithiocarbamate group is dissociated into a radical on an alkylphenyl group bonded to the silicon compound and a dithiocarbamate radical by irradiating with light. Then, the radical on the alkylphenyl group takes part in the initiation of the reaction, and the dithiocarbamate radical takes part in the termination of the reaction. When irradiation with light is stopped or the monomer is exhausted, the dithiocarbamate radical is added to the growing end as a terminator to form again a dithiocarbamate group. Accordingly, the polymer thus formed can also be used as a polymer photoinitiator having a photopolymerization initiating ability. The silicon compound of the present invention having a dithiocarbamate group can initiate polymerization of a vinyl base monomer coexisting therewith by being decomposed by irradiating with a UV ray having a wavelength of 250 to 500 nm, preferably 300 to 400 nm having energy required for radically dissociating the dithiocarbamate group.

The form of carrying out the polymerization reaction can suitably be selected from bulk polymerization, solution polymerization, suspension polymerization, emulsion polymerization and bulk-suspension polymerization. A solvent used when producing by solution polymerization is preferably a solvent which has a small chain transfer constant and which can dissolve a vinyl base monomer and a polymer thereof. The examples of such preferred solvent are benzene, toluene, xylene, ethylbenzene, acetone, methyl ethyl ketone, methyl isobutyl ketone, ethyl acetate, methyl cellosolve, ethyl cellosolve, dimethylformamide, isopropyl alcohol, butanol, hexane and heptane. A solvent having no characteristic absorption in a UV ray area of 250 to 500 nm is rather preferred. The polymerization temperature falls in a range of 0 to 200° C., preferably a room temperature to 150° C., but it shall not specifically be restricted.

The photo initiator-transfer agent-terminator polymerization can be carried out under reduced pressure, atmospheric pressure or applied pressure according to the kind of the vinyl base monomer and the kind of the solvent. It is important to carry out the polymerization usually under environment of inert gas such as nitrogen and argon, for example, under flowing of inert gas. Oxygen dissolved in the polymerization system has to be removed in advance under reduced pressure, and therefore it is possible to transfer to a polymerization step as it is under reduced pressure after finishing the step of removing dissolved oxygen.

When using a compound (1-2-2) as an initiator, a polymer obtained by the method described above is represented by Formula (P-2). In the following explanations, the polymer represented by Formula (P-2) is shown as the polymer (P-2):

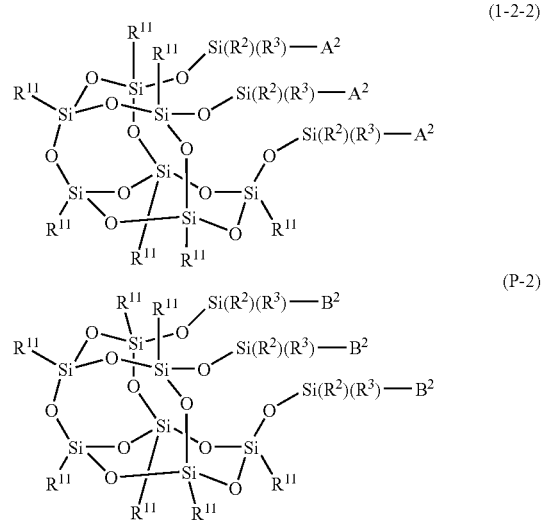

In the above formulas, $R^{11}$, $R^2$ and $R^3$ are groups defined in the same manner as in these codes in Formula (1-1-2). $A^2$ is a group represented by Formula (2-2), and $B^2$ is a group represented by Formula (2-2-P):

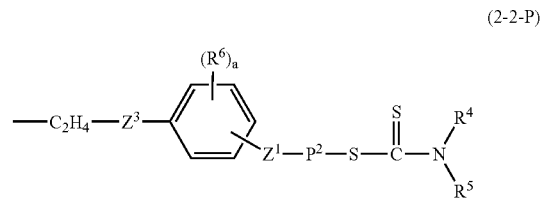

$P^2$ in the above formula is a group comprising the polymer of the vinyl base monomer, and the other codes have the same meanings as those of the codes in Formula (2-2). The bonding positions of $Z^1$ and $R^6$ on a benzene ring are the same as these bond positions in Formula (2-2).

The structure of the polymer (P-2) can be controlled by the same method as in obtaining the polymer (P-3) by the atom transfer radical polymerization method. Silsesquioxane to which a high branched type polymer is bonded can be obtained by using an initiator monomer, for example, N,N-diethyldithiocarbamoylmetylstyrene or N-ethyldithiocarbamoylmetylstyrene in combination in polymerizing a conventional vinyl base monomer. After copolymerized with a vinyl base monomer having an initiating group which does not take part in photo initiator-transfer agent-terminator polymerization, the vinyl base monomer is further polymerized in the other polymerization mode (for example, an atom transfer radical polymerization method) using the resulting polymer as an initiator, whereby a graft copolymer can be formed. The examples of the vinyl base monomer having an initiating group which does not take part in photo initiator-transfer agent-terminator polymerization are 1-(2-((4-ethenylphenyl)methoxy)-1-phenylethoxy-2, 2, 6, 6-tetramethylpyridine, 1-(meth)acryloxy-2-phenyl-2-(2,2,6,6-tetramethyl-1-piperidinyloxy)ethane, (1-(4-((4-(meth)acryloxy)ethoxyethyl)phenylethoxy)piperidine, 2-(2-bromopropanoyloxy)ethyl (meth)acrylate, 2-(2-bromoisobutyryloxy) ethyl (meth)acrylate, p-chloromethylstyrene, 2-(2-bromopropanoyloxy)styrene and 2-(2-bromoisobutyryloxy)styrene.

After finishing the photo initiator-transfer agent-terminator polymerization, the end dithiocarbamate group thereof is treated, whereby the polymer (P-2) can be deactivated against a UV ray. The examples of a deactivating method are a method in which the polymer (P-2) is treated in an acid solution or a basic solution, a method in which the polymer (P-2) is treated at a high temperature of 250° C. or higher for several minutes, a method in which the polymer is irradiated with an electromagnetic beam of high energy having a wavelength of 220 nm or less, a method in which a monomer having a UV ray-absorbing group is added and then photo-polymerized and a method in which a UV ray-absorbing agent is merely added. The end dithiocarbamate group can be substituted by adding a reagent having a large chain transfer constant (thiol derivatives, thiuram, xanthates and nitroxides) while irradiating the polymer (P-2) obtained with a UV ray.

A method for isolating and refining the polymer (P-2) shall be explained. This compound is isolated and refined by efficiently removing the unreacted vinyl base monomer. Various methods are available, and a refining method by the reprecipitating operation described above is preferred. This method makes it possible to precipitate only the polymer (P-2) in a poor solvent and readily separate the polymer from the unreacted monomer by filtering operation. The polymer may be isolated by distilling off volatile components such as the solvent and the unreacted monomer under a condition of reduced pressure. A preferred solvent for dissolving the polymer (P-2) is a solvent having a large dissolving power and a relatively low boiling point. A preferred precipitant is a solvent which is compatible with the solvent for the polymer (P-2) and does not dissolve at all the polymer (P-2) and which dissolves only the impurities or the unreacted monomer and has a relatively low boiling point. The examples of the preferred precipitant are lower alcohols and aliphatic hydrocarbons. The particularly preferred precipitant is methanol or hexane. It is advisable to increase the repeating frequency of the reprecipitating operation in order to further raise the refining degree.

A molecular weight and a molecular weight distribution of the polymer (P-2) can be analyzed by the same method as explained in the polymer (P-3). The polymer of the vinyl base monomer bonded to silsesquioxane, a so-called graft chain has a number average molecular weight falling in a range of 500 to 1,000,000. The more preferred range is 1,000 to 100,000. However, the upper limit value and the lower limit value in this range do not have a specific meaning. A molecular weight distribution of the graft chain falls preferably in a range of 1.01 to 3.0 in terms of a dispersion degree. It is possible as well to determine a molecular weight of the polymer (P-2) by using a universal calibration curve obtained from the viscosity and the GPC data. An absolute molecular weight of the polymer (P-2) can be determined as well by an end group determination method, a membrane osmotic pressure method, an ultracentrifugal method and a light scattering method. A molecular weight of the graft chain in the polymer (P-2) can be controlled in the same manner as in the case of the polymer (P-3)

PREFERRED EMBODIMENTS OF THE INVENTION

The present invention shall more specifically be explained with reference to examples, but the present invention shall not be restricted to the following examples.

Codes used in the examples mean the following.
Ph: phenyl
CH: cyclohexyl
CP: cyclopentyl
Et: ethyl
iBu: isobutyl
iOc: isooctyl
TFPr: trifluoropropyl
TDFOC: tridecafluoro-1,1,2,2-tetrahydrooctyl
TMS: trimethylsilyl
Mn: number average molecular weight
Mw: weight average molecular weight All the data of molecular weights in the examples were polystyrene-calibrated values determined by GPC (gel permeation chromatography). The measuring conditions of GPC are shown below. Apparatus: JASCO GULLIVER 1500 (intelligent differential refractometer RI-1530), manufactured by JASCO Corp.
Solvent: tetrahydrofuran (THF)
Flow velocity: 1 ml/minute
Column temperature: 40° C.
Columns used: the following columns (used connecting in series) manufactured by Tosoh Co., Ltd.
TSKguardcolumn HXL-L (GUARDCOLUMN)
TSKgel G1000HxL (excluded critical molecular weight (polystyrene): 1,000)
TSKgel G2000HxL (excluded critical molecular weight (polystyrene): 10,000)
Standard sample for calibration curve: Polymer Standards (PL), Polystyrene, manufactured by Polymer Laboratories Co., Ltd.

In Examples 7 to 34 and 109 to 114, Shodex KF-G (GUARDCOLUMN) and 2 columns of Shodex KF-804L (excluded critical molecular weight (polystyrene) 400,000) manufactured by Showa Denko K. K. were used connecting in series, and Shodex STANDARD M-75 (polymethyl methacrylate) manufactured by Showa Denko K. K. was used as a standard sample for a calibration curve. The other conditions are the same as described above.

EXAMPLE 1

<Synthesis of Compound (3-2-1): Phenylsilsesquioxane to which Sodium is Bonded>

A four neck separable flask having a content volume of 2 liter equipped with a reflux condenser, a thermometer and a dropping funnel was charged with ice and water (640.7 g) and toluene (200 g), and the inside of the flask was cooled to 0° C. while stirring. A mixed solution of phenyltrichlorosilane (211.5 g) And toluene (130 g) dried on molecular sieves for a whole day and nigh was dropwise added thereto in one hour so that a temperature in the inside of the flask did not exceed 2° C., and then the solution was further stirred at a room temperature for 30 minutes. The resulting reaction solution was washed with pure water, and low boiling components were distilled off by heating under reduced pressure to obtain a solid compound (120.7 g). This compound had a weight average molecular weight of about 3100 in terms of polystyrene measured by GPC. This is designated as a compound (A).

A 500 ml four neck flask equipped with a reflux condenser and a thermometer was charged with the compound (A) (12.9 g), THF (250 ml) dried on molecular sieves for a whole day and night and sodium hydroxide (4.0 g). This mixed solution was heated while stirring by means of a magnetic stirrer to maintain a reflux state at 67° C. After about 4 hours passed under heating and refluxing, the solution began to get cloudy by deposition of fine powder, and refluxing was further continued for one hour as it was to finish the reaction. A powder-like solid matter deposited was separated by filtration, and then it was washed with THF and dried under vacuum to obtain 10.1 g of a compound (A-1)

EXAMPLE 2

<Introduction of Trimethylsilyl Group into Compound (A-1)>

A four-neck flask of 200 ml equipped with a reflux condenser was charged with the compound (A-1) (2.0 g), toluene (100 g), triethylamine (1.7 g) and trimethylchlorosilane (1.4 g), and the mixture was stirred at a room temperature for 2 hours by means of a magnetic stirrer. After finishing the reaction, it was washed with pure water and dried under vacuum to obtain a compound (2.1 g) into which a trimethylsilyl group was introduced. This is designated as a compound (A-T).

The compound (A-T) was subjected to structural analysis by means of $^1$H-NMR, $^{13}$C-NMR, $^{29}$Si-NMR, mass spectrometry and IR analysis. It was confirmed from a $^1$H-NMR chart and a $^{13}$C-NMR chart that a phenyl group and a trimethylsilyl group were present in an integral ratio of 7:3. It was confirmed from $^{29}$Si-NMR that a peak of 11.547 ppm indicating a trimethylsilyl group was present and that three kinds of peaks of –77.574 ppm, –78.137 ppm and –78.424 ppm (all based on tetramethylsilane) indicating a T structure in which a phenyl group was bonded were present in a ratio of 1:3:3. It was confirmed from the measuring results of a mass spectrometric spectrum that the absolute molecular weight was consistent with a theoretical molecular weight of a chemical structural formula of Formula (3-2-T). Absorptions assigned respectively to deformation vibration of Si—Ph in 1430 cm$^{-1}$ and 1590 cm$^{-1}$, harmonic vibration of a substituted benzene ring in 1960 cm$^{-1}$ to 1760 cm$^{-1}$, stretching vibration of Si—O—Si in 1200 cm$^{-1}$ to 950 cm$^{-1}$ and vibration of Si—CH$_3$ in 1250 cm$^{-1}$ were confirmed from the measuring results of an IR absorption spectrum. These results support that the compound (A-T) has a structure represented by Formula (3-2-T). Accordingly, the compound (A-1) is a compound having a structure represented by Formula (3-2-1). The T structure is a term showing a partial structure in which three oxygen atoms are bonded to one silicon atom, that is, —Si(O—)$_3$.

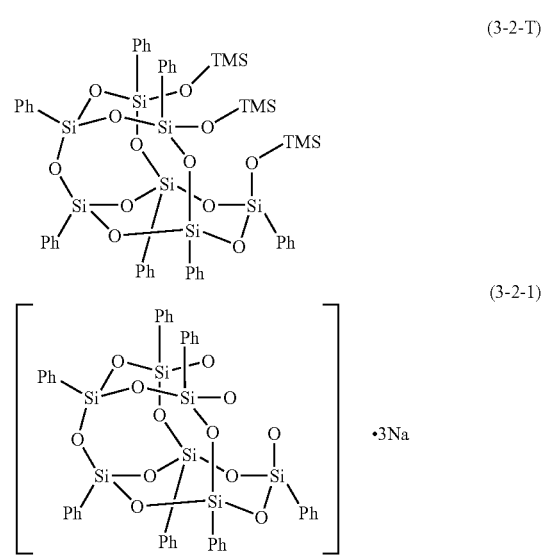

EXAMPLE 3

<Synthesis of Compound (5-1): Organic Silicon Compound Having a Hydrosilyl Group>

A three neck flask having a content volume of 50 ml equipped with a dropping funnel and a thermometer was charged with a rotator, the compound (3-2-1) (15.0 g) obtained by making use of the method in Example 1 and THF (85 g), and the flask was sealed with dry nitrogen. Dimethylchlorosilane (12.8 g) was dropwise added thereto from the dropping funnel in about 10 minutes while stirring by means of a magnetic stirrer. In this case, the dropping speed was controlled so that the content did not exceed 40° C. After finishing dropwise adding, stirring was continued at a room temperature for 3 hours to complete the reaction. Then, 30 g of pure water was added thereto while paying attentions so that the content did not exceed 40° C. to hydrolyze unreacted dimethylchlorosilane and dissolve sodium chloride. The reaction mixture thus obtained was transferred into a separating funnel to separate an organic layer from an aqueous layer. The organic layer thus obtained was washed with saturated brine, and then it was repeatedly washed with water so that the washing solution became neutral. The organic layer obtained was dried on anhydrous magnesium sulfate and concentrated under reduced pressure by means of a rotary evaporator to obtain 13.9 g of a white solid matter.

The structure of the white solid matter thus obtained was analyzed by means of gel permeation chromatography (GPC), $^1$H-NMR, $^{29}$Si-NMR and IR analysis. It was confirmed from a GPC chart that the white solid matter was monodispersed and that it had a weight average molecular weight of 1000 in terms of polystyrene. It was confirmed from a $^1$H-NMR chart that a phenyl group and a methyl group were present in an integral ratio of 15:6 and that a hydrosilyl group and a methyl group were present in an integral ratio of 1:6. It was confirmed from a $^{29}$Si-NMR chart that total four peaks of three kinds of peaks indicating a T structure having a phenyl group in –77.3, –77.6 and –78.2 ppm in an integral ratio of 1:3:3 and a peak indicating a dimethylsilyl group in –2.8 ppm were present. Absorptions assigned respectively to deformation vibration of Si—Ph in 1430 cm$^{-1}$ and 1590 cm$^{-1}$, harmonic vibration of a substituted benzene ring in 1960 to 1760 cm$^{-1}$ and stretching vibration of Si—H in 2139 cm$^{-1}$ were confirmed from an IR absorption spectrum measured by a KBr tablet method. These results indicate that the compound obtained by reacting the compound (3-2-1) with dimethylchlorosilane has a structure represented by Formula (5-1):

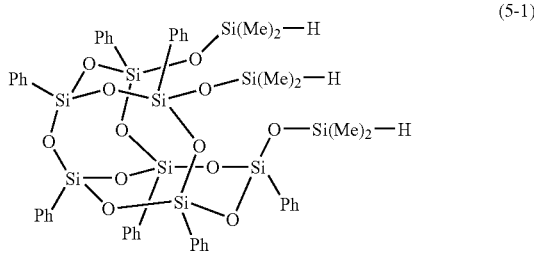

(5-1)

EXAMPLE 4

<Synthesis of Silicon Compound Having a Chloromethylphenylethyl Group>

A 1000 ml glass flask equipped with a stirrer, a reflux condenser, a thermometer and a dropping funnel was charged with the compound (5-1) (1.0 g, 2.7×10$^{-3}$ mole in terms of Si—H), chloromethylstyrene (0.5 g, 3.3×10$^{-3}$ mole), 4-tert-butylpyrocatechol (2.0 mg) and toluene (1.6 g). The flask was heated up to 60° C. on an oil bath while stirring under nitrogen atmosphere. Then, a platinum catalyst (Carsted catalyst: platinum divinyltetramethyldisiloxane complex-xylene solution, Pt content: 3% by weight, 8.7 μl) was introduced thereinto by means of a syringe to carry out hydrosilylation reaction. The reaction was traced by means of IR to result in confirming that absorption (ν=2270 cm$^{-1}$) based on Si—H disappeared after 4 hours passed, and it was regarded as a reaction end point. A 500 ml glass beaker was charged with 300 g of methanol, and the reaction solution described above was slowly dropwise added thereto while stirring and then left standing still in a freezing chamber (−35° C.) for a night. Thereafter, the solvent was removed by decantation, and then washing with methanol was further carried out twice. After recovering the precipitate, it was dissolved again in THF, and the solution was subjected to pressure filtration. Then, the solvent was removed by means of a rotary evaporator to obtain 1.0 g of a translucent viscous liquid (yield: 73%). The viscous liquid thus obtained was refined and separated by means of a column chromatography to obtain the intended compound. It was confirmed from the results of IR and NMR shown below that this compound was a silicon compound having a chloromethylphenylethyl group represented by Formula (11).

IR: ν=1267, 710 (C—Cl), 1170 to 1000 (Si—O—Si) cm$^{-1}$ $^1$H NMR (CDCl$_3$, CDCl$_3$ standard: δ=7.3 ppm): δ=6.8 to 7.8 (—C$_6$H$_4$—), 6.8 to 7.8 (Si—[C$_6$H$_5$]), 4.4 to 4.7 (—C$_6$H$_4$—[CH$_2$]—Cl), 2.6 to 2.7 (—Si—CH$_2$—[CH$_2$]—C$_6$H$_4$—), 2.2 to 2.4 (—Si—[CH]—CH$_3$—C$_6$H$_4$—), 1.3 to 1.5 (—Si—CH—[CH$_3$]—C$_6$H$_4$—), 0.8 to 1.1 (—Si—[CH$_2$]—CH$_2$—C$_6$H$_4$—), 0.0 to 0.4 ((—Si—[CH$_3$])$_2$—) ppm

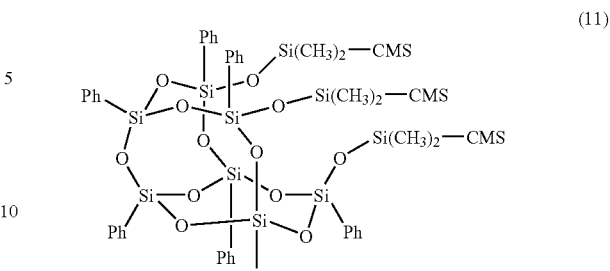

(11)

CMS in the above formula is a group represented by either of the following formulas:

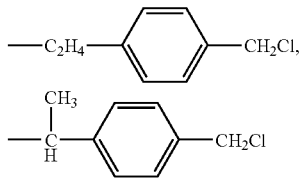

EXAMPLE 5

<Synthesis of Silicon Compound Having a Dithiocarbamoyl Group>

A 100 ml glass flask equipped with a stirrer, a sampling tube and a thermometer was charged with the compound (11) (1.42 g, 2.7×10$^{-3}$ mole in terms of a chloromethylphenethyl group) obtained in Example 4, sodium N,N-diethyldithiocarbamate-trihydrate (0.74 g, 3.24×10$^{-3}$ mole) and THF (60 ml) under a dry nitrogen gas atmosphere, and they were reacted while stirring. The reaction proceeded while generating heat, and sodium chloride was precipitated. The reaction was traced by means of IR to result in confirming that absorption (ν=710 (CH$_2$—Cl) cm$^{-1}$) based on a chloromethyl group disappeared after 5 hours passed. After finishing the reaction, an excess amount of water was added to the reaction solution, and the organic layer was extracted with diethyl ether. Then, the organic layer was separated and recovered, and the solvent was removed by means of a rotary evaporator. The recovered substance thus obtained was dissolved again in THF to subject the solution to pressure filtration, and then the solvent was removed by means of a rotary evaporator to obtain 1.50 g of a pale yellow viscous liquid (yield: 87%). This viscous liquid was refined by means of a column chromatography. As a result of measuring GPC before and after the reaction, a GPC peak based on the compound E was clearly shifted to a higher molecular weight side. All GPC peaks showed single peaks before and after the reaction, and no change was observed in the molecular weight distribution. It was confirmed from the results of IR and NMR shown below that this compound was a silicon compound having a dithiocarbamoyl group represented by Formula (12).

IR: ν=920 (C—S), 1210 (C—S), 1300 ([C—N]—C=S), 1485 ([N—C]=S) cm$^{-1}$ $^1$H NMR (CDCl$_3$): δ=7.0 to 7.4 (—C$_6$H$_4$—), 7.0 to 7.4 (Si—[C$_6$H$_5$]), 4.4 to 4.6 (—C$_6$H$_4$—[CH$_2$]—S—), 4.0 to 4.2, 3.6 to 3.8 (N-([CH$_2$] CH$_3$)$_2$), 2.5 to 2.7 (—Si—CH$_2$—[CH$_2$]—C$_6$H$_4$—), 2.2 to 2.4 (—Si—[CH]—CH$_3$—C$_6$H$_4$—), 1.3 to 1.4 (—Si—CH—[CH$_3$]—C$_6$H$_4$—), 1.2 to 1.3 (—Si—

CH$_2$—N(CH$_2$ [CH$_3$])$_2$), 0.8 to 1.1 (—Si—[CH$_2$]—CH$_2$—C$_6$H$_4$—), 0.0 to 0.3 ((—Si—[CH$_3$])$_2$—) ppm.

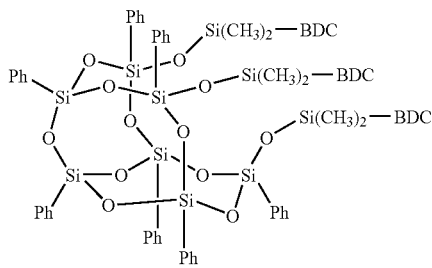
(12)

BDC in the above formula is a group represented by either of the following formulas:

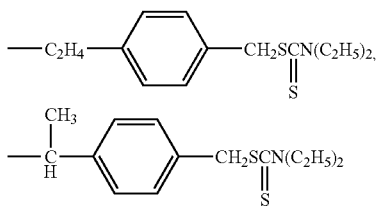

EXAMPLE 6

<Preparation of Solution (A) for Polymerization>

A 200 ml Schrenk tube equipped with a stirrer was charged with the compound (12) (0.17 g) obtained in Example 5, methyl methacrylate (6.4 ml), distilled toluene (13.9 ml) and decane (1.1 ml) under a dry nitrogen gas atmosphere in a draft in which a UV ray was cut, and the solution was sufficiently stirred at a room temperature to prepare a solution (A) for polymerization.

<Polymerization>

The solution (A) (3 ml) for polymerization was sampled by means of a glass-made syringe under a dry nitrogen gas atmosphere and introduced into a 4 ml glass ampul, and then it was subjected to freeze vacuum deaeration (pressure: $1 \times 10^{-2}$ Pa) by means of a high vacuum device equipped with a diffusion pump and sealed in a vacuum state by means of a hand burner. The sealed ampul was set in a rotary photopolymerizing apparatus (400 W extra-high pressure mercury lamp: UVL-400HA, manufactured by Riko Kagaku Sangyo Co., Ltd.), and photopolymerization was carried out to obtain a pale yellow viscous polymer solution. The polymerization conditions thereof were a light source distance: 150 mm, a UV ray illuminance (wavelength: 365 nm): 4.7 mW/cm$^2$, a rotating speed: 10 rpm and polymerization time: 10 minutes. This polymer solution was subjected to reprecipitation refining with hexane (100 ml), and then the precipitate was recovered by suction filtration. The precipitate was dried at 80° C. for 3 hours in a vacuum dryer to obtain 0.063 g of a polymer (a). The above polymer was subjected to GPC measurement, and the results thereof are shown in Table 14. The measurement was carried out on the following conditions.

Apparatus: JASCO GULLIVER 1500 (intelligent differential refractometer RI-1530) manufactured by JASCO Corp.
Solvent: THF
Flow velocity: 1 ml/min
Column temperature: 40° C.
Columns used: Shodex KF-G (GUARDCOLUMN+Shodex KF-804L (excluded critical molecular weight (polystyrene): 400000)×2 columns, manufactured by Showa Denko Co., Ltd.
Standard sample for calibration curve: poly(methyl methacrylate); Shodex STANDARD M-75

<Thermal Analysis>

A glass transition temperature and a thermal decomposition temperature of the polymer (a) were determined, and the results thereof are shown in Table 14. The measurements were carried out in the following conditions.

Glass transition temperature: a differential scanning type calorimeter DSC7 manufactured by Perkin Elmer Co., Ltd. was used. The programming rate: 10° C./min and the measuring temperature range: 10 to 180° C. Thermal decomposition temperature: a thermogravimetric apparatus TGA7 manufactured by Perkin Elmer Co., Ltd. was used. The programming rate: 20° C./min and the measuring temperature range: 50 to 800° C.

EXAMPLE 7

<Polymerization>

Photopolymerization was carried out in the same manner as in Example 6 to obtain 0.102 g of a polymer (b), except that the polymerization time was changed to 20 minutes. This polymer was subjected to GPC measurement, and the results thereof are shown in Table 14.

<Molecular Weight Measurement of Graft Chain>

A mixed solution of hydrofluoric acid (0.17 ml) and acetonitrile (0.83 ml) was prepared. The polymer (b) (15 mg) was dissolved in this mixed solution and stirred at a room temperature for 48 hours. Then, the solution was dried up at 80° C. for 3 hours in a vacuum dryer to recover the polymer. This polymer was subjected to GPC measurement, and the results thereof are shown below.
Number average molecular weight (Mn): 4000
Weight average molecular weight (Mw): 7000
Dispersion degree (Mw/Mn): 2.9

<Thermal Analysis>

The polymer (b) was subjected to thermal analysis in the same manner as in the polymer (a). The glass transition temperature measured by means of the differential scanning type calorimeter and the thermal decomposition temperature measured by the thermogravimetry are shown in Table 14.

EXAMPLE 8

<Polymerization>

Photopolymerization was carried out in the same manner as in Example 6 to obtain 0.129 g of a polymer (c), except that the polymerizing time was changed to 30 minutes. This polymer was subjected to GPC measurement, and the results thereof are shown in Table 14.

<Thermal Analysis>

The polymer (c) was subjected to thermal analysis in the same manner as in the polymer (a). The glass transition temperature measured by means of the differential scanning type calorimeter and the thermal decomposition temperature measured by the thermogravimetry are shown in Table 14.

EXAMPLE 9

<Polymerization>

Photopolymerization was carried out in the same manner as in Example 6 to obtain 0.181 g of a polymer (d), except that the polymerizing time was changed to 60 minutes. This polymer was subjected to GPC measurement, and the results thereof are shown in Table 14.

<Molecular Weight Measurement of Graft Chain>

A molecular weight of a graft chain in the polymer (d) was measured in the same manner as in the polymer (b), and the results thereof are shown below.
Number average molecular weight (Mn): 6000
Weight average molecular weight (Mw): 12000
Dispersion degree (Mw/Mn): 2.1

<Thermal Analysis>

The polymer (d) was subjected to thermal analysis in the same manner as in the polymer (a). The glass transition temperature measured by means of the differential scanning type calorimeter and the thermal decomposition temperature measured by the thermogravimetry are shown in Table 14.

EXAMPLE 10

<Polymerization>

Photopolymerization was carried out in the same manner as in Example 6 to obtain 0.255 g of a polymer (e), except that the polymerizing time was changed to 120 minutes. This polymer was subjected to GPC measurement, and the results thereof are shown in Table 14.

<Thermal Analysis>

The polymer (e) was subjected to thermal analysis in the same manner as in the polymer (a). The glass transition temperature measured by means of the differential scanning type calorimeter and the thermal decomposition temperature measured by the thermogravimetry are shown in Table 14.

EXAMPLE 11

<Polymerization>

Photopolymerization was carried out in the same manner as in Example 6 to obtain 0.307 g of a polymer (f), except that the polymerizing time was changed to 193 minutes. This polymer was subjected to GPC measurement, and the results thereof are shown in Table 14.

<Molecular Weight Measurement of Graft Chain>

A molecular weight of a graft chain in the polymer (f) was measured in the same manner as in the polymer (b), and the results thereof are shown below.
Number average molecular weight (Mn): 9000
Weight average molecular weight (Mw): 21000
Dispersion degree (Mw/Mn): 2.8

<Thermal Analysis>

The polymer (f) was subjected to thermal analysis in the same manner as in the polymer (a). The glass transition temperature measured by means of the differential scanning type calorimeter and the thermal decomposition temperature measured by the thermogravimetry are shown in Table 14.

EXAMPLE 12

<Polymerization>

Photopolymerization was carried out in the same manner as in Example 6 to obtain 0.491 g of a polymer (g), except that the polymerizing time was changed to 240 minutes. This polymer was subjected to GPC measurement, and the results thereof are shown in Table 14.

Thermal Analysis>

The polymer (g) was subjected to thermal analysis in the same manner as in the polymer (a). The glass transition temperature measured by means of the differential scanning type calorimeter and the thermal decomposition temperature measured by the thermogravimetry are shown in Table 14.

TABLE 14

| Example No. | Polymer No. | Number average molecular weight (Mn) | Weight average molecular weight (Mw) | Dispersion degree (Mw/Mn) | Tg (° C.) | Td (° C.) |
|---|---|---|---|---|---|---|
| 6 | (a) | 8,500 | 12,000 | 1.4 | 94 | 286 |
| 7 | (b) | 12,000 | 17,000 | 1.4 | 91 | 289 |
| 8 | (c) | 15,000 | 22,000 | 1.5 | 93 | 289 |
| 9 | (d) | 20,000 | 31,000 | 1.6 | 100 | 289 |
| 10 | (e) | 22,000 | 39,000 | 1.8 | 111 | 290 |
| 11 | (f) | 26,000 | 46,000 | 1.8 | 109 | 297 |
| 12 | (g) | 25,000 | 47,000 | 1.9 | 108 | 299 |

In Table 14, Tg is a glass transition temperature, and Td is a thermal decomposition temperature.

EXAMPLE 13

<Synthesis of Silicon Compound Having a Hydroxyethoxypropyl Group>

A 200 ml four neck flask equipped with a reflux condenser, a dropping funnel, a thermometer and a rotator was charged with the compound (5-1) (50.0 g) obtained by making use of the method of Example 3, ethylene glycol monoallyl ether (27.7 g) and toluene (77.7 g) and sealed with dry nitrogen. A platinum-divinyltetramethyldisiloxane complex/xylene solution (platinum content: 3.0% by weight, 14 µl) was added thereto at a room temperature by means of a microsyringe while stirring by means of a magnetic stirrer. The reaction proceeded while generating heat, and stirring was continued for 3 hours. Then, a part of the reaction solution was sampled and subjected to infrared absorption spectral analysis to result in confirming that a peak (2,130 cm$^{-1}$) assigned to Si—H disappeared, and therefore this time was regarded as a reaction end point. The reaction mixture obtained was concentrated under reduced pressure by means of a rotary evaporator. Methanol (176 g) was added to the resulting residue, and then powder activated carbon (0.58 g) was added thereto and stirred at a room temperature for 2 hours. This methanol solution was filtered, and the solution obtained was concentrated under reduced pressure to obtain a white solid mater (63.0 g, yield: 99.1%).

The white solid matter described above had a GPC purity of 97.1%, and it was found from the results of IR, $^{1}$H-NMR, $^{13}$C-NMR and $^{29}$Si-NMR each shown below that the above compound had a structure represented by Formula (13).

IR (KBr method): ν=3,450 (—OH), 1430 (Si—Ph), 1135 to 1090 (Si—Ph), 1090 to 1000 (Si—O—Si) cm$^{-1}$.

$^{1}$H NMR (400 MHz, CDCl$_3$ TMS standard: δ=0.0 ppm): 7.55 to 7.08 (m, 35H, Ph—Si), 3.65 (t, 6H, —[CH$_2$]—OH), 3.45 (t, 6H, —[CH$_2$]—O—C$_2$H$_4$—), 3.40 (t, 6H, —C$_3$H$_6$—O—[CH$_2$]—), 2.76 (t, 3H, —OH), 1.67 (tt, 6H, —CH$_2$—[CH$_2$]—CH$_2$—), 0.67 (t, 6H, Si—[CH$_2$]—), 0.27 (s, 18H, —OSi[(CH$_3$)$_2$]—).

$^{13}$C NMR (100 MHz, CDCl$_3$, TMS standard: δ=0.0 ppm): 133.8 to 127.4 (Ph—Si), 73.7 (—[CH$_2$]—O—C$_2$H$_4$—), 71.6 (—C$_3$H$_6$—O—[CH$_2$]—), 61.5 (—[CH$_2$]—OH), 23.0 (—CH$_2$— [CH$_2$]—CH$_2$—), 13.7 (Si—[CH2]—), -0.27 (—Osi[(CH$_3$)$_2$]—).

$^{29}$Si NMR (79 MHz, CDCl$_3$, TMS standard: δ=0.0 ppm): 12.05 (—O[Si] (CH$_3$)$_2$CH$_2$—), -77.42, -77.69, -78.06 (Ph—SiO$_{1.5}$).

(13)

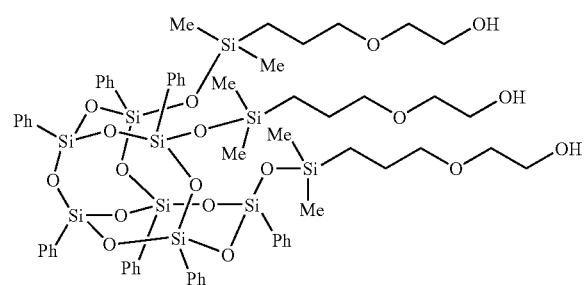

EXAMPLE 14

<Synthesis of Silicon Compound Having a 2-bromo-2-methylpropanoyloxyethoxypropyl Group>

A 100 ml Kjeldahl flask was charged with the compound (13) (3.0 g) obtained in Example 13, triethylamine (0.96 g) dried on molecular sieves (4a) and dry methylene chloride (35 ml) under argon atmosphere. The compound (13) was dissolved while stirring at a room temperature by means of a magnetic stirrer, and then the solution was cooled on a dry ice-methanol bath to maintain a solution temperature at -78° C. Then, 2-bromo-2-methylpropanoyl bromide (2.17 g, 4.5 equivalent based on the compound (13)) was quickly added to the above solution and stirred at -78° C. for one hour, and then the solution was further stirred at a room temperature for 2 hours. After finishing the reaction, triethylamine-hydrobromic acid salt was removed by filtration. Methylene chloride (100 ml) was added to the reaction solution obtained, and it was washed in order once with water (300 ml), twice with a sodium hydrogencarbonate aqueous solution (1%, 300 ml) and twice with water (300 ml), followed by drying it on anhydrous magnesium sulfate (5 g). Then, the above solution was concentrated at a room temperature by means of a rotary evaporator to reduce a liquid amount to about 5 ml. Methanol (50 ml) was added to this concentrate (5 ml) to subject a viscous liquid component to phase separation. Thereafter, it was left standing still in a freezing chamber to sufficiently subject the viscous liquid component to phase separation, and then this component was obtained by decantation. Methylene chloride (5 ml) was added to the viscous liquid component thus obtained to dissolve it again, and methanol (50 ml) was added thereto, whereby unreacted 2-bromo-2-methylpropanoyl bromide was removed by extraction. A large amount of methylene chloride was added to the viscous liquid component obtained to recover a methylene chloride-soluble part. The methylene chloride-soluble part thus obtained was concentrated at 40° C. for 6 hours under reduced pressure to obtain a transparent viscous liquid (1.087 g, yield: 27.8%)

The above transparent viscous liquid had a GPC purity of 99.1%, and it was found from the results of $^1$H-NMR, $^{13}$C-NMR and $^{29}$Si-NMR each shown below that the above compound had a structure represented by Formula (14).

$^1$H NMR (400 MHz, CDCl$_3$ TMS standard: δ=0.0 ppm): 7.55 to 7.09 (m, 35H, Ph—Si), 4.25 (t, 6H, —[CH$_2$]—O—(C=O)—), 3.57 (t, 6H, —[CH$_2$]—O—C$_2$H$_4$—), 3.35 (t, 6H, —C$_3$H$_6$—O—[CH$_2$]—), 1.91 (s, 18H, —C (Br) [(CH$_3$)$_2$]), 1.61 (tt, 6H, —CH$_2$— [CH$_2$]—CH$_2$—), 0.62 (t, 6H, Si—[CH$_2$]—), 0.27 (s, 18H, —OSi[(CH$_3$)$_2$]—)

$^{13}$C NMR (100 MHz, CDCl$_3$, TMS standard: δ=0.0 ppm): 171.5 (C=O), 133.8 to 127.4 (Ph—Si), 73.7 (—[CH$_2$]—O—C$_2$H$_4$—), 67.7 (—C$_3$H$_6$—O—[CH$_2$]—), 64.9 (—[CH$_2$]—O—(C=O)—), 55.4 (—[C](Br)(CH$_3$)$_2$), 30.5 (—C(Br) [(CH$_3$)$_2$]), 23.0 (—CH$_2$—[CH$_2$]—CH$_2$—), 13.6 (Si—[CH$_2$]—), -0.30 (—OSi[(CH$_3$)$_2$]—).

$^{29}$Si NMR (79 MHz, CDCl$_3$, TMS standard: δ=0.0 ppm): 11.98 (—O[Si](CH$_3$)$_2$CH$_2$—), -77.50, -77.84, -78.15 (Ph—SiO$_{1.5}$).

(14)

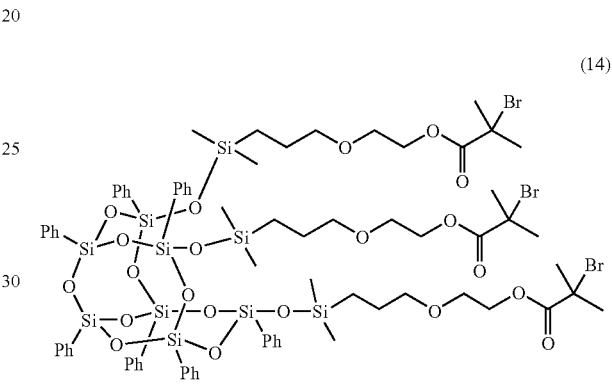

EXAMPLE 15

<Synthesis of Silicon Compound Having a Hydroxybutyl Group>

A 200 ml four neck flask equipped with a reflux condenser, a dropping funnel, a thermometer and a rotator was charged with the compound (5-1) (16.6 g) obtained by making use of the method of Example 3, 3-butene-1-ol (4.9 g) and toluene (21.5 g) and sealed with dry nitrogen. A platinum-divinyltetramethyl-disiloxane complex/xylene solution (platinum content: 3.0% by weight, 15 µl) was added thereto at a room temperature by means of a microsyringe while stirring by means of a magnetic stirrer. The reaction proceeded while generating heat. After continuing stirring for 3 hours, a part of the reaction solution was sampled and subjected to infrared absorption spectral analysis, and disappearance of a peak (2,130 cm$^{-1}$) assigned to Si—H was not confirmed. The platinum-divinyltetramethyldisiloxane complex/xylene solution (45 µl) was further added and stirred for 3 hours. Then, infrared absorption spectral analysis was carried out to result in confirming that a peak (2,130 cm$^{-1}$) assigned to Si—H disappeared, and therefore this time was regarded as a reaction end point. The reaction mixture obtained was concentrated under reduced pressure by means of a rotary evaporator to obtain a brown solid mater (19.5 g, yield: 98.5%)

The brown solid matter thus obtained had a GPC purity of 94.6%, and it was found from the results of $^1$H-NMR, $^{13}$C-NMR and $^{29}$Si-NMR each shown below that the above compound had a structure represented by Formula (15).

$^1$H NMR (400 MHz, DMSO-d$_6$, TMS standard: δ=0.0 ppm): 7.62 to 7.08 (m, 35H, Ph—Si), 4.38 (t, 3H, —OH), 3.40

(td, 6H, —[CH$_2$]—OH), 1.53 (tt, 6H, —[CH$_2$]—CH$_2$—OH), 1.37 (tt, 6H, Si—CH$_2$—[CH$_2$]—), 0.72 (tt, 6H, Si—[CH$_2$]—), 0.27 (s, 18H, —OSi[(CH$_3$)$_2$]—).

$^{13}$C NMR (100 MHz, DMSO-d$_6$, TMS standard: δ=0.0 ppm): 133.2 to 127.7 (Ph—Si), 60.3 (—[CH$_2$]—OH—), 36.1 (—[CH$_2$]—CH$_2$—OH), 19.0 (Si—CH$_2$— [CH$_2$]—), 17.3 (Si—[CH$_2$]—), –0.19 (—OSi[(CH$_3$)$_2$]—).

$^{29}$Si NMR (79 MHz, DMSO-d$_6$, TMS standard: δ=0.0 ppm): 12.57 (—O[Si](CH$_3$)$_2$CH$_2$—), –77.02, –77.64, –78.91 (Ph—SiO$_{1.5}$).

(15)

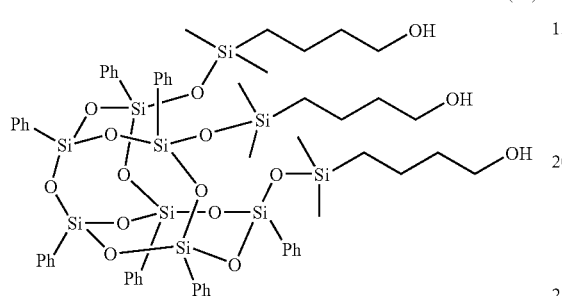

EXAMPLE 16

<Synthesis of Silicon Compound Having a 2-bromo-2-methylpropanoyloxybutyl Group>

A 100 ml Kjeldahl flask was charged with the compound (15) (1.5 g) obtained in Example 15, triethylamine (0.52 g) dried on molecular sieves (4a) and dry methylene chloride (13.5 g) under argon atmosphere. The compound E was dissolved while stirring at a room temperature by means of a magnetic stirrer, and then the solution was cooled on a dry ice-methanol bath to maintain a solution temperature at –78° C. Then, 2-bromo-2-methylpropanoyl bromide (1.17 g, 4.2 equivalent based on the compound (15)) was quickly added to the above solution and stirred at –78° C. for one hour, and then the solution was further stirred at a room temperature for 2 hours. After finishing the reaction, triethylamine-hydrobromic acid salt was removed by filtration. Methylene chloride (50 ml) was added to the reaction solution obtained, and it was washed in order once with water (150 ml), twice with a sodium hydrogencarbonate aqueous solution (1%, 150 ml) and twice with water (150 ml), followed by drying it on anhydrous magnesium sulfate (2.5 g). Then, the above solution was concentrated at a room temperature by means of a rotary evaporator to reduce a liquid amount to about 2.5 ml. Methanol (25 ml) was added to this concentrate (2.5 ml) to subject a viscous liquid component to phase separation. Thereafter, it was left standing still in a freezing chamber of –35° C. to sufficiently subject the viscous liquid component to phase separation, and then this component was obtained by decantation. Methylene chloride (2.5 ml) was added to the viscous liquid component thus obtained to dissolve it again, and methanol (25 ml) was added thereto, whereby unreacted 2-bromo-2-methylpropanoyl bromide was removed by extraction. A large amount of methylene chloride was added to the viscous liquid component obtained to recover a methylene chloride-soluble part. The methylene chloride-soluble part thus obtained was concentrated (40° C., 6 hours) under reduced pressure to obtain a transparent viscous liquid (0.37 g, yield: 18.4%)

The above compound had a GPC purity of 99.4%, and it was found from the results of $^1$H-NMR, $^{13}$C-NMR and $^{29}$Si-NMR each shown below that the above compound had a structure represented by Formula (16).

$^1$H NMR (400 MHz, CDCl$_3$ TMS standard: δ=0.0 ppm) 7.58 to 7.10 (m, 35H, Ph—Si), 4.06 (t, 6H, —[CH$_2$]—O—(C=O)—), 1.88 (s, 18H, —C(Br)[(CH$_3$)$_2$]), 1.63 (tt, 6H, —[CH$_2$]—CH$_2$—O—), 1.40 (tt, 6H, Si—CH$_2$— [CH$_2$]—), 0.65 (t, 6H, Si—[CH$_2$]—), 0.26 (s, 18H, —OSi[(CH$_3$)$_2$]—).

$^{13}$C NMR (100 MHz, CDCl$_3$, TMS standard: δ=0.0 ppm): 171.9 (C=O), 134.1 to 127.8 (Ph—Si), 65.8 (—[CH$_2$]—O—), 56.1 (—[C](Br)(CH$_3$)$_2$), 31.9 (—[CH$_2$]—CH$_2$—O—), 30.9 (—C(Br)[(CH$_3$)$_2$]), 19.5 (Si—CH$_2$— [CH$_2$]—), 17.6 (Si—[CH$_2$]—) 0.40 (—OSi[(CH$_3$)$_2$]—).

$^{29}$Si NMR (79 MHz, CDCl$_3$, TMS standard: δ=0.0 ppm): 12.53 (—O[Si](CH$_3$)$_2$CH$_2$—), —76.59, –76.91, –77.24 (Ph—SiO$_{1.5}$).

(16)

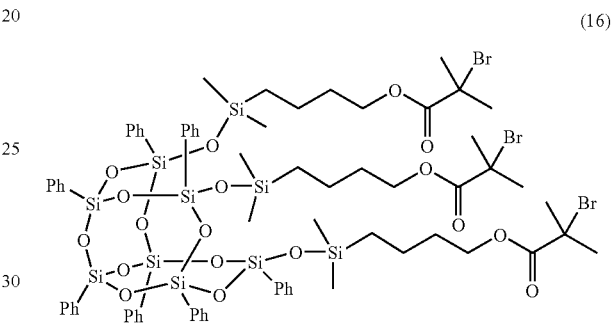

EXAMPLE 17

<Preparation of Solution for Polymerization>

Cuprous bromide was introduced into a heat resistant glass-made ampul in a draft which was cut off from a UV ray, and a compound (16)/methyl methacrylate/L-(–)-sparteine/anisole solution was further added thereto and quickly cooled using liquid nitrogen. Then, freezing vacuum deaeration (pressure: 1.0 Pa) was carried out three times by means of a vacuum device equipped with an oil-sealed rotary pump, and the ampul was quickly sealed by means of a hand burner while maintaining a state of vacuum. In this case, a proportion of the compound (16), methyl methacrylate, cuprous bromide and L-(–)-sparteine was set to 1:900:3:6 in terms of a molar ratio in the above order, and a use amount of anisole was set to such an amount that a concentration of methyl methacrylate became 50 wt %.

<Polymerization>

The sealed heat resistant glass-made ampul was set in a constant temperature-shaking bath, and polymerization was carried out to obtain a brown viscous solution of a polymer (1a). In this case, the polymerization temperature was 70° C., and the polymerization time was 1.0 hour. A monomer conversion rate in this polymerization reaction system was determined from the relation of a proton ratio of the respective substituents in the monomer and the polymer by diluting the solution of the polymer (1a) with deuterated chloroform and then subjecting the solution to $^1$H-NMR measurement. The polymer produced was recovered by reprecipitation refining from hexane, and a THF solution (1 wt %) of the polymer was prepared. This was allowed to pass through a column filled with activated alumina to thereby remove the copper complex by adsorption. Further, this solution was dropwise added to hexane to reprecipitate the polymer, and this was dried (80° C., 6 hours) under reduced pressure. Shown in Table 15 are the analytical results of a monomer conversion rate in the above polymerization reaction system, a theoretical number average molecular weight of the polymer (1a) derived from the monomer conversion rate, the number average molecular weight actually measured by GPC and the molecular weight distribution.

EXAMPLES 18 TO 21

Polymerization was carried out in the same manner as in Example 17 to obtain the respective brown viscous solutions of a polymer (1b) to a polymer (1e), except that the polymerization time was changed as shown in Table 15. Then, the respective polymers were refined in the same manner as in Example 17 to determine a monomer conversion rate, a theoretical number average molecular weight, a number average molecular weight and a molecular weight distribution of the polymers, and the results thereof are shown in Table 15.

TABLE 15

| Example | Polymer | Polymerization time (hr) | Conversion rate (mol %) | Mn*1 | Mn*2 | Mw/Mn*3 |
|---|---|---|---|---|---|---|
| 17 | 1a | 1.0 | 18.8 | 18,700 | 15,800 | 1.17 |
| 18 | 1b | 2.0 | 44.9 | 42,200 | 45,200 | 1.15 |
| 19 | 1c | 3.0 | 50.0 | 46,700 | 52,400 | 1.17 |
| 20 | 1d | 4.0 | 60.2 | 56,000 | 64,000 | 1.18 |
| 21 | 1e | 5.0 | 72.4 | 66,900 | 68,300 | 1.18 |

*1theoretical value
*2measured value
*3measured value

EXAMPLE 22

<Preparation of Solution for Polymerization>
Cuprous bromide was introduced into a heat resistant glass-made ampul in a draft which was cut off from a UV ray, and the compound (14) obtained in Example 14/methyl methacrylate/L-(−)-sparteine/anisole solution was further added and quickly cooled using liquid nitrogen. Then, freezing vacuum deaeration (pressure: 1.0 Pa) was carried out three times by means of a vacuum device equipped with an oil-sealed rotary pump, and the ampul was quickly sealed by means of the hand burner while maintaining a state of vacuum. In this case, a proportion of the compound (14), methyl methacrylate, cuprous bromide and L-(−)-sparteine was set to 1:900:3:6 in terms of a molar ratio in the above order, and a use amount of anisole was set to such an amount that a concentration of methyl methacrylate became 50 wt %.

<Polymerization>
The sealed heat resistant glass-made ampul was set in a constant temperature-shaking bath, and polymerization was carried out to obtain a brown viscous solution of a polymer (2a). In this case, the polymerization temperature was 70° C., and the polymerization time was 0.5 hour. A monomer conversion rate in this polymerization reaction system was determined from the relation of a proton ratio of the respective substituents in the monomer and the polymer by diluting the solution of the polymer (2a) with deuterated chloroform and then subjecting the solution to $^1$H-NMR measurement. The polymer produced was recovered by reprecipitation refining from hexane, and a THF solution (1 wt %) of the polymer was prepared. This was allowed to pass through a column filled with activated alumina to thereby remove the copper complex by adsorption. Further, this solution was dropwise added to hexane to reprecipitate the polymer, and it was dried (80° C., 6 hours) under reduced pressure. Shown in Table 16-1 are the analytical results of a monomer conversion rate in the above polymerization reaction system, a theoretical number average molecular weight of the polymer (2a) derived from the monomer conversion rate, the number average molecular weight actually measured by GPC and the molecular weight distribution.

<Analysis of Theoretical Molecular Weight of Graft Chain>
A theoretical molecular weight of the graft chain was calculated from the following equation assuming that an ester bond which was an initiating end in the polymerization was cut off by hydrolysis brought about by hydrofluoric acid treatment and that all terminating ends in the polymerization had become Br. The results thereof are shown in Table 16-2.

<Calculating Equation>

Theoretical Mn of graft chain=(monomer consumption rate (mole %)/100)×$MW_M$×(molar ratio of vinyl base monomer to α-bromoester group)+$MW_1$ <Parameters Used for Calculation>
$MW_M$=100 (methyl methacrylate)
Molar ratio of vinyl base monomer to α-bromoester group=300
$MW_1$=167.01 (BrC(CH$_3$)$_2$CO$_2$H)

<Molecular Weight Measurement of Graft Chain>
A mixed solution of hydrofluoric acid (0.17 ml) and acetonitrile (0.83 ml) was prepared. The polymer (2a) (10 mg) was dissolved in the above mixed solution in a polypropylene-made microtube (1.5 ml) into which a rotator was introduced, and the solution was stirred at 40° C. for 24 hours in an incubator equipped with a magnetic stirrer. Then, the solution was dried up at 80° C. for 3 hours in a vacuum dryer to recover the polymer. The polymer was subjected to GPC measurement, and the result thereof is shown in Table 16-2.

EXAMPLES 23 TO 27

Polymerization was carried out in the same manner as in Example 22 to obtain the respective brown viscous solutions of a polymer (2b) to a polymer (2f), except that the polymerization time was changed as shown in Table 16-1. Then, the respective polymers were refined in the same manner as in Example 22 to determine a monomer conversion rate, a theoretical number average molecular weight, a number average molecular weight and a molecular weight distribution of the polymers, and the results thereof are shown Table 16-1. Calculation of a theoretical number average molecular weight of the graft chain, treatment of the polymer by hydrofluoric acid and analysis of a number average molecular weight and a molecular weight distribution of the graft chain measured by GPC were carried out as well in the same manner as in Example 22, and the results thereof are shown Table 16-2.

TABLE 16-1

| Example | Polymer | Polymerization time (hr) | Conversion rate (mol %) | Mn*1 | Mn*2 | Mw/Mn*3 |
|---|---|---|---|---|---|---|
| 22 | 2a | 0.5 | 25.2 | 24,500 | 21,500 | 1.14 |
| 23 | 2b | 1.0 | 38.4 | 36,400 | 36,300 | 1.14 |

TABLE 16-1-continued

| Example | Polymer | Polymerization time (hr) | Conversion rate (mol %) | Mn*1 | Mn*2 | Mw/Mn*3 |
|---|---|---|---|---|---|---|
| 24 | 2c | 1.5 | 43.8 | 41,300 | 39,900 | 1.14 |
| 25 | 2d | 3.0 | 53.4 | 49,900 | 50,600 | 1.14 |
| 26 | 2e | 4.0 | 60.9 | 56,700 | 54,400 | 1.15 |
| 27 | 2f | 5.0 | 75.5 | 69,800 | 70,000 | 1.16 |

*1theoretical value
*2measured value
*3measured value

TABLE 16-2

(data of graft chain)

| Example | Polymer | Mn*1 | Mn*2 | Mw/Mn*3 |
|---|---|---|---|---|
| 22 | 2a | 7,700 | 8,600 | 1.13 |
| 23 | 2b | 11,700 | 12,600 | 1.15 |
| 24 | 2c | 13,300 | 14,200 | 1.14 |
| 25 | 2d | 16,200 | 17,000 | 1.20 |
| 26 | 2e | 18,400 | 19,900 | 1.19 |
| 27 | 2f | 22,800 | 24,900 | 1.14 |

*1theoretical value
*2measured value
*3measured value

EXAMPLE 28

<Preparation of Solution for Polymerization>

Cuprous bromide was introduced into a heat resistant glass-made ampul in a draft which was cut off from a UV ray, and the compound (14)/methyl methacrylate/L-(−)-sparteine/anisole solution was further added thereto and quickly cooled using liquid nitrogen. Then, freezing vacuum deaeration (pressure: 1.0 Pa) was carried out three times by means of a vacuum device equipped with an oil-sealed rotary pump, and the ampul was quickly sealed by means of the hand burner while maintaining a state of vaccum. In this case, a proportion of the compound (14), methyl methacrylate, cuprous bromide and L-(−)-sparteine was set to 1:450:3:6 in terms of a molar ratio in the above order, and a use amount of anisole was set to such an amount that a concentration of methyl methacrylate became 50 wt %.

<Polymerization>

The sealed heat resistant glass-made ampul was set in a constant temperature-shaking bath, and polymerization was carried out to obtain a brown viscous solution of a polymer (3a) In this case, the polymerization temperature was 70° C., and the polymerization time was 0.25 hour. A monomer conversion rate in this polymerization reaction system was determined from the relation of a proton ratio of the respective substituents in the monomer and the polymer by diluting the solution of the polymer (3a) with deuterated chloroform and then subjecting the solution to $^1$H-NMR measurement. The polymer produced was recovered by reprecipitation and refining from hexane, and a THF solution (1 wt %) of the above polymer was prepared. This was allowed to pass through a column filled with activated alumina to thereby remove the copper complex by adsorption. Further, this solution was dropwise added to hexane to reprecipitate the polymer, and it was dried (80° C., 6 hours) under reduced pressure. Shown in Table 17-1 are the analytical results of a monomer conversion rate in the above polymerization reaction system, a theoretical number average molecular weight of the polymer (3a) derived from the monomer conversion rate, the number average molecular weight actually measured by GPC and the molecular weight distribution.

<Analysis of Theoretical Molecular Weight of Graft Chain>

A theoretical molecular weight of the graft chain was calculated from the following equation assuming that an ester bond which was an initiating end in the polymerization was cut off by hydrolysis brought about by hydrofluoric acid treatment and that all terminating ends in the polymerization had become Br. The results thereof are shown in Table 17-2.

<Calculating Equation>

Theoretical Mn of graft chain=(monomer consumption rate (mole %)/100)×MW$_M$×(molar ratio of vinyl base monomer to α-bromoester group)+MW$_1$ <Parameters Used for Calculation>

MW$_M$=100 (methyl methacrylate)

Molar ratio of vinyl base monomer to α-bromoester group=150

MW$_1$=167.01 (BrC(CH$_3$)$_2$CO$_2$H)

<Molecular Weight Measurement of Graft Chain>

A mixed solution of hydrofluoric acid (0.17 ml) and acetonitrile (0.83 ml) was prepared. The polymer (3a) (10 mg) was dissolved in the above mixed solution in a polypropylene-made microtube (1.5 ml) into which a rotator was introduced, and the solution was stirred at 40° C. for 24 hours in an incubator equipped with a magnetic stirrer. Then, the solution was dried up at 80° C. for 3 hours in a vacuum dryer to recover the polymer. The polymer recovered was subjected to GPC measurement, and the results thereof are shown in Table 17-2.

EXAMPLES 29 TO 34

Polymerization was carried out in the same manner as in Example 28 to obtain the respective brown viscous solutions of a polymer (3b) to a polymer (3g), except that the polymerization time was changed as shown in Table 17-1. The respective polymers were refined in the same manner as in Example 28 to determine a monomer conversion rate, a theoretical number average molecular weight, a number average molecular weight and a molecular weight distribution, and the results thereof are shown in Table 17-1. Calculation of a theoretical number average molecular weight of the graft chain, treatment of the polymer by hydrofluoric acid and analysis of a number average molecular weight and a molecular weight distribution of the graft chain measured by GPC were carried out as well in the same manner as in Example 28, and the results thereof are shown in Table 17-2.

TABLE 17-1

| Example | Polymer | Polymerization time (hr) | Conversion rate (mol %) | Mn*1 | Mn*2 | Mw/Mn*3 |
|---|---|---|---|---|---|---|
| 28 | 3a | 0.3 | 24.1 | 12,700 | 12,000 | 1.15 |
| 29 | 3b | 0.5 | 36.3 | 18,200 | 16,900 | 1.15 |
| 30 | 3c | 1.0 | 46.0 | 22,600 | 22,700 | 1.15 |
| 31 | 3d | 1.5 | 59.8 | 28,800 | 29,000 | 1.15 |
| 32 | 3e | 2.0 | 71.5 | 34,000 | 33,800 | 1.17 |

TABLE 17-1-continued

| Example | Polymer | Polymerization time (hr) | Conversion rate (mol %) | Mn*1 | Mn*2 | Mw/Mn*3 |
|---|---|---|---|---|---|---|
| 33 | 3f | 2.5 | 73.0 | 34,700 | 35,700 | 1.16 |
| 34 | 3g | 3.0 | 81.5 | 38,500 | 40,700 | 1.17 |

*1theoretical value
*2measured value
*3measured value

TABLE 17-2

(data of graft chain)

| Example | Polymer | Mn*1 | Mn*2 | Mw/Mn*3 |
|---|---|---|---|---|
| 28 | 3a | 3,800 | 5,200 | 1.17 |
| 29 | 3b | 5,600 | 6,900 | 1.16 |
| 30 | 3c | 7,100 | 8,900 | 1.15 |
| 31 | 3d | 9,100 | 10,100 | 1.15 |
| 32 | 3e | 10,900 | 11,700 | 1.15 |
| 33 | 3f | 11,100 | 11,900 | 1.17 |
| 34 | 3g | 12,400 | 13,100 | 1.17 |

*1theoretical value
*2measured value
*3measured value

EXAMPLE 35

Synthesis of Phenylsilsesquioxane Compound (A-1) to which Sodium is Bonded Using Phenyltrimethoxysilane as a Raw Material>

A four neck flask having a content volume of one liter equipped with a reflux condenser, a therometer and a dropping funnel was charged with phenyltrimethoxyosilane (99 g), sodium hydroxide (10 g) and 2-propanol (500 ml), and a rotator was put thereinto. Deionized water 11 g was dropwise added thereto from the dropping funnel in about 2 minutes while stirring at a room temperature by means of a magnetic stirrer, and then the flask was heated on an oil bath up to a temperature at which 2-propanol was refluxed. After refluxing was started, stirring was continued for 1.5 hour to complete the reaction. Then, the flask was pulled up from the oil bath and left standing still a night at a room temperature to completely deposit a solid matter produced. The solid matter deposited was filtrated by means of a pressure filter equipped with a membrane filter having a pore diameter of 0.1 μm. Then, the solid matter thus obtained was washed once with 0.2-propanol and dried at 70° C. for 4 hours in a vacuum dryer to obtain a compound (A-1) (66 g) of a white solid matter.

EXAMPLE 36

<Introduction of Trimethylsilyl Group into Compound (A-1) Obtained Using Phenyltrimethoxysilane as a Raw Material>

A four neck flask having a content volume of 50 ml equipped with a dropping funnel, a reflux condenser and a thermometer was charged with a rotator, the compound (A-1) (1.2 g) obtained in Example 35, tetrahydrofuran (12 g) and triethylamine (1.8 g), and the flask was sealed with dry nitrogen. Chlorotrimethylosilane (2.3 g) was dropwise added thereto from the dropping funnel at a room temperature in about one minute while stirring by means of a magnetic stirrer. After finishing dropwise adding, stirring was continued at a room temperature for 3 hours to complete the reaction. Then, 10 g of pure water was added thereto to hydrolyze sodium chloride produced and unreacted chlorotrimethylsilane. The reaction mixture thus obtained was transferred into a separating funnel and separated into an organic phase and an aqueous phase, and the resulting organic phase was repeatedly washed with deionized water until the washing solution became neutral. The organic phase thus obtained was dried on anhydrous magnesium sulfate, filtered and concentrated under reduced pressure by means of a rotary evaporator to obtain a compound (A-T) (1.2 g) of a white solid matter.

The compound (A-T) was subjected to structural analysis by means of $^1$H-NMR, $^{13}$C-NMR, $^{29}$Si-NMR, mass spectrometry, X ray crystal structure analysis and IR analysis. It was confirmed from a $^1$H-NMR chart and a $^{13}$C-NMR chart that a phenyl group and a trimethylsilyl group were present in an integral ratio of 7:3. It was confirmed from $^{29}$Si-NMR that a peak of 11.547 ppm indicating a trimethylsilyl group was present and that three kinds of peaks of −77.574 ppm, −78.137 ppm and −78.424 ppm (all based on tetramethylsilane) having a phenyl group and indicating a T structure were present in a ratio of 1:3:3. It was confirmed from the measuring results of a mass spectrometric spectrum that an absolute molecular weight of the above compound was consistent with a theoretical molecular weight of the structural body represented by Formula (3-2-T) described above. It was indicated from the measuring results of the crystal structure analysis by X ray crystal structure analysis that the above compound was the structural body represented by Formula (3-2-T) described above. Confirmed from the measuring results of an IR absorption spectrum were absorptions assigned respectively to deformation vibration of Si—Ph in 1430 cm$^{-1}$ and 1590 cm$^{-1}$, harmonic vibration of a substituted benzene ring in 1960 to 1760 cm$^{-1}$, stretching vibration of Si—O—Si in 1200 to 950 cm$^{-1}$ and vibration of Si—CH$_3$ in 1250 cm$^{-1}$. These results support that the compound (A-T) to which a trimethylsilyl group is bonded has the structure represented by Formula (3-2-T) described above. This has made it apparent that the compound (A-1) has the structure represented by Formula (3-2-1) described above.

EXAMPLE 37

<Synthesis of Cyclohexylsilsesquioxane Compound to which Sodium is Bonded>

The same operation as in Example 35 is carried out, except that cyclohexyltrimethoxysilane is substituted for phenyltrimethoxyosilane, whereby a cyclohexylsilsesquioxane compound represented by Formula (17) to which sodium is bonded can be obtained.

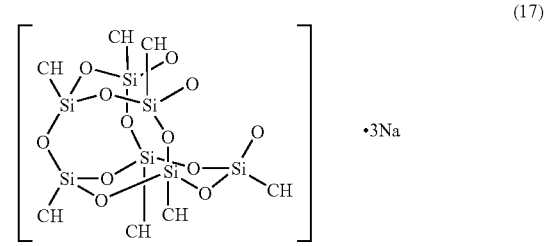

(17)

EXAMPLE 38

<Introduction of Trimethylsilyl Group into Compound (17)>

The same operation as in Example 4 is carried out, except that the compound (17) is substituted for the compound (A-1), whereby a cyclohexylsilsesquioxane compound having trimethylsilyl group represented by Formula (18-T) can be obtained. Further, it can be confirmed by subjecting the compound (18-T) to structural analysis by the same operation as in Example 36 that the compound (17) described above is produced.

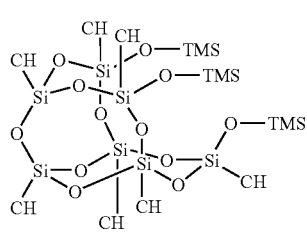

(18-T)

EXAMPLE 39

<Synthesis of Cyclopentylsilsesquioxane Compound to which Sodium is Bonded>

A four neck flask having a content volume of 200 ml equipped with a reflux condenser, a thermometer and a dropping funnel was charged with cyclopentyltrimethoxyosilane (19.0 g), THF (100 ml), sodium hydroxide (1.7 g) and deionized water (2.3 g), and the mixture was heated while stirring by means of a magnetic stirrer. After refluxing was started at 67° C., stirring was continued for 10 hours to finish the reaction. Then, the flask was pulled up from the oil bath and left standing still a night at a room temperature to completely deposit a solid matter produced. The solid matter deposited was filtered and dried under vacuum to obtain a compound of a powder-like solid matter (4.2 g).

EXAMPLE 40

<Introduction of Trimethylsilyl Group>

A four neck flask having a content volume of 100 ml equipped with a reflux condenser was charged with the compound (1.0 g) obtained in Example 39, THF (30 ml), triethylamine (0.5 g) and trimethylchlorosilane (0.7 g), and the mixture was stirred at a room temperature for 2 hours while stirring by means of a magnetic stirrer. After finishing the reaction, the same treatment as in confirming the structure in Example 36 was carried out to obtain a compound of a powder-like solid matter (0.9 g).

The compound thus obtained was analyzed by means of $^1$H-NMR, $^{29}$Si-NMR and X ray crystal structure analysis. It was confirmed from $^1$H-NMR that a cyclopentyl group and a trimethylsilyl group were present in an integral ratio of 7:3. Confirmed from $^{29}$Si-NMR were a peak of 8.43 ppm indicating a trimethylsilyl group and three kinds of peaks of –66.37 ppm, –67.97 ppm and –67.99 ppm having a cyclopentyl group and indicating a T structure. A ratio of the sum of the peak intensities of –67.97 ppm and –67.99 ppm to a peak intensity of –66.37 ppm was 6:1. It was confirmed from these results and the crystal structure obtained by the X ray crystal structure analysis that the compound of a powder-like solid matter which was the object of the analysis was a silicon compound represented by Formula (19). Accordingly, it was indicated that the compound obtained in Example 7 had a structure represented by Formula (20).

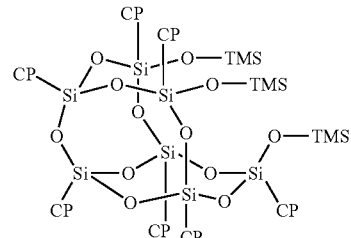

(19)

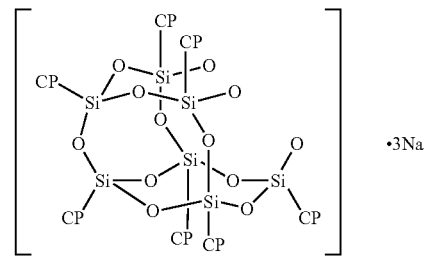

(20)

EXAMPLE 41

<Synthesis of Ethylsilsesquioxane Compound to which Sodium is Bonded>

The same operation as in Example 35 is carried out, except that ethyltrimethoxyosilane is substituted for phenyltrimethoxyosilane, whereby an ethylsilsesquioxane compound represented by Formula (21) to which sodium is bonded can be obtained.

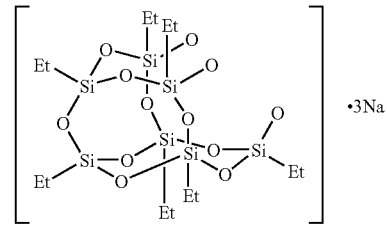

(21)

EXAMPLE 42

<Introduction of Trimethylsilyl Group into Compound (21)>

The same operation as in Example 36 is carried out, except that the compound (21) is substituted for the compound (A-1), whereby an ethylsilsesquioxane compound having a trimethylsilyl group represented by Formula (22) can be obtained. Further, it can be confirmed by subjecting the compound (22) to structural analysis by the same operation as in Example 4 that the compound (21) described above is produced.

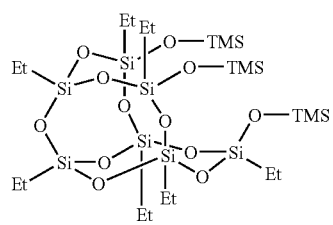

(22)

EXAMPLE 43

<Synthesis of Isobutylsilsesquioxane Compound to which Sodium is Bonded>

A four neck flask having a content volume of 200 ml equipped with a reflux condenser, a thermometer and a dropping funnel was charged with isobutyltrimethoxyosilane (18.7 g), THF (100 ml), sodium hydroxide (1.8 g) and deionized water (2.4 g), and the mixture was heated while stirring by means of a magnetic stirrer. After refluxing was started at 67° C., stirring was continued for 10 hours to finish the reaction. The reaction solution was concentrated under constant pressure until a solid matter was deposited, and then the resulting concentrate was left standing still a night at a room temperature to completely deposit the solid matter. This was filtered and dried under vacuum to obtain a compound of a powder-like solid matter (5.1 g).

EXAMPLE 44

<Introduction of Trimethylsilyl Group>

A four neck flask having a content volume of 200 ml equipped with a reflux condenser was charged with the compound of a powder-like solid matter (1.0 g) obtained in Example 43, THF (20 ml), triethylamine (0.5 g) and trimethylchlorosilane (0.8 g), and the mixture was stirred at a room temperature for 2 hours while stirring by means of a magnetic stirrer. After finishing the reaction, the same treatment as in confirming the structure in Example 4 was carried out to obtain a compound of a powder-like solid matter (0.9 g).

The powder-like solid matter described above was subjected to structural analysis by means of $^1$H-NMR and $^{29}$Si-NMR. It was confirmed from a $^1$H-NMR chart that an isobutyl group and a trimethylsilyl group were present in an integral ratio of 7:3. It was confirmed from $^{29}$Si-NMR that a peak of 8.72 ppm indicating a trimethylsilyl group was present and that three kinds of peaks of −67.38 ppm, −68.01 ppm and −68.37 ppm having an isobutyl group and indicating a T structure were present in a ratio of 1:3:3. It was confirmed from the above results that the compound of a powder-like solid matter which was the object of the analysis was a silicon compound represented by Formula (23). Accordingly, it was indicated that the compound obtained in Example 43 had a structure represented by Formula (24).

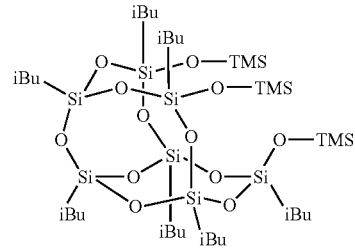

(23)

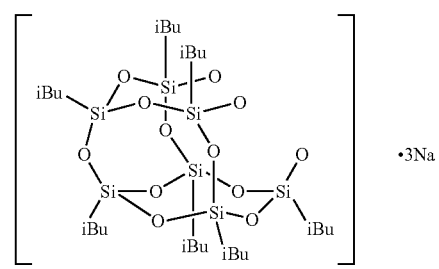

(24)

EXAMPLE 45

<Synthesis of Isooctylsilsesquioxane Compound to which Sodium is Bonded>

The same operation as in Example 35 is carried out, except that isooctyltrimethoxysilane is substituted for phenyltrimethoxyosilane, whereby an isooctylsilsesquioxane compound represented by Formula (25) to which sodium is bonded can be obtained.

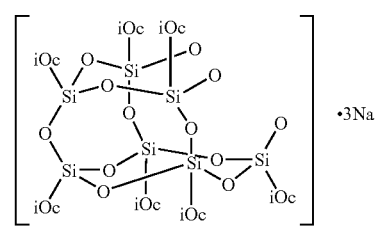

(25)

EXAMPLE 46

<Introduction of Trimethylsilyl Group into Compound (25)>

The same operation as in Example 36 is carried out, except that the compound (25) is substituted for the compound (A-1), whereby an isooctylsilsesquioxane compound having a trimethylsilyl group represented by Formula (26) can be obtained. Further, it can be confirmed by subjecting the compound (26) to structural analysis by the same operation as in Example 36 that the compound (25) described above is produced.

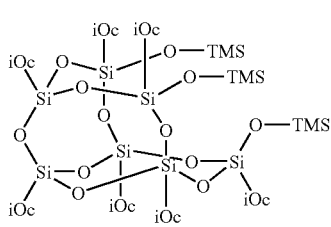

(26)

EXAMPLE 47

<Synthesis of Trifluoropropylsilsesquioxane Compound to which Sodium is Bonded>

A four neck flask having a content volume of 1 liter equipped with a reflux condenser, a thermometer and a dropping funnel was charged with trifluoropropyltrimethoxyosilane (100 g), THF (500 ml), deionized water (10.5 g) and sodium hydroxide (7.9 g), and the mixture was heated on an oil bath from a room temperature up to a temperature at which THF was refluxed while stirring by means of a magnetic stirrer. After refluxing was started, stirring was continued for 5 hours to complete the reaction. Thereafter, the flask was pulled up from the oil bath and left standing still a night at a room temperature, and then the flask was set again on the oil bath to heat and concentrate the reaction solution under constant pressure until a solid matter was deposited. The product deposited was filtrated through a pressure filter equipped with a membrane filter having a pore diameter of 0.5 μm. Then, the solid matter thus obtained was washed once with THF and dried at 80° C. for 3 hours in a vacuum dryer to obtain 74 g of a white power-like solid matter.

EXAMPLE 48

<Introduction of Trimethylsilyl Group>

A four neck flask having a content volume of 50 ml equipped with a dropping funnel, a reflux condenser and a thermometer was charged with the white power-like solid matter (1.0 g) obtained in Example 47, THF (10 g) and triethylamine (1.0 g), and the flask was sealed with dry nitrogen. Chlorotrimethylsilane (3.3 g) was dropwise added thereto at a room temperature in about one minute while stirring by means of a magnetic stirrer. After finishing dropwise adding, stirring was further continued at a room temperature for 3 hours to complete the reaction. Then, 10 g of pure water was added thereto to hydrolyze sodium chloride produced and unreacted chlorotrimethylsilane. The reaction mixture thus obtained was transferred into a separating funnel and separated into an organic phase and an aqueous phase, and the resulting organic phase was repeatedly washed with deionized water until the washing solution became neutral. The organic phase thus obtained was dried on anhydrous magnesium sulfate, filtered and concentrated under reduced pressure by means of a rotary evaporator to obtain a compound (0.9 g) of a white solid matter.

The white power-like solid matter thus obtained was subjected to structural analysis by means of GPC, $^1$H-NMR, $^{29}$Si-NMR and $^{13}$C-NMR. It was confirmed from a GPC chart that the white power-like solid matter showed a monodispersibility and that it had a weight average molecular weight of 1570 in terms of polystyrene and a purity of 98% by weight. It was confirmed from a $^1$H-NMR chart that a trifluoropropyl group and a trimethylsilyl group were present in an integral ratio of 7:3. It was confirmed from a $^{29}$Si-NMR chart that three peaks having a trifluoropropyl group and indicating a T structure were present in a ratio of 1:3:3 and that one peak indicating a trimethylsilyl group was present in 12.11 ppm. It was confirmed as well from a $^{13}$C-NMR chart that peaks indicating a trifluoropropyl group were present in 131 to 123 ppm, 28 to 27 ppm and 6 to 5 ppm and that a peak indicating a trimethylsilyl group was present in 1.4 ppm. It was confirmed from the result of a mass spectrometric spectrum that the absolute molecular weights were consistent with a theoretical molecular weight (m/z=1287) of a structural body represented by Formula (27), a theoretical molecular weight (m/z=1271) of a structural body in which one trimethylsilyl group was eliminated from the structural body represented by Formula (27) and a theoretical molecular weight (m/z=1189) of a structural body in which one trifluoropropyl group was eliminated from the structural body represented by Formula (27). It was indicated from the result of crystal structure analysis by X ray structure analysis that the compound produced was the structural body represented by Formula (27). These results show that the white power-like solid matter which is the object of the structural analysis has the structure of Formula (27). Accordingly, it is judged that the compound before trimethylsilylated has a structure of Formula (28).

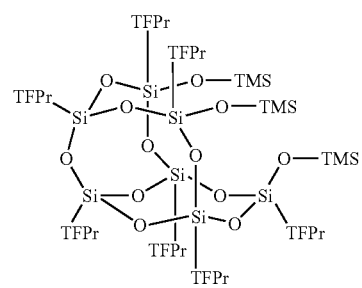

(27)

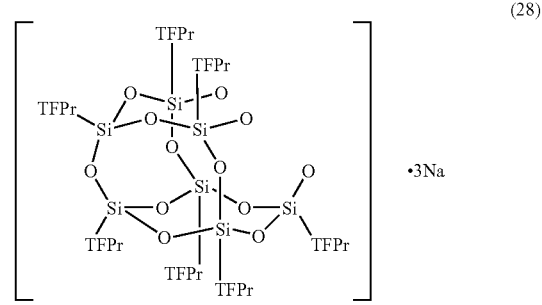

(28)

EXAMPLE 49

<Synthesis of Tridecafluoro-1,1,2,2-tetrahydrooctylsilsesquioxane Compound to which Sodium is Bonded>

A four neck flask having a content volume of 50 ml equipped with a reflux condenser, a thermometer and a dropping funnel was charged with tridecafluoro-1,1,2,2-tetrahydrooctyltriethoxysilane (4.9 g), THF (15 ml), sodium hydroxide (0.2 g) and ion-exchanged water (0.2 g), and a rotator was put thereinto to heat and reflux the mixture at 75° C. After refluxing was started, stirring was continued for 5 hours to finish the reaction. Then, it was concentrated under constant pressure by heating and dried at 80° C. for 3 hours in a vacuum dryer to obtain 4.0 g of a viscous liquid.

EXAMPLE 50

<Introduction of Trimethylsilyl Group>

A three neck flask having a content volume of 50 ml was charged with the viscous liquid (2.6 g) obtained in Example 49, THF (10 g), triethylamine (1.0 g) and trimethylchlorosilane (3.3 g), and the mixture was stirred at a room temperature for 3 hours while stirring by means of a magnetic stirrer. After finishing the reaction, the same treatment as in confirming the structure in Example 48 was carried out to obtain 1.3 g of a viscous liquid.

The compound thus obtained was analyzed by GPC. As a result of carrying out the measurement, it was confirmed that the viscous liquid was monodispersed and that it had a weight average molecular weight of 3650 (not corrected) in terms of polystyrene and a purity of 100%. Synthetically judging from the above result and the results obtained in Examples 35 to 48, it was estimated that the viscous liquid which was the object of the analysis was a silicon compound represented by Formula (29). Accordingly, it is indicated that the compound obtained in Example 49 has a structure represented by Formula (30).

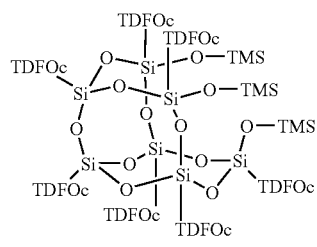
(29)

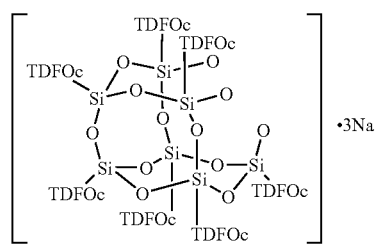
(30)

EXAMPLE 51

<Synthesis of Cyclohexylsilsesquioxane Having a Hydrosilyl Group>

The same operation as in Example 3 is carried out, except that the compound (17) obtained in Example 37 is substituted for the compound (A-1), whereby a compound represented by Formula (31) can be obtained.

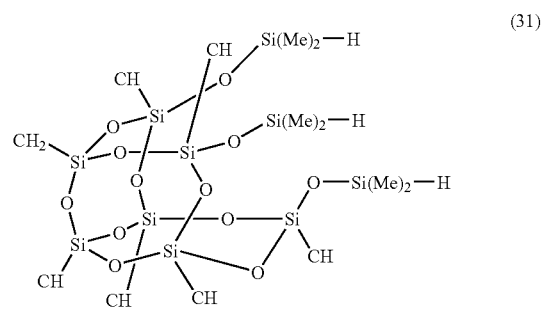
(31)

EXAMPLE 52

<Synthesis of Cyclopentylsilsesquioxane Having a Hydrosilyl Group>

The same operation as in Example 3 is carried out, except that the compound (20) obtained in Example 39 is substituted for the compound (A-1), whereby a compound represented by Formula (32) can be obtained.

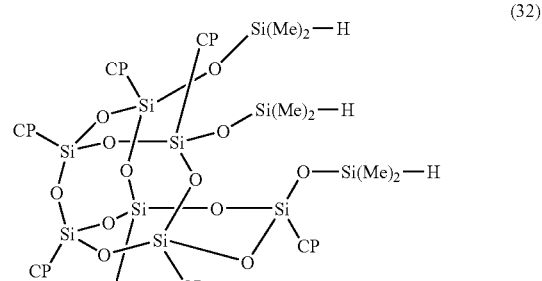
(32)

EXAMPLE 53

<Synthesis of Ethylsilsesquioxane Having a Hydrosilyl Group>

The same operation as in Example 3 is carried out, except that the compound (21) obtained in Example 41 is substituted for the compound (A-1), whereby a compound represented by Formula (33) can be obtained.

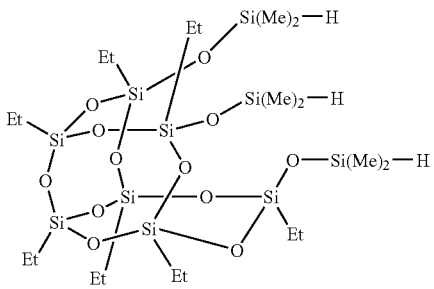

(33)

EXAMPLE 54

<Synthesis of Isobutylsilsesquioxane Having a Hydrosilyl Group>

The same operation as in Example 3 is carried out, except that the compound (21) obtained in Example 41 is substituted for the compound (A-1), whereby a compound represented by Formula (34) can be obtained.

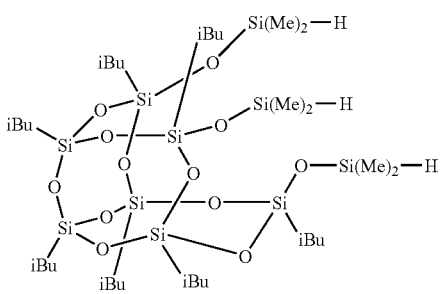

(34)

EXAMPLE 55

<Synthesis of Isooctylsilsesquioxane Having a Hydrosilyl Group>

The same operation as in Example 3 is carried out, except that the compound (24) obtained in Example 43 is substituted for the compound (A-1), whereby a compound represented by Formula (35) can be obtained.

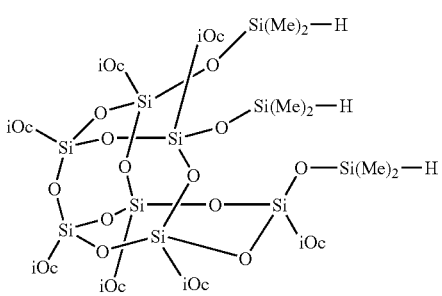

(35)

EXAMPLE 56

<Synthesis of Trifluoropropylsilsesquioxane Having a Hydrosilyl Group>

A reactor having a content volume of 300 ml equipped with a dropping funnel, a thermometer and a stirrer was charged with the compound (28) (10 g) obtained by making use of the method of Example 47 and a hydrochlorofluorocarbon base mixed solvent HCFC-225 (80 ml) and sealed with dry nitrogen. Chlorodimethylsilane (12.5 g) was dropwise added thereto in about 5 minutes while stirring at a room temperature. After finishing dropwise adding, the solution was heated so that a solution temperature was 50° C., and after reaching 50° C., stirring was continued for 5 hours. The solution was cooled until a solution temperature was 30° C. or lower, and then ion-exchanged water (60 g) was dropwise added thereto in about 5 minutes. After finishing dropwise adding, the solution was stirred for 10 minutes and then transferred into a separating funnel to separate an organic layer from an aqueous layer. The organic layer thus obtained was washed three times with each 60 g of ion-exchanged water. This organic layer was dried on anhydrous magnesium sulfate and concentrated under reduced pressure by means of a rotary evaporator to obtain a white powder-like solid matter (8.8 g, yield: 80.3%). The hydrochlorofluorocarbon base mixed solvent HCFC-225 described above is a mixture of $CF_3CF_2CHCl_2$ and $CClF_2CF_2CHClF$.

The above while powder-like solid matter had a GPC purity of 100%, a number average molecular weight of 1,430 and a weight average molecular weight of 1,440. It was found from the results of $^1$H-NMR, $^{13}$C-NMR and $^{29}$Si-NMR that the above compound had a structure represented by Formula (36).

IR (KBr method): $v_{v.s}$=2,140 (C=O), $v_{v.s}$=1,319, 1,215 (—$CF_3$), 1,090 to 1,000 (Si—O—Si) cm$^{-1}$.

$^1$H NMR (400 MHz, CDCl$_3$ TMS standard: δ=0.0 ppm): 4.79 (s, 3H, —OSi[H] (CH$_3$)$_2$), 2.11 (m, 14H, —[CH$_2$]—CF$_3$), 0.88 (m, 14H, Si—[CH$_2$]—CH$_2$—CF$_3$), 0.27 (s, 18H, —OSiH[(CH$_3$) 2]).

$^{13}$C NMR (100 MHz, CDCl$_3$, TMS standard: δ=0.0 ppm): 127.1 (—[CF$_3$]), 27.6(—[CH$_2$]—CF$_3$), 23.3 (—CH$_2$—[CH$_2$]—CH$_2$—), 13.8 (Si—[CH$_2$]—), 4.5 (Si—[CH$_2$]—CH$_2$—CF$_3$), −0.2 (—OSiH[(CH$_3$)$_2$]).

$^{29}$Si NMR (79 MHz, CDCl$_3$, TMS standard: δ=0.0 ppm): −2.38 (—O[Si]H(CH$_3$)$_2$), −66.39, −68.68, −69.20 (CF$_3$C$_2$H$_4$—SiO$_{1.5}$).

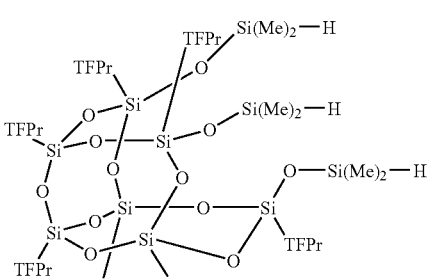

(36)

EXAMPLE 57

<Synthesis of Tridecafluoro-1,1,2,2-tetrahydrooctylsilsesquioxane Having a Hydrosilyl Group>

The same operation as in Example 56 is carried out, except that the compound (30) obtained in Example 50 is substituted for the compound (A-1), whereby a compound represented by Formula (37) can be obtained.

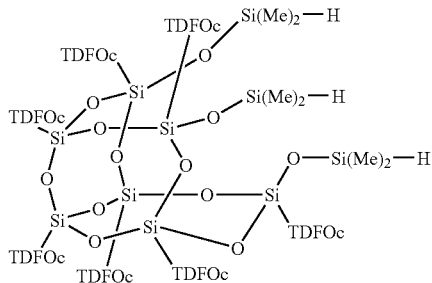

(37)

EXAMPLE 58

<Synthesis of Compound (5-1): Phenylsilsesquioxane Having a Hydrosilyl Group Using a Compound (38) as a Raw Material>

The compound (5-1) described in Example 3 can be obtained by a method in which a compound represented by Formula (38) (trisilanolphenyl POSS, manufactured by Hybrid Plastics Co., Ltd. In U.S.) used as a raw material is reacted with dimethylchlorosilane (1.0 equivalent or more based on silanol) in tetrahydrofuran in the presence of triethylamine (1.0 equivalent or more based on silanol).

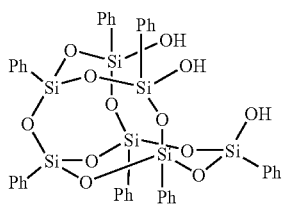

(38)

EXAMPLE 59

<Synthesis of Compound (31): Cyclohexylsilsesquioxane Having a Hydrosilyl Group Using a Compound (39) as a Raw Material>

The compound (31) described in Example 51 can be obtained by a method in which a compound represented by Formula (39) (trisilanolcyclohexyl POSS, manufactured by Hybrid Plastics Co., Ltd. in U.S.) used as a raw material is reacted with dimethylchlorosilane (1.0 equivalent or more based on silanol) in tetrahydrofuran in the presence of triethylamine (1.0 equivalent or more based on silanol).

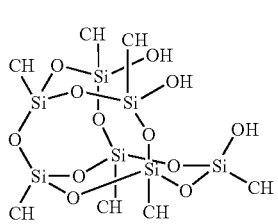

(39)

EXAMPLE 60

<Synthesis of Compound (32): Cyclopentylsilsesquioxane Having a Hydrosilyl Group Using a Compound (40) as a Raw Material>

The compound (32) described in Example 52 can be obtained by a method in which a compound represented by Formula (40) (trisilanolcyclopentyl POSS, manufactured by Hybrid Plastics U.S Co., Ltd. in U.S.) used as a raw material is reacted with dimethylchlorosilane (1.0 equivalent or more based on silanol) in tetrahydrofuran in the presence of triethylamine (1.0 equivalent or more based on silanol).

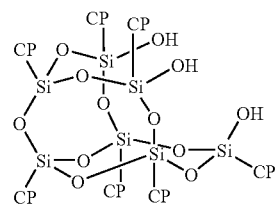

(40)

EXAMPLE 61

<Synthesis of Compound (33): Ethylsilsesquioxane Having a Hydrosilyl Group Using a Compound (41) as a Raw Material>

The compound (33) described in Example 53 can be obtained by a method in which a compound represented by Formula (41) (trisilanolethyl POSS, manufactured by Hybrid Plastics Co., Ltd. in U.S.) used as a raw material is reacted with dimethylchlorosilane (1.0 equivalent or more based on silanol) in tetrahydrofuran in the presence of triethylamine (1.0 equivalent or more based on silanol).

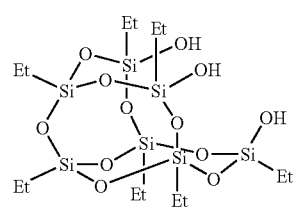

(41)

EXAMPLE 62

<Synthesis of Compound (34): Isobutylsilsesquioxane Having a Hydrosilyl Group Using a Compound (42) as a Raw Material>

The compound (34) described in Example 54 can be obtained by a method in which a compound represented by Formula (42) (trisilanolisobutyl POSS, manufactured by Hybrid Plastics Co., Ltd. in U.S.) used as a raw material is reacted with dimethylchlorosilane (1.0 equivalent or more based on silanol) in tetrahydrofuran in the presence of triethylamine (1.0 equivalent or more based on silanol).

(42)

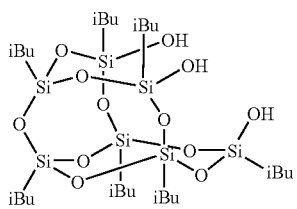

EXAMPLE 63

<Synthesis of Compound (35): Isooctylsilsesquioxane Having a Hydrosilyl Group Using a Compound (43) as a Raw Material>

The compound (35) described in Example 55 can be obtained by a method in which a compound represented by Formula (43) (trisilanolisooctyl POSS, manufactured by Hybrid Plastics Co., Ltd. in U.S.) used as a raw material is reacted with dimethylchlorosilane (1.0 equivalent or more based on silanol) in tetrahydrofuran in the presence of triethylamine (1.0 equivalent or more based on silanol).

(43)

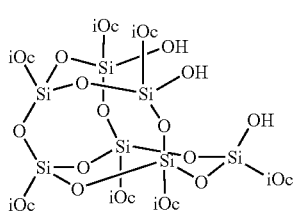

EXAMPLE 64

<Synthesis of Compound (36): Trtifluoropropylsilsesquioxane Having a Hydrosilyl Group Using a Compound (44) as a Raw Material>

A 300 ml four neck flask equipped with a dropping funnel, a reflux condenser, a thermometer and a rotator was set in an ice bath. The compound (28) 5 g obtained in Example 47 was put into the above four-neck flask and dissolved in butyl acetate (50 g), and then acetic acid (0.5 g) was dropwise added thereto. The flask was stirred for one hour in the ice bath. After put back to a room temperature, the reaction solution was washed (three times) with deionized-water (100 ml). The solvent was distilled off by means of a rotary evaporator, and the residue was dried (50° C., one hour) as it was under reduced pressure to obtain a viscous liquid (4.3 g). The compound thus obtained was subjected to GPC measurement to result in finding that a single peak was shown and that the presence of impurities was not confirmed. Further, analysis using IR was carried out to result in confirming absorption (in the vicinity of 3400 $cm^{-1}$) indicating the presence of a silanol group. Accordingly, it was indicated that the compound obtained had a structure represented by Formula (44).

(44)

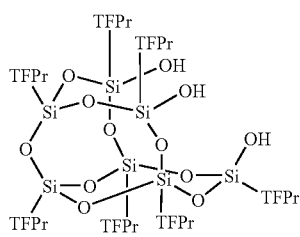

The compound (36) described in Example 56 can be obtained by a method in which the compound (44) described above used as a raw material is reacted with dimethylchlorosilane (1.0 equivalent or more based on silanol) in HCFC-225 in the presence of triethylamine (1.0 equivalent or more based on silanol).

EXAMPLE 65

<Synthesis of Compound (37): Tridecafluoro-1,1,2,2-tetrahydrooctylsilsesquioxane Having a Hydrosilyl Group Using a Compound (45) as a Raw Material>

The same operation as in Example 64 is carried out, except that the compound (30) obtained in Example 50 is substituted for the compound (28) obtained in Example 47, whereby a compound represented by Formula (45) can be obtained.

(45)

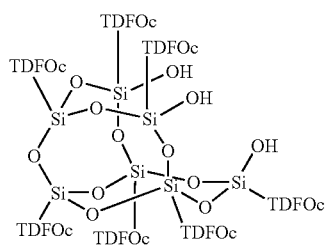

The compound (37) described in Example 57 can be obtained by a method in which the compound (45) described above used as a raw material is reacted with dimethylchlorosilane (1.0 equivalent or more based on silanol) in HCFC-225 in the presence of triethylamine (1.0 equivalent or more based on silanol).

EXAMPLE 66

<Synthesis of Compound (11): Silsesquioxane Having a Chloromethylphenylethyl Group>

The same operation as in Example 4 is carried out, except that used is the compound (5-1) described in Example 3 which is derived using the compound (38) described above as a raw material, whereby the compound represented by Formula (11) which is described in Example 4 can be derived. Then, the silicon compound having a dithiocarbamoyl group represented by Formula (12) described above can be obtained by the same operation as in Example 5 using the above compound (11) as a raw material.

EXAMPLES 67 TO 72

The silsesquioxane compounds having a hydrosilyl group which are derived by the methods described in Examples 51 to 56 or Examples 59 to 64 are used as raw materials to carry out the same operation as in Example 4, whereby silsesquioxanes having a chloromethylphenylethyl group represented by Formula (46) and shown in Table 18 can be derived.

TABLE 18

| Example No. | Compound name | $R^{12}$ | Raw material compound |
| --- | --- | --- | --- |
| 67 | Compound (46-1) | CH | Compound (31) |
| 68 | Compound (46-2) | CP | Compound (32) |
| 69 | Compound (46-3) | Et | Compound (33) |
| 70 | Compound (46-4) | iBu | Compound (34) |
| 71 | Compound (46-5) | iOc | Compound (35) |
| 72 | Compound (46-6) | TFPr | Compound (36) |

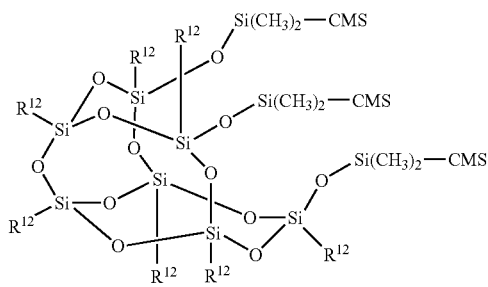

(46)

EXAMPLE 73

The same operation as in Example 4 is carried out, except that the compound (37) is used as a raw material and that the solvent is changed from toluene to HCFC-225, whereby silsesquioxane having a chloromethylphenylethyl group represented by Formula (46-7) can be derived.

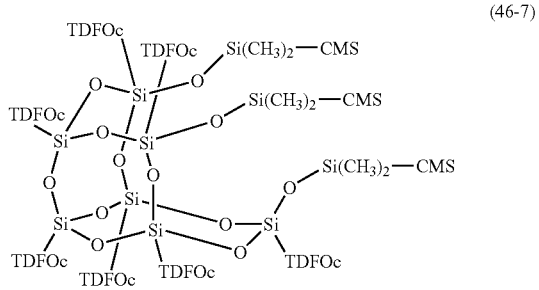

(46-7)

EXAMPLES 74 TO 78

The silsesquioxane compounds having a hydrosilyl group which are derived by the methods described in Examples 51 to 55 or Examples 59 to 63 are used as raw materials to carry out the same operation as in Example 13, whereby silsesquioxanes having a hydroxyethoxypropyl group represented by Formula (47) and shown in Table 19 can be derived.

TABLE 19

| Example No. | Compound name | $R^{12}$ | Raw material compound |
| --- | --- | --- | --- |
| 74 | Compound (47-1) | CH | Compound (31) |
| 75 | Compound (47-2) | CP | Compound (32) |
| 76 | Compound (47-3) | Et | Compound (33) |
| 77 | Compound (47-4) | iBu | Compound (34) |
| 78 | Compound (47-5) | iOc | Compound (35) |

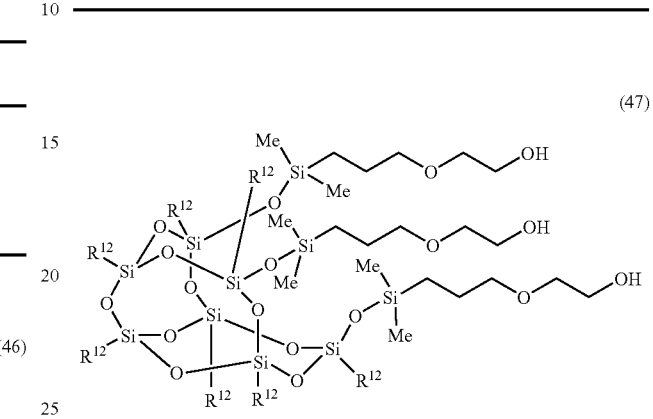

(47)

EXAMPLE 79

<Synthesis of Compound (47-6): Heptatrifluoropropylsilsesquioxane Having a Hydroxyethoxypropyl Group>

A reactor having a content volume of 100 ml equipped with a dropping funnel, a thermometer and a stirrer was charged with the compound (29) (2.5 g), ethylene glycol monoallyl ether (2.7 g) and toluene (3.0 g) and sealed with dry nitrogen. A platinum divinyltetramethyldisiloxane complex (17 μl) was added thereto at a room temperature by means of a microsyringe while stirring by means of a magnetic stirrer. After stirring was further continued for 2 hours, the reaction solution was sampled and subjected to infrared absorption spectral analysis to confirm that a peak of 2,130 cm$^{-1}$ originating in Si—H disappeared, and it was regarded as an end point of the reaction. The reaction solution was concentrated under reduced pressure by means of a rotary evaporator to obtain 2.6 g of a brown viscous liquid.

The above transparent viscous liquid had a GPC purity of 99.9%, a number average molecular weight of 1,790 and a weight average molecular weight of 1,910. It was found from the results of $^1$H-NMR, $^{13}$C-NMR and $^{29}$Si-NMR that the above compound had a structure represented by Formula (47-6).

IR (KBr method): $v_s$=3,450 (—OH), $v_{v.s}$=1,319, 1,215 (—CF$_3$), 1,090 to 1,000 (Si—O—Si) cm$^{-1}$.

$^1$H NMR (400 MHz, CDCl$_3$ TMS standard: δ=0.0 ppm): 3.69 (broad, 6H, —[CH$_2$]—OH), 3.51 (t, 6H, —[CH$_2$]—O—C$_2$H$_4$—), 3.41 (t, 6H, —C$_3$H$_6$—O—[CH$_2$]—), 2.70 (broad, 3H, —OH), 2.05 (m, 14H, —[CH$_2$]—CF$_3$), 1.60 (tt, 6H, —CH$_2$— [CH$_2$]—CH$_2$—), 0.82 (m, 14H, Si—[CH$_2$]—CH$_2$—CF$_3$), 0.60 (t, 6H, Si—[CH$_2$]—), 0.14 (s, 18H, —OSi[(CH$_3$)$_2$]—).

$^{13}$C NMR (100 MHz, CDCl$_3$, TMS standard: δ=0.0 ppm): 126.9 (—[CF$_3$]), 73.4 (—[CH$_2$]—O—C$_2$H$_4$—), 71.7 (—C$_3$H$_6$—O—[CH$_2$]—), 61.5 (—[CH$_2$]—OH), 27.6 (—[CH$_2$]—CF$_3$), 23.0 (—CH$_2$— [CH$_2$]—CH$_2$—), 13.6 (Si—[CH$_2$]—), 4.5 (Si—[CH$_2$]—CH$_2$—CF$_3$), -0.25 (—OSi[(CH$_3$)$_2$]).

$^{29}$Si NMR (79 MHz, CDCl$_3$, TMS standard: δ=0.0 ppm): 12.27 (—O[Si](CH$_3$)$_2$CH$_2$—), −66.75, −68.76, −69.92 (CF$_3$C$_2$H$_4$—SiO$_{1.5}$).

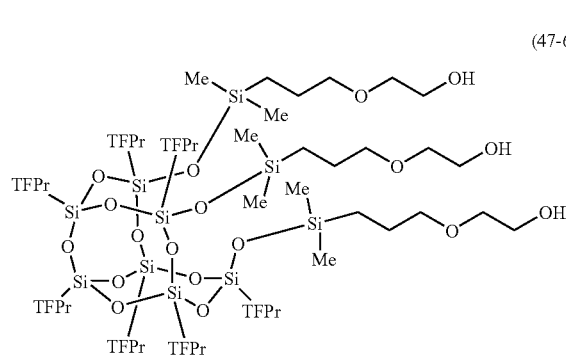

(47-6)

EXAMPLE 80

The same operation as in Example 13 is carried out, except that the compound (37) is used as a raw material and that the solvent is changed from toluene to HCFC-225, whereby silsesquioxane having a hydroxyethoxypropyl group represented by Formula (47-7) can be derived.

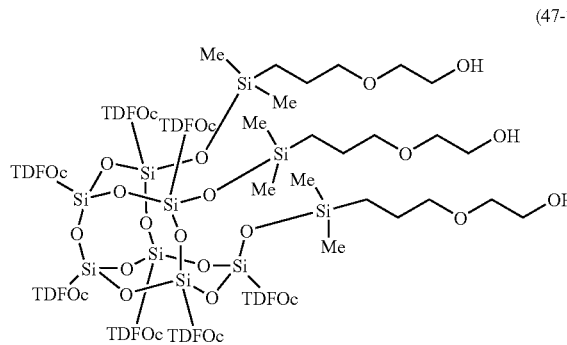

(47-7)

EXAMPLES 81 TO 86

<Synthesis of Silane Compounds Having a Hydroxybutyl Group>

The silsesquioxane compounds having a hydrosilyl group which are derived by the methods described in Examples 51 to 56 or Examples 59 to 64 are used as raw materials to carry out the same operation as in Example 15, whereby silsesquioxanes having a hydroxybutyl group represented by Formula (48) and shown in Table 20 can be derived.

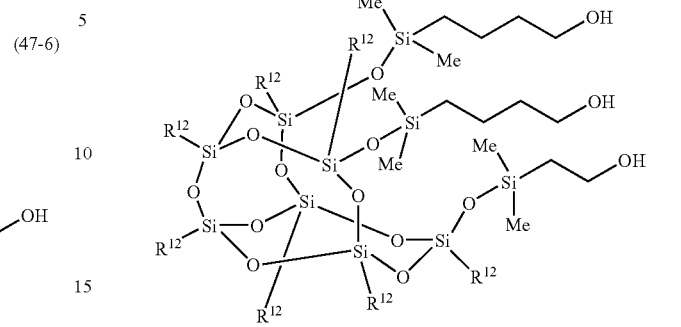

(48)

EXAMPLE 87

The same operation as in Example 15 is carried out, except that the compound (37) is used as a raw material and that the solvent is changed from toluene to HCFC-225, whereby silsesquioxane having a hydroxybutyl group represented by Formula (48-7) can be derived.

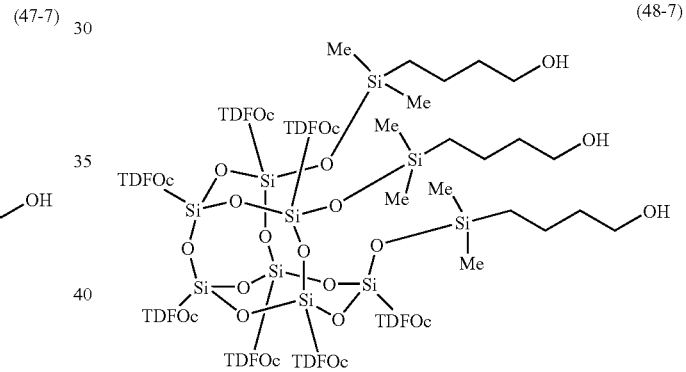

(48-7)

EXAMPLES 88 TO 92

The silsesquioxanes having a hydroxyethoxypropyl group which are derived by the methods described in Examples 74 to 78 are used as raw materials to carry out the same operation as in Example 14, whereby silane compounds having a 2-bromo-2-methylpropanoyloxyethoxypropyl group represented by Formula (49) and shown in Table 21 can be synthesized.

TABLE 20

| Example No. | Compound name | R$^{12}$ | Raw material compound |
|---|---|---|---|
| 81 | Compound (48-1) | CH | Compound (31) |
| 82 | Compound (48-2) | CP | Compound (32) |
| 83 | Compound (48-3) | Et | Compound (33) |
| 84 | Compound (48-4) | iBu | Compound (34) |
| 85 | Compound (48-5) | iOc | Compound (35) |
| 86 | Compound (48-6) | TFPr | Compound (36) |

TABLE 21

| Example No. | Compound name | R$^{12}$ | Raw material compound |
|---|---|---|---|
| 88 | Compound (49-1) | CH | Compound (47-1) |
| 89 | Compound (49-2) | CP | Compound (47-2) |
| 90 | Compound (49-3) | Et | Compound (47-3) |
| 91 | Compound (49-4) | iBu | Compound (47-4) |
| 92 | Compound (49-5) | iOc | Compound (47-5) |

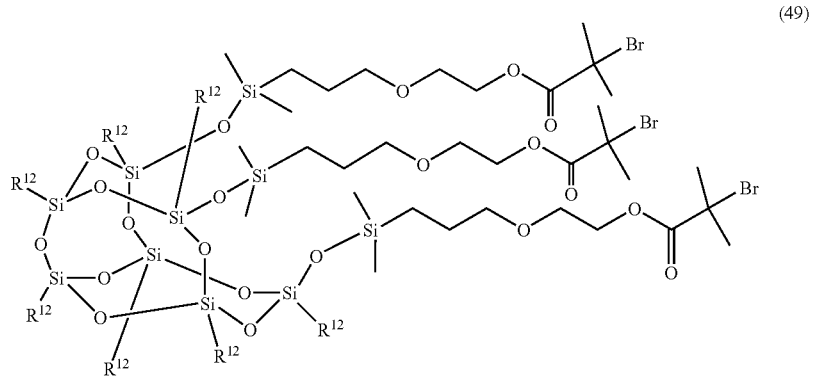

(49)

EXAMPLE 93

A 100 ml Kjeldahl flask was charged with the compound (47-6) (3.15 g) derived by the method described in Example 79, triethylamine (0.925 g) dried on molecular sieves (4a) and dry methylene chloride (36.2 ml) under argon atmosphere. The compound (47-6) was dissolved while stirring at a room temperature by means of a magnetic stirrer, and then the solution was cooled on a dry ice-methanol bath to maintain a solution temperature at −78° C. Then, 2-bromo-2-methylpropanoyl bromide (2.17 g, 4.5 equivalent based on the compound (47-6))) was quickly added to the above solution and stirred at −78° C. for one hour, and then the solution was further stirred at a room temperature for 2 hours. After finishing the reaction, triethylamine-hydrobromic acid salt was removed by filtration. Methylene chloride (100 ml) was added to the reaction solution obtained, and it was washed in order once with water (300 ml), twice with a sodium hydrogencarbonate aqueous solution (1%, 300 ml) and twice with water (300 ml), followed by drying it on anhydrous magnesium sulfate (5 g). Then, the above solution was concentrated at a room temperature by means of a rotary evaporator to reduce a liquid amount to about 5 ml. Heptane (50 ml) was added to this concentrate (5 ml) to subject the viscous liquid component to phase separation. Thereafter, it was left standing still in a freezing chamber to sufficiently subject the viscous liquid component to phase separation, and then this component was obtained by decantation. Methylene chloride (5 ml) was added to the viscous liquid component thus obtained to dissolve it again, and heptane (50 ml) was added thereto, whereby unreacted 2-bromo-2-methylpropanoyl bromide was removed by extraction. A large amount of methylene chloride was added to the viscous liquid component obtained to recover a methylene chloride-soluble part. Activated alumina column was used to refine the methylene chloride-soluble part obtained, and then it was concentrated at 40° C. for 6 hours under reduced pressure to obtain a transparent viscous liquid (2.581 g, yield: 63.6%).

The above transparent viscous liquid had a GPC purity of 96.2%, and it was found from the results of $^1$H-NMR, $^{13}$C-NMR and $^{29}$Si-NMR each shown below that the above compound had a structure represented by Formula (49-6).

IR (KBr method): $v_{v.s}$=1,738 (C=O), $v_{v.s}$=1,319, 1,215 (—CF$_3$), 1,090 to 1,000 (Si—O—Si) cm$^{-1}$.

$^1$H NMR (400 MHz, CDCl$_3$ TMS standard: δ=0.0 ppm): 4.31 (t, 6H, —[CH$_2$]—O—(C=O)—), 3.67 (t, 6H, —[CH$_2$]—O—C$_2$H$_4$—), 3.44 (t, 6H, —C$_3$H$_6$—O—[CH$_2$]—), 2.08 (m, 14H, —[CH$_2$]—CF$_3$), 1.94 (s, 18H, —C(Br) [(CH$_3$)$_2$]), 1.60 (tt, 6H, —CH$_2$— [CH$_2$]—CH$_2$—), 0.84 (m, 14H, Si—[CH$_2$]—CH$_2$—CF$_3$), 0.61 (t, 6H, Si—[CH$_2$]—), 0.15 (s, 18H, —OSi[(CH$_3$)$_2$]—).

$^{13}$C NMR (100 MHz, CDCl$_3$, TMS standard: δ=0.0 ppm): 171.7 ((C=O), 126.9 (—[CF$_3$]), 73.6 (—[CH$_2$]—O—C$_2$H$_4$—), 68.2 (—C$_3$H$_6$—O—[CH$_2$]—), 65.1(—[CH$_2$]—O—(C=O)—), 55.6 (—[C] (Br) (CH$_3$)$_2$), 30.7 (—C(Br) [(CH$_3$)$_2$]), 27.7 (—[CH$_2$]—CF$_3$), 23.3 (—CH$_2$— [CH$_2$]—CH$_2$—), 13.8 (Si—[CH$_2$]—), 4.8 (Si—[CH$_2$]—CH$_2$—CF$_3$—), -0.2 (—OSi[(CH$_3$)$_2$]—).

$^{29}$Si NMR (79 MHz, CDCl$_3$, TMS standard: δ=0.0 ppm): 12.65 (—O[Si](CH$_3$)$_2$CH$_2$—), -66.35, -68.34, -69.59 (CF$_3$ C$_2$H$_4$—SiO$_{1.5}$).

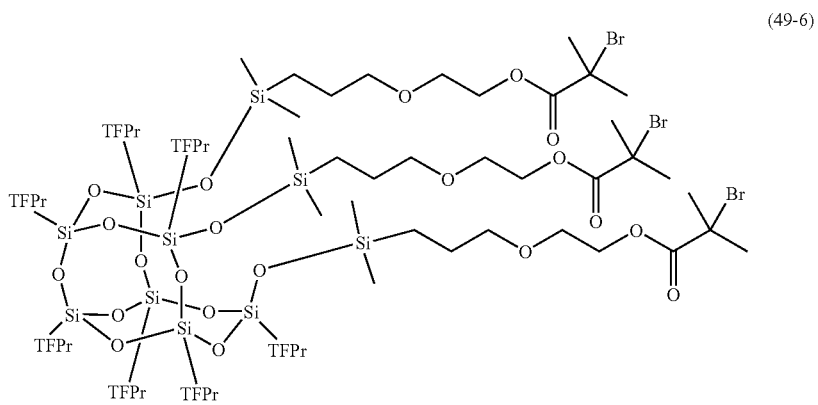

(49-6)

EXAMPLE 94

The same operation as in Example 14 is carried out, except that the compound (37) is used as a raw material and that the solvent is changed from dry methylene chloride to dry HCFC-225, whereby a silicon compound having a 2-bromo-2-methylpropanoyloxyethoxypropyl group represented by Formula (49-7) can be derived.

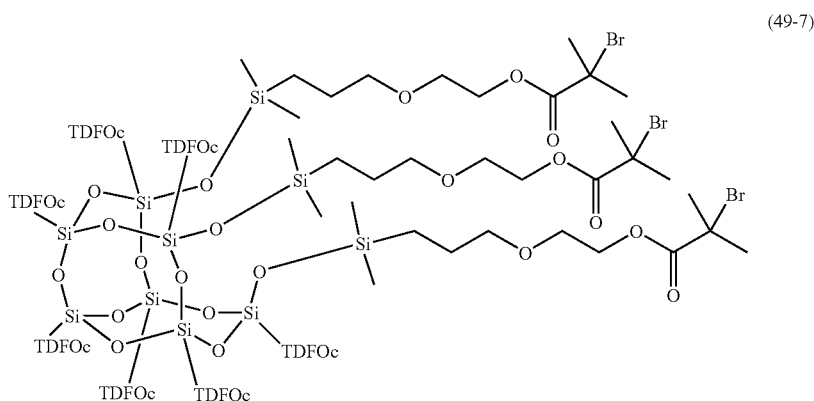

(49-7)

EXAMPLES 95 TO 100

The same operation as in Example 16 is carried out, except that the silsesquioxanes having a hydroxybutyl group which are obtained by the methods described in Examples 81 to 86 are used as raw materials, whereby silicon compounds having a 2-bromo-2-methylpropanoyloxybutyl group represented by Formula (50) and shown in Table 22 can be synthesized.

TABLE 22

| Example No. | Compound name | $R^{12}$ | Raw material compound |
| --- | --- | --- | --- |
| 95 | Compound (50-1) | CH | Compound (48-1) |
| 96 | Compound (50-2) | CP | Compound (48-2) |
| 97 | Compound (50-3) | Et | Compound (48-3) |
| 98 | Compound (50-4) | iBu | Compound (48-4) |
| 99 | Compound (50-5) | iOc | Compound (48-5) |
| 100 | Compound (50-6) | TFPr | Compound (48-6) |

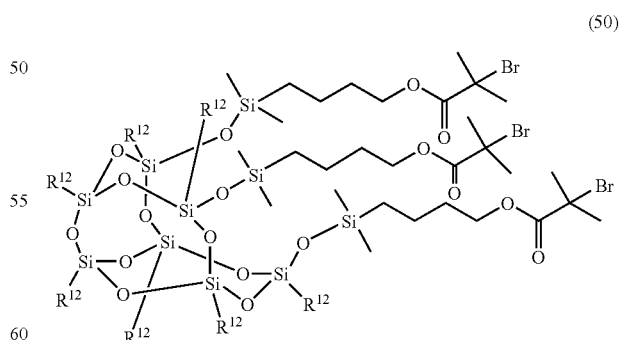

(50)

EXAMPLE 101

The same operation as in Example 16 is carried out, except that the compound (48-7) is used as a raw material and that the solvent is changed from dry methylene chloride to dry HCFC-225, whereby a silicon compound having a 2-bromo-2-methylpropanoyloxybutyl group represented by Formula (50-7) can be synthesized.

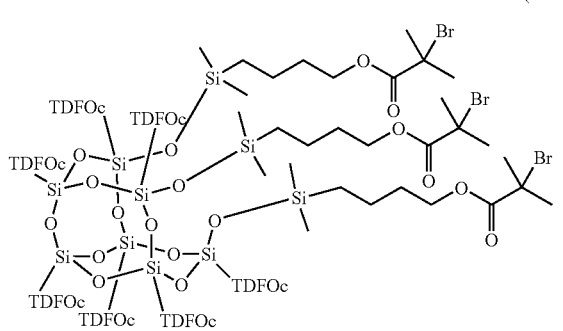

(50-7)

EXAMPLES 102 TO 107

The same operation as in Example 5 is carried out, except that the silsesquioxanes having a chloromethylphenylethyl group which are obtained by the methods described in Examples 67 to 72 are used as raw materials, whereby silicon compounds having a dithiocarbamoyl group represented by Formula (51) and shown in Table 23 can be synthesized.

TABLE 23

| Example No. | Compound name | $R^{12}$ | Raw material compound |
|---|---|---|---|
| 102 | Compound (51-1) | CH | Compound (46-1) |
| 103 | Compound (51-2) | CP | Compound (46-2) |
| 104 | Compound (51-3) | Et | Compound (46-3) |
| 105 | Compound (51-4) | iBu | Compound (46-4) |
| 106 | Compound (51-5) | iOc | Compound (46-5) |
| 107 | Compound (51-6) | TFPr | Compound (46-6) |

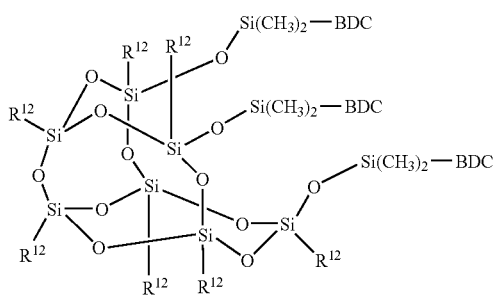

(51)

EXAMPLE 108

The same operation as in Example 5 is carried out, except that the compound (46-7) is used as a raw material and that the solvent is changed from tetrahydrofuran to dry HCFC-225, whereby a silicon compound having a dithiocarbamoyl group represented by Formula (51-7) can be synthesized.

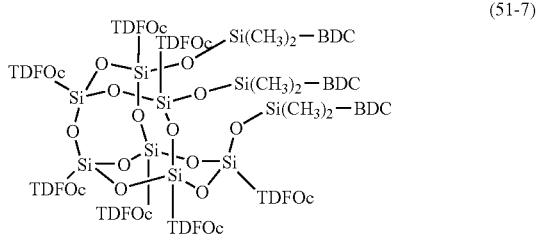

(51-7)

EXAMPLE 109

<Preparation of Solution for Polymerization>

Cuprous bromide was introduced into a heat resistant glass-made ampul in a draft which was cut off from a UV ray, and the compound (49-6)/methyl methacrylate/L-(−)-sparteine/xylene solution was further added and quickly cooled using liquid nitrogen. Then, freezing vacuum deaeration (pressure: 1.0 Pa) was carried out three times by means of a vacuum device equipped with an oil-sealed rotary pump, and the ampul was quickly sealed by means of a hand burner while maintaining a state of vacuum. In this case, a proportion of the compound (49-6), methyl methacrylate, cuprous bromide and L-(−)-sparteine was set to 1:900:3:6 in terms of a molar ratio in the above order, and a use amount of xylene was set to such an amount that a concentration of methyl methacrylate was 30 wt %.

<Polymerization>

The sealed heat resistant glass-made ampul was set in a constant temperature-shaking bath, and polymerization was carried out to obtain a brown viscous solution of a polymer (4a). In this case, the polymerization temperature was 70° C., and the polymerization time was 1.0 hour. Then, the solution of the polymer (4a) was sampled and diluted with tetrahydrofuran, and then it was subjected to GPC measurement. A monomer conversion rate in this polymerization reaction system was analyzed based on a peak area obtained from a GPC measured value of a poly(methyl methacrylate) having a known concentration. The polymer obtained was refined by a reprecipitation method using hexane, and a THF solution (1 wt %) of the above polymer was prepared. This was allowed to pass through a column filled with activated alumina to thereby remove the copper complex by adsorption. Further, this solution was dropwise added to hexane to reprecipitate the polymer, and it was dried (80° C., 6 hours) under reduced pressure. Shown in Table 24-1 are a monomer conversion rate in the above polymerization reaction system, a theoretical number average molecular weight of the polymer (4a) derived from the above monomer conversion rate, the number average molecular weight actually measured by GPC and the molecular weight distribution.

<Analysis of Theoretical Molecular Weight of Graft Chain>

A theoretical molecular weight of the graft chain was calculated from the following equation assuming that an ester bond which was an initiating end in the polymerization was cut off by hydrolysis brought about by hydrofluoric acid treatment and that all terminating ends in the polymerization had become Br. The results thereof are shown in Table 24-2.

<Calculating Equation>

Theoretical Mn of graft chain=(monomer consumption rate (mole %)/100)×$MW_M$×(molar ratio of vinyl base monomer to α-bromoester group)+$MW_1$ <Parameters Used for Calculation>

$MW_M$=100 (methyl methacrylate)

Molar ratio of vinyl base monomer to α-bromoester group=300

$MW_1$=167.01 ($BrC(CH_3)_2CO_2H$)<

<Molecular Weight Measurement of Graft Chain>

A mixed solution of hydrofluoric acid (0.17 ml) and acetonitrile (0.83 ml) was prepared. The polymer (4a) (10 mg) was dissolved in the above mixed solution in a polypropylene-made microtube (1.5 ml) into which a rotator was introduced, and the solution was stirred at 40° C. for 24 hours in an incubator equipped with a magnetic stirrer. Then, the solution was dried up at 80° C. for 3 hours in a vacuum dryer to recover the polymer. The above polymer was subjected to GPC measurement, and the result thereof is shown in Table 24-2.

EXAMPLES 110 TO 114

Polymerization was carried out in the same manner as in Example 109 to obtain the respective brown viscous solutions of a polymer (4b) to a polymer (4e), except that the polymerization time was changed as shown in Table 24-1. The respective polymers were refined in the same manner as in Example 109 to determine a monomer conversion rate, a theoretical number average molecular weight, a number average molecular weight and a molecular weight distribution, and the results thereof are shown in Table 24-1. Calculation of a theoretical number average molecular weight of the graft chain, treatment of the polymer by hydrofluoric acid and analysis of a number average molecular weight and a molecular weight distribution of the graft chain measured by GPC were carried out in the same manner as in Example 109, and the results thereof are shown in Table 24-2. In Examples 111 and 114, the data of the graft chain were not obtained.

TABLE 24-1

| Example | Polymer | Polymerization time (hr) | Conversion rate (mol %) | Mn*1 | Mn*2 | Mw/Mn*3 |
|---|---|---|---|---|---|---|
| 109 | 4a | 0.75 | 1.1 | 3,000 | 3,900 | 1.15 |
| 110 | 4b | 1.00 | 7.6 | 8,900 | 9,400 | 1.15 |
| 111 | 4c | 1.50 | 10.6 | 11,500 | 13,100 | 1.15 |
| 112 | 4d | 2.00 | 11.8 | 12,600 | 12,900 | 1.16 |
| 113 | 4e | 2.50 | 15.9 | 16,300 | 15,200 | 1.20 |
| 114 | 4f | 5.00 | 27.8 | 27,000 | 24,300 | 1.16 |

*1theoretical value
*2measured value
*3measured value

TABLE 24-2

| | (data of graft chain) | | |
|---|---|---|---|
| Example | Polymer | Mn*1 | Mw*2 | Mw/Mn*3 |
| 109 | 4a | 500 | 1,900 | 1.11 |
| 110 | 4b | 2,400 | 4,600 | 1.13 |
| 112 | 4d | 3,700 | 5,900 | 1.12 |
| 113 | 4e | 4,900 | 7,200 | 1.15 |

*1theoretical value
*2measured value
*3measured value

INDUSTRIAL APPLICABILITY

The silicon compound provided by the present invention is a silsesquioxane derivative and has an excellent living-polymerizable radical polymerization-initiating function. The silicon compound of the present invention shows an excellent living radical polymerization-accelerating function particularly to styrene derivatives and (meth)acrylic acid derivatives. For example, it is possible to initiate polymerization of a (meth)acryl base monomer by the silicon compound of the present invention to form a (meth)acryl base polymer with 3 points in the silsesquioxane structure of the present invention being utilized as starting points. In the polymer thus obtained having an organic group of a silsesquioxane structure at an end, it is possible as well to positively make use of interaction between the organic groups of the silsesquioxane structure thereof. This makes it possible not only to obtain an organic-inorganic composite material having a distinct structure but also to control the structure thereof as the molecular aggregate of the above polymer. Further, the silicon compound of the present invention has characteristics other than the function of a polymerization initiator. For example, α-haloester has a strong electrophilicity, and therefore reaction of the silicon compound of the present invention with nucleophilic reagents makes it possible to synthesize various silsesquioxane derivatives corresponding to the nucleophilic reagents. Accordingly, the silicon compound of the present invention is also useful as an intermediate in organic synthesis.

The invention claimed is:

1. A silicon compound represented by Formula (1):

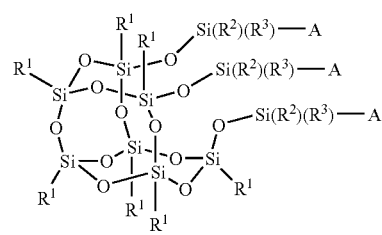

(1)

wherein each $R^1$ is independently selected from the group consisting of 2-fluoroethyl, 2,2-difluoroethyl, 3,3,3-trifluoropropyl, hexafluoropropyl, nonafluoro-1,1,2,2-tetrahydrohexyl, tridecafluoro-1,1,2,2-tetrahydrooctyl, heptadecafluoro-1,1,2,2-tetrahydrodecyl, perfluoro-1H,1H,2H,2H-dodecyl and perfluoro-1H,1H,2H,2H-tetradecyl; each $R^2$ and $R^3$ is independently selected from the group consisting of alkyl having a carbon atom number of 1 to 8, phenyl and cyclohexyl; and A is a group having a polymerization initiating ability for a monomer.

2. The silicon compound as described in claim 1, wherein A is a group having a living radical polymerization initiating ability for a monomer.

3. The silicon compound as described in claim 1, wherein A is a group represented by any of Formula (2-1), Formula (2-2) and Formula (2-3):

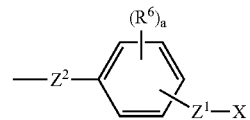

(2-1)

wherein $Z^1$ is alkylene having a carbon atom number of 1 to 3 in which optional —$CH_2$— may be substituted with —O—; $Z_2$ is alkylene having a carbon atom number of 2 to 10 in which optional —$CH_2$— may be substituted with —O—, —COO— or —OCO—; $R^6$ is alkyl having a carbon atom number of 1 to 3; a is an integer of 0 to 2; X is halogen; and a bonding position of $Z^1$ on a benzene ring is a meta position or a para position to a bonding position of $Z^2$, and a bonding position of $R^6$ is an optional position excluding the respective bonding positions of $Z^1$ and $Z^2$;

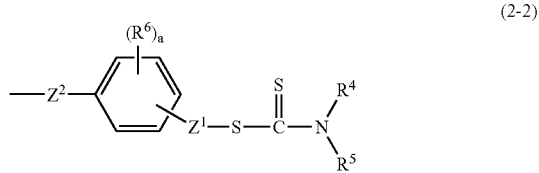

(2-2)

wherein $R^4$ and $R^5$ are independently selected from the group consisting of hydrogen, alkyl having a carbon atom number of 1 to 12, cycloalkyl having a carbon atom number of 5 to 10 and aryl having a carbon atom number of 6 to 10, and $R^4$ and $R^5$ may be combined with each other to form a ring together with N; $Z^1$ is alkylene having a carbon atom number of 1 to 3 in which optional —$CH_2$— may be substituted with —O—; $Z^2$ is alkylene having a carbon atom number of 2 to 10 in which optional —$CH_2$— may be substituted with —O—, —COO— or —OCO—; $R^6$ is alkyl having a carbon atom number of 1 to 3; a is an integer of 0 to 2; and a bonding position of $Z^1$ on a benzene ring is a meta position or a para position to a bonding position of $Z^2$, and a bonding position of $R^6$ is an optional position excluding the respective bonding positions of $Z^1$ and $Z^2$;

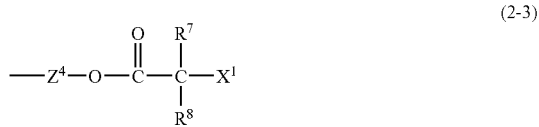

(2-3)

wherein $Z^4$ is selected from the group consisting of alkylene having a carbon atom number of 2 to 20 and alkenylene having a carbon atom number of 3 to 8, and optional —$CH_2$— in these alkylene and alkenylene may be substituted with —O—; $R^7$ is selected from the group consisting of hydrogen, alkyl having a carbon atom number of 1 to 20, aryl having a carbon atom number of 6 to 20 and arylalkyl having a carbon atom number of 7 to 20; $R^8$ is selected from the group consisting of alkyl having a carbon atom number of 1 to 20, aryl having a carbon atom number of 6 to 20 and arylalkyl having a carbon atom number of 7 to 20; and $X^1$ is halogen.

4. The silicon compound as described in claim 3, wherein all $R^1$'s are 3,3,3-trifluoropropyl; and $R^2$ and $R^3$ are methyl.

5. The silicon compound as described in claim 3, wherein all $R^1$'s are the same group, and are selected from the group consisting of 3,3,3-trifluoropropyl and tridecafluoro-1,1,2,2-tetrahydrooctyl; A is the group represented by Formula (2-1); $Z^2$ in Formula (2-1) is $Z^3$-$C_2H_4$—; and $Z^3$ is a single bond or alkylene having a carbon atom number of 1 to 8 in which optional —$CH_2$— may be substituted with —O—, —COO— or —OCO—.

6. The silicon compound as described in claim 3, wherein all $R^1$'s are 3,3,3-trifluoropropyl; $R^2$ and $R^3$ are methyl; A is the group represented by Formula (2-1); and in Formula (2-1), $Z^1$ is —$CH_2$—; $Z^2$ is —$C_2H_4$—; X is chlorine or bromine; and a is 0.

7. The silicon compound as described in claim 3, wherein all $R^1$'s are the same group, and are selected from the group consisting of 3,3,3-trifluoropropyl and tridecafluoro-1,1,2,2-tetrahydrooctyl; A is the group represented by Formula (2-2); and in Formula (2-2), $Z^2$ is $Z^3$-$C_2H_4$—, and $Z^3$ is a single bond or alkylene having a carbon atom number of 1 to 8 in which optional —$CH_2$— may be substituted with —O—, —COO— or —OCO—.

8. The silicon compound as described in claim 3, wherein all $R^1$'s are 3,3,3-trifluoropropyl; $R^2$ and $R^3$ are methyl; A is the group represented by Formula (2-2); and in Formula (2-2), $R^4$ and $R^5$ are ethyl; $Z^1$ is —$CH_2$—; $Z^2$ is —$C_2H_4$—; and a is 0.

9. The silicon compound as described in claim 3, wherein all $R^1$'s are the same group, and are selected from the group consisting of 3,3,3-trifluoropropyl and tridecafluoro-1,1,2,2-tetrahydrooctyl; A is the group represented by Formula (2-3); and $Z^4$ in Formula (2-3) is alkylene having a carbon atom number of 2 to 10 in which optional —$CH_2$— may be substituted with —O—.

10. The silicon compound as described in claim 3, wherein all $R^1$'s are 3,3,3-trifluoropropyl; $R^2$ and $R^3$ are methyl; A is the group represented by Formula (2-3); and in Formula (2-3), $Z^4$ is —$C_2H_4$—, —$C_3H_6$— or —$C_2H_4$—O—$C_3H_6$—; $R^7$ and $R^8$ are methyl; and $X^1$ is bromine.

* * * * *